US012590151B2

(12) United States Patent
Hofer et al.

(10) Patent No.: US 12,590,151 B2
(45) Date of Patent: Mar. 31, 2026

(54) ANTI-HUMAN CD19 ANTIBODIES WITH HIGH AFFINITY

(71) Applicant: Hoffmann-La Roche Inc., Little Falls, NJ (US)

(72) Inventors: Thomas Hofer, Zürich (CH); Claudia Ferrara Koller, Zug (CH); Ekkehard Moessner, Kreuzlingen (CH); Mi He, Zürich (CH)

(73) Assignee: Hoffmann-La Roche Inc., Little Falls, NJ (US)

(*) Notice: Subject to any disclaimer, the term of this patent is extended or adjusted under 35 U.S.C. 154(b) by 708 days.

(21) Appl. No.: 18/052,526

(22) Filed: Nov. 3, 2022

(65) Prior Publication Data

US 2023/0312710 A1     Oct. 5, 2023

Related U.S. Application Data

(63) Continuation of application No. 16/689,880, filed on Nov. 20, 2019, now abandoned, which is a continuation of application No. 15/941,519, filed on Mar. 30, 2018, now abandoned, which is a continuation of application No. PCT/EP2016/073062, filed on Sep. 28, 2016.

(30) Foreign Application Priority Data

Oct. 2, 2015     (EP) ..................................... 15188262
May 2, 2016     (EP) ..................................... 16167893

(51) Int. Cl.
| | |
|---|---|
| *A61K 39/395* | (2006.01) |
| *A61P 35/00* | (2006.01) |
| *C07K 16/28* | (2006.01) |
| *C07K 16/30* | (2006.01) |

(52) U.S. Cl.
CPC .......... *C07K 16/2803* (2013.01); *A61P 35/00* (2018.01); *C07K 16/3061* (2013.01); *C07K 2317/24* (2013.01); *C07K 2317/31* (2013.01); *C07K 2317/33* (2013.01); *C07K 2317/56* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,565,332 A | 10/1996 | Hoogenboom et al. | |
| 5,731,168 A | 3/1998 | Carter et al. | |
| 5,821,333 A | 10/1998 | Carter et al. | |
| 5,869,046 A | 2/1999 | Presta et al. | |
| 6,171,586 B1 | 1/2001 | Lam et al. | |
| 6,267,958 B1 | 7/2001 | Andya et al. | |
| 6,737,056 B1 | 5/2004 | Presta et al. | |
| 6,982,321 B2 | 1/2006 | Winter et al. | |
| 7,087,409 B2 | 8/2006 | Barbas et al. | |
| 7,332,581 B2 | 2/2008 | Presta et al. | |
| 7,521,541 B2 | 4/2009 | Eigenbrot et al. | |
| 7,527,791 B2 | 5/2009 | Adams et al. | |
| 7,695,936 B2 | 4/2010 | Carter et al. | |
| 8,097,703 B2 | 1/2012 | Rao-Naik et al. | |
| 8,323,653 B2 | 12/2012 | Damschroder et al. | |
| 8,524,867 B2 | 9/2013 | Bernett et al. | |
| 8,883,992 B2 | 11/2014 | Damschroder et al. | |
| 2004/0132028 A1 | 7/2004 | Stumpp et al. | |
| 2006/0233791 A1 | 10/2006 | Tedder et al. | |

FOREIGN PATENT DOCUMENTS

| | | |
|---|---|---|
| KR | 2009-0059149 A | 6/2009 |
| KR | 2012-0099647 A | 9/2012 |
| WO | 02/020565 A2 | 3/2002 |
| WO | 03/048209 A1 | 6/2003 |
| WO | 2006/044908 A2 | 4/2006 |
| WO | 2006/089133 A2 | 8/2006 |
| WO | 2007/02223 A2 | 1/2007 |
| WO | 2008/022152 A2 | 2/2008 |
| WO | WO2008022152 * | 2/2008 |
| WO | 2008/031056 A2 | 3/2008 |
| WO | 2010/095031 A2 | 8/2010 |
| WO | WO2011051307 A1 | 5/2011 |
| WO | 2011/147834 A1 | 12/2011 |
| WO | 2012/010561 A1 | 1/2012 |
| WO | 2012/130831 A1 | 10/2012 |
| WO | 2015/130766 A1 | 9/2015 |
| WO | 2016/048938 A1 | 3/2016 |
| WO | 2016/075278 A1 | 5/2016 |
| WO | WO2016075278 * | 5/2016 |
| WO | 2017/055541 A1 | 4/2017 |

OTHER PUBLICATIONS

Almagro, J., et al., "Humanization of antibodies" Front Biosci 13(5):1619-1633 (Jan. 1, 2008).
Bonifacino, J., et al., "Commonly Used Techniques: Molecular Biology Techniques" Curr Protocols in Cell Biol 8(1):1-4 (Oct. 1, 2000).
Carter, R., et al., "Roles of CD19 Signal Transduction in B Cell Biology" Immunol Res 26(1-3):45-54 (Aug. 1, 2002).
Chang, K., et al., "Affinity Maturation of an Epidermal Growth Factor Receptor Targeting Human Monoclonal Antibody ER414 by CDR Mutation" Immune Netw 12(4):155-164 (Aug. 1, 2012).
Chothia, C., et al., "Canonical structures for the hypervariable regions of immunoglobulins" J Mol Biol 196(4):901-917 (Aug. 20, 1987).

(Continued)

*Primary Examiner* — Meera Natarajan
(74) *Attorney, Agent, or Firm* — GENENTECH, INC.

(57) ABSTRACT

The present invention relates to antibodies against human CD19 (anti-human CD19 antibodies), methods for their production, pharmaceutical compositions containing these antibodies, and methods of using the same.

25 Claims, 8 Drawing Sheets

Specification includes a Sequence Listing.

(56) References Cited

OTHER PUBLICATIONS

Conry, R., et al., "Phase I trial of an anti-CD19 deglycosylated ricin a chain immunotoxin in non-hodgkin's lymphoma: Effect of an intensive schedule of administration" J Immunother Emphasis Tumor Immunol 18(4):231-241 (Nov. 1, 1995).

Dall'Acqua, W., et al., "Antibody humanization by framework shuffling" Methods 36(1):43-60 (Jan. 17, 2005).

Daugherty, P., et al., "Quantitative analysis of the effect of the mutation frequency on the affinity maturation of single chain Fv antibodies" PNAS USA 97(5):2029-2034 (Feb. 29, 2000).

Hardcastle, I., et al., "Isoindolinone Inhibitors of the Murine Double Minute 2 (MDM2)-p53 Protein-Protein Interaction: Structure-Activity Studies Leading to Improved Potency" J Med Chem 54(5):1233-1243 (Mar. 10, 2011).

Hekman, A., et al., "Initial experience with treatment of human B cell lymphoma with anti-CD 19 monoclonal antibody" Cancer Immunol Immun 32(6):364-372 (Jan. 1, 1991).

Hoogenboom, H., et al., "Overview of antibody phage-display technology and its applications" Methods Mol Biol 178:1-37 (Jan. 1, 2002).

"International Preliminary Report on Patentability—PCT/EP2016/073062 (Report Issuance Date: Apr. 3, 2018; Chapter I),": pp. 1-9 (Apr. 12, 2018).

"International Search Report—PCT/EP2016/07362" (w/Written Opinion), :pp. 1-17 (Dec. 13, 2016).

Jendeberg, L., et al., "Engineering of Fc(1) and Fc(3) from human immunoglobulin G to analyse subclass specificity for staphylococcal protein A" J Immunol Methods 201(1):25-34 (Feb. 14, 1997).

Jones, P.T., et al., "Replacing the Complementarity-Determining Regions in a Human Antibody with Those From a Mouse" Nature 321(6069):522-525 (May 29, 1986).

Kabat, E., et al. U.S. Dept. of Health and Human Services, Public Health Services, NIH Publ. No. 91-3242:3 "Sequences of Proteins of Immunological Interest" (1983).

Kabat, E.A., et al. Sequences of Proteins of Immunological Interest: Tabulation and Analysis of Amino Acid and Nucleic Acid Sequences of Precursors, V-Regions, C-Regions, J-Chain T-Cell Receptors for Antigen, T-Cell Surface Antigens, β-2 Microglobulins, Major Histocompatibility Antigens, Thy-1, Complement, C-Reactive Protein, Thymopoietin, Integrins, Post-gamma Globulin, α2-Macroglobulins, and Other Related Proteins (NIH Publication No. 91-3242), Fifth edition, Bethesda, MD-US::647-669 (1991).

Kashmiri, S., et al., "SDR grafting—a new approach to antibody humanization" Methods 36:25-34 (Jan. 1, 2005).

Klimka, A. et al., "Human anti-CD30 recombinant antibodies by guided phage antibody selection using cell panning" Brit J Cancer 83(2):252-260 (Jun. 15, 2000).

Kohl, A., et al., "Designed to be stable: Crystal structure of a consensus ankyrin repeat protein" PNAS 100(4):1700-1705 (Feb. 18, 2003).

Lonberg, N., et al., "Fully human antibodies from transgenic mouse and phage display platforms" Curr Opin Immunol 20(4):450-459 (Aug. 1, 2008).

Lonberg, N.., "Human antibodies from transgenic animals" Nat Biotechnol 23(9):1117-1125 (Sep. 7, 2005).

Manzke, O., et al., "Locoregional treatment of low-grade B-cell lymphoma with CD3xCD19 bispecific antibodies and CD28 costimulation. II. Assessment of cellular immune responses" Int J Cancer 91(4):516-522 (Feb. 15, 2001).

Mariuzza, R. et al., "The structural basis of antigen-antibody recognition" Annu Rev Biophys Chem 16:139-159 (Jun. 1, 1987).

Merchant, A., et al., "An efficient route to human bispecific IgG" Nat Biotechnol 16(7):677-681 (Jul. 1, 1998).

Morrison, S., et al., "Chimeric human antibody molecules: Mouse antigen-binding domains with human constant region domains" PNAS USA 81(21):6851-6855 (Nov. 1, 1984).

Morrison, S., et al., "Genetically Engineered Antibody Molecules" Adv Immunol 44:65-92 (Jan. 1, 1989).

Osbourn, J., et al., "From rodent reagents to human therapeutics using antibody guided selection" Methods 36:61-68 (May 1, 2005).

Padlan, E. et al., "A possible procedure for reducing the immunogenicity of antibody variable domains while preserving their ligand-binding properties" Mol Immunol 28(4-5):489-498 (Apr. 30, 1991).

Padlan, E. et al., "Anatomy of the Antibody Molecule" Mol Immunol 31(3):169-217 (Feb. 1, 1994).

Ponsel, D., et al., "High Affinity, Develop ability and Functional Size: The Holy Grail of Combinatorial Antibody Library Generation" Molecules 16(5):3675-3700 (May 3, 2011).

Queen, C., et al., "A humanized antibody that binds to the interleukin 2 receptor" PNAS USA 86(24):10029-10033 (Dec. 1, 1989).

Rajpal, A., et al., "A general method for greatly improving the affinity of antibodies by using combinatorial libraries" PNAS USA 102(24):8466-8471 (Jun. 1, 2005).

Remington, J., et al. Remington's Pharmaceutical Sciences (Table of Contents, total in 4 pages), Osol , eds., 16th edition, Easton, PA: Mack Publishing Company, (Jan. 1, 1980).

Ridgway, J., et al., "Knobs-into-holes' engineering of antibody CH3 domains for heavy chain heterodimerization" Protein Eng 9(7):617-621 (Jul. 1, 1996).

Riechmann, L., et al., "Reshaping human antibodies for therapy" Nature 332:323-327 (Mar. 24, 1988).

Roguska, M., et al., "A comparison of two murine monoclonal antibodies humanized by CDR-grafting and variable domain resurfacing" Protein Eng 9(10):895-904 (Oct. 1, 1996).

Silacci, M., et al., "Design, construction, and characterization of a large synthetic human antibody phage display library" Proteomics 5(9):2340-2350 (Jun. 1, 2005).

Singer, M., et al. Genes and Genomes "Chapter 1.3: Structure of Proteins" (Geny i genomy Moscow: Mir, 1991), Berg, P., ed., Osney Mead, Oxford-UK: Blackwell Scientific Publications,:67-69 (Jan. 1, 1991).

Steidl, S., et al., "In vitro affinity maturation of human GM-CSF antibodies by targeted CDR-diversification" Mol Immunol 46(1):135-144 (Nov. 1, 2008).

Thie, H. Antibody Engineering "Chapter 26: Affinity Maturation by Random Mutagenesis and Phage Display" Kontermann, R. and Dubel, S., eds., Berlin Heidelberg, DE: Springer-Verlag Berlin, vol. 1:397-409 (Jan. 1, 2010).

Van Dijk, M., et al., "Human antibodies as next generation therapeutics" Curr Opin Chem Biol 5(4):368-374 (Aug. 1, 2001).

Verhoeyen, M., et al., "Reshaping human antibodies: Grafting an anti-lysozyme activity" Science 239(4847):1534-1536 (Mar. 25, 1988).

Vlasveld, L.T., et al., "Treatment of low-grade non-Hodgkin's lymphoma with continuous infusion of low-dose recombinant interleukin-2 in combination with the B-cell-specific monoclonal antibody CLB-CD19" Cancer Immunol Immunother 40(1):37-47 (Jan. 1, 1995).

Yang, W. et al., "CDR walking mutagenesis for the affinity maturation of a potent human anti-HIV-1 antibody into the picomolar range" J Mol Biol 254(3):392-403 (Jan. 1, 1995).

Yazawa,N., et al., "Immunotherapy using unconjugated CD19 monoclonal antibodies in animal models for B lymphocyte malignancies and autoimmune disease" PNAS 102(42):15178-15183 (Oct. 18, 2005).

* cited by examiner

Fig. 1

CDRs according to Kabat numbering

8B8 VL sequence

8B8 VH sequence x = randomized positions parental

2B11

5D08

5B08

2B03

7H07

5A07

5H09

ANTI-HUMAN CD19 ANTIBODIES WITH HIGH AFFINITY

CROSS REFERENCE TO RELATED APPLICATIONS

This application is a continuation of U.S. patent application Ser. No. 16/689,880, filed Nov. 20, 2019, which is a continuation of U.S. patent application Ser. No. 15/941,519, filed Mar. 30, 2018, which is a continuation of International Patent Application No. PCT/EP2016/073062, filed Sep. 28, 2016, published as WO 2017/055328, which claims priority to European Patent Application No. 16167893.3, filed May 2, 2016, and to European Patent Application No. 15188262.8, filed Oct. 2, 2015, each of which are incorporated herein by reference in its entirety.

SEQUENCE LISTING

The present application contains a Sequence Listing, which has been submitted in XML format and is hereby incorporated by reference in its entirety. Said XML copy, created on May 12, 2023, is named P33118-US-2 SL.xml, and is 265,389 bytes in size.

FIELD OF THE INVENTION

The present invention relates to humanized antibodies against human CD19 (anti-human CD19 antibody), methods for their production, pharmaceutical compositions containing these antibodies, and methods of using the same.

BACKGROUND

Human CD19 is a 95 kDa transmembrane protein (B-cell co-receptor) exclusively expressed on B-cells and on follicular dendritic cells. CD 19 is found in association with CD21 and CD81. CD19 and CD21 are required for normal B-cell differentiation (Carter, R. H., et al., Immunol. Res. 26 (2002) 45-54). Antibodies against CD19 have been used in several clinical trials (see e.g. Hekman, A., et al., Cancer Immunol. Immunother. 32 (191) 364-372; Vlasfeld, L. T., et al., Cancer Immunol. Immunother. 40 (1995) 37-47; Conry, R. M., et al., J. Immunother. Emphasis Tumor Immunol. 18 (1995) 231-241; Manzke, O., et al., Int. J. Cancer 91 (2001) 516-522).

Antibodies against CD19 can have inhibitory or stimulating effects on B-cell activation. Binding of CD19 antibodies to mitogen-stimulated B-cells inhibits the subsequent rise in Ca2+ and the resulting activation and proliferation of these cells and B-cell proliferation and differentiation can either be inhibited or enhanced by CD19 antibody depending on the mitogenic stimulus used and the degree of crosslinking by the antibody. Cancers to be treated by antibodies against CD19 include, for example, B-cell lineage malignancies such as, for example, B cell lymphomas or B cell leukemias, including, but not limited to, non-Hodgkin lymphoma, chronic lymphocytic leukemia, and acute lymphoblastic leukemia. Antibodies against CD19 may also be useful for the treatment of autoimmune diseases, rheumatoid arthritis, lupus, psoriasis, or a bone disease.

In WO 2011/147834 antibodies against CD19 and uses thereof are reported. However, it has been found that these antibodies have certain deamidation hotspots in their sequences. The antibodies described herein are not only characterized by sequences devoid of these deamidation hotspots, they also possess a higher affinity to the target CD19.

SUMMARY OF THE INVENTION

In one aspect, the invention provides anti-human CD19 antibodies with high affinity.

In one aspect, provided is an antibody, that specifically binds to human CD19 with a higher affinity than an antibody comprising a variable heavy chain comprising an amino acid sequence of SEQ ID NO:113 and a variable light chain comprising an amino acid sequence of SEQ ID NO:114.

In another aspect, provided is an antibody that specifically binds to human CD19, wherein the antibody comprises
  (a) CDR-L1 comprising the amino acid sequence of SEQ ID NO: 43,
  (b) CDR-L2 comprising the amino acid sequence of SEQ ID NO: 44,
  (c) CDR-L3 comprising the amino acid sequence of SEQ ID NO: 45,
  (d) CDR-H1 comprising the amino acid sequence of SEQ ID NO: 46,
  (e) CDR-H2 comprising the amino acid sequence of SEQ ID NO: 47, and
  (f) CDR-H3 comprising the amino acid sequence of SEQ ID NO: 48.

In a further aspect, the antibody is a monoclonal antibody. In another aspect, the antibody is a human, humanized or chimeric antibody. In another aspect, the antibody is an antibody fragment that specifically binds to human CD19.

In a particular aspect, provided is an antibody, wherein the antibody comprises a VH domain comprising an amino acid sequence of SEQ ID NO: 99 and a VL domain comprising an amino acid sequence of SEQ ID NO: 100.

In a further aspect, provided is an antibody as described herein before, which is a full length IgG1 antibody.

In a particular aspect, provided is an antibody as described herein, which is a full length IgG1 antibody with mutations L234A, L235A and P329G (numbering according to the EU index of Kabat).

In a particular aspect, provided is an antibody as described herein, which is a full length IgG1 antibody with mutations L234A, L235A and P329G (numbering according to the EU index of Kabat).

In a further aspect, provided is an antibody as described herein, which is cross reactive for human and cynomolgus CD19.

In another aspect, provided is an antibody that is bispecific, wherein said antibody specifically binds to human CD19 and a second antigen binding moiety, wherein the antibody comprises
  (a) CDR-L1 comprising the amino acid sequence of SEQ ID NO: 43,
  (b) CDR-L2 comprising the amino acid sequence of SEQ ID NO: 44,
  (c) CDR-L3 comprising the amino acid sequence of SEQ ID NO: 45,
  (d) CDR-H1 comprising the amino acid sequence of SEQ ID NO: 46,
  (e) CDR-H2 comprising the amino acid sequence of SEQ ID NO: 47, and
  (f) CDR-H3 comprising the amino acid sequence of SEQ ID NO: 48.

According to another aspect of the invention, there is provided an isolated polynucleotide encoding an antibody as defined herein before. The invention further provides a vector, particularly an expression vector, comprising the isolated polynucleotide of the invention and a host cell comprising the isolated polynucleotide or the vector of the invention. In some embodiments the host cell is a eukaryotic cell, particularly a mammalian cell.

In another aspect, provided is a method for producing the antibody of the invention, comprising the steps of (i) culturing the host cell of the invention under conditions suitable for expression of the antigen binding molecule, and (ii) recovering the antigen binding molecule. The invention also encompasses an antibody produced by the method of the invention.

The invention further provides a pharmaceutical composition comprising the antibody of the invention and at least one pharmaceutically acceptable excipient.

Also encompassed by the invention is the antibody of the invention, or the pharmaceutical composition of the invention, for use as a medicament. In one aspect is provided the antibody of the invention, or the pharmaceutical composition of the invention, for use in the treatment of a disease in an individual in need thereof. In a specific aspect, provided is the antibody of the invention, or the pharmaceutical composition of the invention, for use in the treatment of cancer. In another aspect, provided is the antibody of the invention, or the pharmaceutical composition of the invention, for use in the treatment autoimmune diseases, rheumatoid arthritis, lupus, psoriasis, or a bone disease.

Also provided is the use of the antibody of the invention for the manufacture of a medicament for the treatment of a disease in an individual in need thereof, in particular for the manufacture of a medicament for the treatment of cancer, as well as a method of treating a disease in an individual, comprising administering to said individual a therapeutically effective amount of a composition comprising the antibody in a pharmaceutically acceptable form. In a specific aspect, the disease is cancer. In another aspect, the disease is selected from the group consisting of autoimmune diseases, rheumatoid arthritis, lupus, psoriasis, or a bone disease. In any of the above embodiments the individual is preferably a mammal, particularly a human.

BRIEF DESCRIPTION OF THE DRAWINGS

In FIG. 1 is illustrated the randomization strategy for the CDR regions of the parental clone 8B8. Shown are the variable domains of the parental clone 8B8 and the CDR regions (boxed) according to the numbering of Kabat. The VL sequence corresponds to SEQ ID NO:114 and the VH sequence corresponds to SEQ ID NO:113. (X) represents the randomized positions.

FIG. 3 discloses SEQ ID NOS 120-135, respectively, in order of appearance.

DETAILED DESCRIPTION OF THE INVENTION

Definitions

Figure 2:
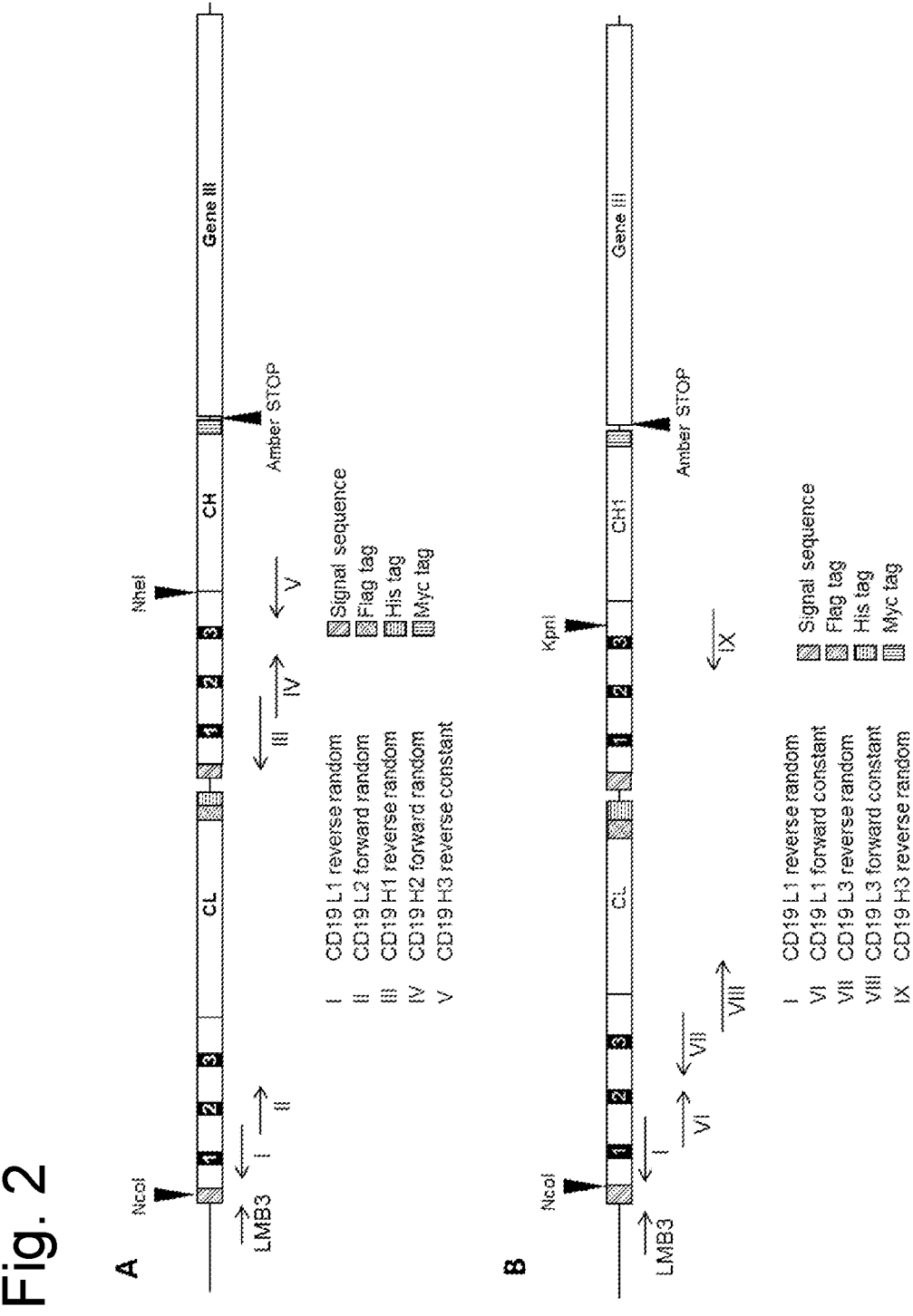
FIG. 2 shows the schematic description of the library generation strategies. Shown is the PCR amplification and cloning strategy used for the generation of the 8B8-based library with A) randomized CDR1 and CDR2 regions in the light and heavy chain or B) randomized CDR1 and CDR3 regions in the light and CDR3 region in the heavy chain. Respective enzymes used for cloning into the phagemide are indicated.

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant Examples of antigen binding molecules are antibodies, antibody fragments and scaffold antigen binding proteins.

The term "antigen binding moiety" refers to a polypeptide molecule that specifically binds to an antigenic determinant. In one aspect, the antigen binding moiety is able to activate signaling through its target cell antigen. In a particular aspect, the antigen binding moiety is able to direct the entity to which it is attached to a target site. Antigen binding moieties include antibodies and fragments thereof capable of specific binding to a target cell antigen. In addition, antigen binding moieties capable of specific binding to a target cell antigen include scaffold antigen binding proteins as defined herein below, e.g. binding domains which are based on designed repeat proteins or designed repeat domains such as designed ankyrin repeat proteins (DARPins) (see e.g. WO 2002/020565) or Lipocalins (Anticalin).

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ) based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments in which the cysteine residue(s) of the constant domains bear a free thiol group. Pepsin treatment yields an F(ab')$_2$ fragment that has two antigen-combining sites (two Fab fragments) and a part of the Fc region.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab (vLvii). On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin).

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details see Journal of Immunological Methods 248 (1-2), 31-45 (2001).

Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633.

An affibody is a scaffold derived from Protein A of *Staphylococcus aureus* which can be engineered to bind to antigen. The domain consists of a three-helical bundle of approximately 58 amino acids. Libraries have been generated by randomization of surface residues. For further details see Protein Eng. Des. Sel. 17, 455-462 (2004) and EP 1641818A1.

Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007).

A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

A single-domain antibody is an antibody fragment consisting of a single monomeric variable antibody domain. The first single domain were derived from the variable domain of the antibody heavy chain from camelids (nanobodies or Vali fragments). Furthermore, the term single-domain antibody includes an autonomous human heavy chain variable domain (aVH) or $V_{NAR}$ fragments derived from sharks.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataBI and conotoxin and knottins. The microproteins have a loop which can be engineered to include up to 25 amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, a molecule that binds to the antigen has a dissociation constant (Kd) of $\leq 1$ $\mu$M, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

The term "CD19" refers to B-lymphocyte antigen CD19, also known as B-lymphocyte surface antigen B4 or T-cell surface antigen Leu-12 and includes any native CD19 from any vertebrate source, including mammals such as primates (e.g. humans) non-human primates (e.g. cynomolgus monkeys) and rodents (e.g. mice and rats), unless otherwise indicated. The amino acid sequence of human CD19 is shown in Uniprot accession no. P15391 (version 160, SEQ ID NO: 115). The term encompasses "full-length" unprocessed human CD19 as well as any form of human CD19 that results from processing in the cell as long as the antibody as reported herein binds thereto. CD19 is a structurally distinct cell surface receptor expressed on the surface of human B cells, including, but not limited to, pre-B cells, B cells in early development (i.e., immature B cells), mature B cells through terminal differentiation into plasma cells, and malignant B cells. CD19 is expressed by most pre-B acute lymphoblastic leukemias (ALL), non-Hodgkin's lymphomas, B cell chronic lymphocytic leukemias (CLL), prolymphocytic leukemias, hairy cell leukemias, common acute lymphocytic leukemias, and some Null-acute lymphoblastic leukemias. The expression of CD19 on plasma cells further suggests it may be expressed on differentiated B cell tumors such as multiple myeloma. Therefore, the CD19 antigen is a target for immunotherapy in the treatment of non-Hodgkin's lymphoma, chronic lymphocytic leukemia and/or acute lymphoblastic leukemia.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987)). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., *Sequences of Proteins of Immunological Interest,* 5th Ed. Public Health Service, National Institutes of Health, Bethesda, MD (1991)). Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

| | CDR Definitions[1] | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

As used herein, the term "affinity matured" in the context of antigen binding molecules (e.g., antibodies) refers to an antigen binding molecule that is derived from a reference antigen binding molecule, e.g., by mutation, binds to the same antigen, preferably binds to the same epitope, as the reference antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial reference antigen binding molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$ respectively.

A "humanized" antibody refers to a chimeric antibody comprising amino acid residues from non-human HVRs and amino acid residues from human 1-Rs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, M D, 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

An "ectodomain" is the domain of a membrane protein that extends into the extracellular space (i.e. the space outside the target cell). Ectodomains are usually the parts of proteins that initiate contact with surfaces, which leads to signal transduction.

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$ (SEQ ID NO: 116), $(SG_4)_n$ (SEQ ID NO: 117) or $G_4(SG_4)_n$_(SEQ ID NO: 118) peptide linkers, wherein "n" is generally a number between 1 and 10, typically between 1 and 4, in particular 2.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues.

"Conservative substitutions" are provided in Table B under the heading "Preferred Substitutions" and further described below in reference to amino acid side chain classes (1) to (6) Amino acid substitutions may be introduced into the molecule of interest and the products screened for a desired activity, e.g., retained/improved antigen binding, decreased immunogenicity, or improved ADCC or CDC.

TABLE B

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

In certain embodiments, antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in antigen binding molecules may be made in order to create variants with certain improved properties. In one aspect, variants of antigen binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of antigen binding molecules of the invention include those with bisected oligosaccharides, e.g., in which a biantennary oligosaccharide attached to the Fc region is bisected by GlcNAc. Such variants may have reduced fucosylation and/or improved ADCC function., see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the antigen binding molecule of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed. In another aspect, immunoconjugates of the antigen binding molecules provided herein maybe obtained. An "immunoconjugate" is an antibody conjugated to one or more heterologous molecule(s), including but not limited to a cytotoxic agent.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymomas, medulloblastomas, meningiomas, squamous cell carcinomas, pituitary adenoma and Ewings sarcoma, including refractory versions of any of the above cancers, or a combination of one or more of the above cancers.

Antibodies of the Invention

The invention provides novel anti-human CD19 antibodies with particularly advantageous properties such as producibility, stability, binding affinity, biological activity, targeting efficiency and reduced toxicity.

In one aspect, the invention provides anti-human CD19 antibodies with high affinity.

In one aspect, provided is an antibody, that specifically binds to human CD19 with a higher affinity than an antibody comprising a variable heavy chain comprising an amino acid sequence of SEQ ID NO:113 and a variable light chain comprising an amino acid sequence of SEQ ID NO:114.

In another aspect, provided is an antibody that specifically binds to human CD19, wherein the antibody comprises
   (a) CDR-L1 comprising the amino acid sequence of SEQ ID NO: 43,
   (b) CDR-L2 comprising the amino acid sequence of SEQ ID NO: 44,
   (c) CDR-L3 comprising the amino acid sequence of SEQ ID NO: 45, (d) CDR-H1 comprising the amino acid sequence of SEQ ID NO: 46, (e) CDR-H2 comprising the amino acid sequence of SEQ ID NO: 47, and (f) CDR-H3 comprising the amino acid sequence of SEQ ID NO: 48.

In one aspect, the antibody comprises (a) CDR-L1 comprising the amino acid sequence of SEQ ID NO: 43, (b) CDR-L2 comprising the amino acid sequence of SEQ ID NO: 44, (c) CDR-L3 comprising the amino acid sequence of SEQ ID NO: 45, (d) CDR-H1 comprising the amino acid sequence of SEQ ID NO: 46, (e) CDR-H2 comprising the amino acid sequence of SEQ ID NO: 47, and (f) CDR-H3 comprising the amino acid sequence of SEQ ID NO: 48, and specifically binds to human CD19 with a higher affinity than an antibody comprising a variable heavy chain comprising an amino acid sequence of SEQ ID NO:113 and a variable light chain comprising an amino acid sequence of SEQ ID NO:114.

In a further aspect, the antibody is a monoclonal antibody. In another aspect, the antibody is a human, humanized or chimeric antibody. In a further aspect, the antibody is a humanized antibody. In another aspect, the antibody is an antibody fragment that specifically binds to human CD19.

A further aspect of the present invention is the provision an antibody as disclosed herein that specifically binds to CD19. In a further aspect, the antibody as disclosed herein specifically binds to human CD19. In a further aspect, the antibody as disclosed herein specifically binds to cynomolgus CD19. In yet a further aspect, the antibodies as disclosed have cross species reactivity.

In certain aspects, the anti-CD19 antibody as disclosed herein has a equilibrium dissociation constant (Kd) of $\leq 1$ NM, $\leq 100$ nM, $\leq 10$ nM, $\leq 1$ nM, $\leq 0.1$ nM, $\leq 0.01$ nM, or $\leq 0.001$ nM, from $10^{-8}$ M to $10^{-13}$ M or from $10^{-9}$ M to $10^{-13}$ M. In a particular aspect, the antibody as disclosed herein binds to CD19 with an equilibrium dissociation constant (Kd) of 1 nM or less as determined by Surface Plasmon Resonance (SPR).

In yet a further aspect of the present invention, provided is an anti-CD19 antibody as disclosed herein with a dissociation constant (kd) of $\leq 10^{-2}$/s, $\leq 10^{-3}$/s, $\leq 10^{-4}$/s, $\leq 10^{-5}$/s, $\leq 10^{-6}$/s, $\leq 10^{-7}$/s, or $\leq 10^{-8}$/s, from $10^{-4}$/s to $10^{-9}$/s or from $10^{-5}$/s to $10^{-11}$/s. In a particular embodiment, the antibody as disclosed herein specifically binds to CD19 and is characterized further by an dissociation constant (kd) of $10^{-4}$/s or less as determined by Surface Plasmon Resonance (SPR).

In another aspect, provided is an antibody that specifically binds to CD19, wherein the antibody comprises less deamination sites compared to an antibody comprising a variable heavy chain comprising an amino acid sequence of SEQ ID NO:113 and a variable light chain comprising an amino acid sequence of SEQ ID NO:114. In another aspect, provided is an antibody that specifically binds to CD19, wherein the antibody comprises less asparagine residues compared to an antibody comprising a variable heavy chain comprising an amino acid sequence of SEQ ID NO:113 and a variable light chain comprising an amino acid sequence of SEQ ID NO:114.

In yet another aspect, provided is an antibody that comprises a variant variable light chain and/or a variant variable heavy chain comprising at least one amino acid substitution relative to an antibody comprising the variable heavy chain comprising an amino acid sequence of SEQ ID NO:113 and the variable light chain comprising an amino acid sequence of SEQ ID NO:114, wherein at least one asparagine residue is substituted. In preferred aspects, at least two, at least three or at least four asparagine residues are substituted.

In a particular aspect, provided is an antibody, wherein the antibody comprises a VH domain comprising an amino acid sequence of SEQ ID NO:99 and a VL domain comprising an amino acid sequence of SEQ ID NO:100.

In another aspect, provided is an antibody that specifically binds to human CD19, wherein the antibody is selected from the group consisting of (i) an antibody comprising a CDR-L1 comprising the amino acid sequence of SEQ ID NO: 25, a CDR-L2 comprising the amino acid sequence of SEQ ID NO: 26, a CDR-L3 comprising the amino acid sequence of SEQ ID NO: 27, a CDR-H1 comprising the amino acid sequence of SEQ ID NO: 28, a CDR-H2 comprising the amino acid sequence of SEQ ID NO: 29, and a CDR-H3 comprising the amino acid sequence of SEQ ID NO: 30, (ii) an antibody comprising a CDR-L1 comprising the amino acid sequence of SEQ ID NO: 31, a CDR-L2 comprising the amino acid sequence of SEQ ID NO: 32, a CDR-L3 comprising the amino acid sequence of SEQ ID NO: 33, a CDR-H1 comprising the amino acid sequence of SEQ ID NO: 34, a CDR-H2 comprising the amino acid sequence of SEQ ID NO: 35, and a CDR-H3 comprising the amino acid sequence of SEQ ID NO: 36, (iii) an antibody comprising a CDR-L1 comprising the amino acid sequence of SEQ ID NO: 37, a CDR-L2 comprising the amino acid sequence of SEQ ID NO: 38, a CDR-L3 comprising the amino acid sequence of SEQ ID NO: 39, a CDR-H1 comprising the amino acid sequence of SEQ ID NO: 40, a CDR-H2 comprising the amino acid sequence of SEQ ID NO: 41, and a CDR-H3 comprising the amino acid sequence of SEQ ID NO: 42, (iv) an antibody comprising a CDR-L1 comprising the amino acid sequence of SEQ ID NO: 43, a CDR-L2 comprising the amino acid sequence of SEQ ID NO: 44, a CDR-L3 comprising the amino acid sequence of SEQ ID NO: 45, a CDR-H1 comprising the amino acid sequence of SEQ ID NO: 46, a CDR-H2 comprising the amino acid sequence of SEQ ID NO: 47, and a CDR-H3 comprising the amino acid sequence of SEQ ID NO: 48, (v) an antibody comprising a CDR-L1 comprising the amino acid sequence of SEQ ID NO: 49, a CDR-L2 comprising the amino acid sequence of SEQ ID NO: 50, a CDR-L3 comprising the amino acid sequence of SEQ ID NO: 51, a CDR-H1 comprising the amino acid sequence of SEQ ID NO: 52, a CDR-H2 comprising the amino acid sequence of SEQ ID NO: 53, and a CDR-H3 comprising the amino acid sequence of SEQ ID NO: 54, (vi) an antibody comprising a CDR-L1 comprising the amino acid sequence of SEQ ID NO: 55, a CDR-L2 comprising the amino acid sequence of SEQ ID NO: 56, a CDR-L3 comprising the amino acid sequence of SEQ ID NO: 57, a CDR-H1 comprising the amino acid sequence of SEQ ID NO: 58, a CDR-H2 comprising the amino acid sequence of SEQ ID NO: 59, and a CDR-H3 comprising the amino acid sequence of SEQ ID NO: 60, and (vii) an antibody comprising a CDR-L1 comprising the amino acid sequence of SEQ ID NO: 61, a CDR-L2 comprising the amino acid sequence of SEQ ID NO: 62, a CDR-L3 comprising the amino acid sequence of SEQ ID NO: 63, a CDR-H1 comprising the amino acid sequence of SEQ ID NO: 64, a CDR-H2 comprising the amino acid sequence of SEQ ID NO: 65, and a CDR-H3 comprising the amino acid sequence of SEQ ID NO: 66.

In a further aspect, provided is an antibody that specifically binds to CD19, wherein the antibody comprises (i) a VH domain comprising an amino acid sequence of SEQ ID NO:111 and a VL domain comprising an amino acid sequence of SEQ ID NO:112, (ii) a VH domain comprising an amino acid sequence of SEQ ID NO:101 and a VL domain comprising an amino acid sequence of SEQ ID NO:102, (iii) a VH domain comprising an amino acid sequence of SEQ ID NO:103 and a VL domain comprising an amino acid sequence of SEQ ID NO:104, (iv) a VH domain comprising an amino acid sequence of SEQ ID NO:99 and a VL domain comprising an amino acid sequence of SEQ ID NO:100, (v) a VH domain comprising an amino acid sequence of SEQ ID NO:105 and a VL domain comprising an amino acid sequence of SEQ ID NO:106, (vi) a VH domain comprising an amino acid sequence of SEQ ID NO:107 and a VL domain comprising an amino acid sequence of SEQ ID NO:108, or (vii) a VH domain comprising an amino acid sequence of SEQ ID NO:109 and a VL domain comprising an amino acid sequence of SEQ ID NO:110.

In another aspect, the antibody as defined herein before comprises an Fc domain composed of a first and a second subunit capable of stable association.

In a further aspect, the Fc domain is an IgG, particularly an IgG1 Fc domain or an IgG4 Fc domain. More particularly, the Fc domain is an IgG1 Fc domain. In a particular aspect, the Fc domain comprises a modification promoting the association of the first and second subunit of the Fc domain.

Fc Domain Modifications Reducing Fc Receptor Binding and/or Effector Function The Fc domain of the antigen binding molecules of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

The Fc domain confers favorable pharmacokinetic properties to the antigen binding molecules of the invention, including a long serum half-life which contributes to good accumulation in the target tissue and a favorable tissue-blood distribution ratio. At the same time it may, however, lead to undesirable targeting of the antibodies of the invention to cells expressing Fc receptors rather than to the preferred antigen-bearing cells. Accordingly, in particular aspects, the Fc domain of the antigen binding molecule of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In a particular aspect, the invention provides an antibody, wherein the Fc domain comprises one or more amino acid substitution that reduces binding to an Fc receptor, in particular towards Fcγ receptor.

In one aspect, the Fc domain of the antibody of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is an antibody according to the invention which comprises an Fc domain with the amino acid substitutions L234A, L235A and P329G ("P329G LALA", EU numbering) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position S228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

In another aspect, provided is an antibody that specifically binds to human CD19, wherein the antibody comprises (a) CDR-L1 comprising the amino acid sequence of SEQ ID NO: 43, (b) CDR-L2 comprising the amino acid sequence of SEQ ID NO: 44, (c) CDR-L3 comprising the amino acid sequence of SEQ ID NO: 45, (d) CDR-H1 comprising the amino acid sequence of SEQ ID NO: 46, (e) CDR-H2 comprising the amino acid sequence of SEQ ID NO: 47, and (f) CDR-H3 comprising the amino acid sequence of SEQ ID NO: 48, and wherein the antibody comprises an Fc domain with the amino acid residues 234A, 235A and 329G (EU numbering) in the IgG heavy chains.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g., by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or cell activating antibodies comprising an Fc domain for Fc receptors may be evaluated using cell lines known to express particular Fc receptors, such as human NK cells expressing FcγIIIa receptor.

Effector function of an Fc domain, or antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assay methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc Natl Acad Sci USA 95, 652-656 (1998).

In some aspects, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the bispecific antibodies of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Polynucleotides

The invention further provides isolated polynucleotides encoding an antibody as described herein or a fragment thereof.

The isolated polynucleotides encoding the antibodies of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated polynucleotide encodes the entire antibody according to the invention as described herein. In other embodiments, the isolated polynucleotide encodes a polypeptide comprised in the antibody according to the invention as described herein.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Antibodies of the invention may be obtained, for example, by solid-state peptide synthesis (e.g. Merrifield solid phase synthesis) or recombinant production. For recombinant production one or more polynucleotide encoding the antibody or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the antibody (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOL-OGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the antibody or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g., promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody or polypeptide fragments thereof is desired, DNA encoding a signal sequence may be placed upstream of the nucleic acid an antibody of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding an antibody of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g., has been transformed or transfected with) a vector comprising a polynucleotide that encodes (part of) an antibody of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040, 498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr-CHO cells (Urlaub et al., Proc Natl Acad Sci USA 77, 4216 (1980)); and myeloma cell lines such as Y0, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing an antibody of the invention or polypeptide fragments thereof is provided, wherein the method comprises culturing a host cell comprising polynucleotides encoding the antibody of the invention or polypeptide fragments thereof, as provided herein, under conditions suitable for expression of the antibody of the invention or polypeptide fragments thereof, and recovering the antibody of the invention or polypeptide fragments thereof from the host cell (or host cell culture medium).

In certain embodiments the moieties capable of specific binding to a target cell antigen (e.g. Fab fragments) forming part of the antigen binding molecule comprise at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g., as described in U.S. Pat. No. 4,186,567) or can be obtained, for example, by screening combinatorial libraries comprising variable heavy chains and variable light chains (see e.g., U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e.g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g., Lonberg, Nat Biotech 23, 1117-1125 (2005)). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N J, 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the antibodies are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g., surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, NJ). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch.14 (Cold Spring Harbor Laboratory, Cold Spring Harbor, NY).

Antibodies of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the TNF ligand trimer-containing antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the TNF ligand trimer-containing antigen binding molecule or fragments thereof can be determined by any of a variety of well-known analytical methods including gel electrophoresis, high pressure liquid chromatography, and the like. For example, the antigen binding molecules expressed as described in the Examples were shown to be intact and properly assembled as demonstrated by reducing and non-reducing SDS-PAGE.

Assays

The antigen binding molecules provided herein may be identified, screened for, or characterized for their physical/chemical properties and/or biological activities by various assays known in the art.

1. Affinity Assays

The affinity of the antigen binding molecule for the target cell antigen can also be determined by surface plasmon resonance (SPR), using standard instrumentation such as a BIAcore instrument (GE Healthcare), and receptors or target proteins such as may be obtained by recombinant expression. A specific illustrative and exemplary embodiment for measuring binding affinity is described in Example 4.

According to one aspect, $K_D$ is measured by surface plasmon resonance using a BIACORE® T100 machine (GE Healthcare) at 25° C.

2. Binding Assays and Other Assays

In one aspect, an antibody as reported herein is tested for its antigen binding activity, e.g., by known methods such as ELISA or Western blot.

3. Activity Assays

In one aspect, assays are provided for identifying anti-human CD19 antibodies thereof having biological activity. Biological activity may include, e.g., inhibition of B-cell proliferation or killing of B-cells. Antibodies having such biological activity in vivo and/or in vitro are also provided.

In certain embodiments, an antibody as reported herein is tested for such biological activity.

Pharmaceutical Compositions, Formulations and Routes of Administration

In a further aspect, the invention provides pharmaceutical compositions comprising any of the antibodies provided herein, e.g., for use in any of the below therapeutic methods. In one embodiment, a pharmaceutical composition comprises an antibody provided herein and at least one pharmaceutically acceptable excipient. In another embodiment, a pharmaceutical composition comprises an antibody provided herein and at least one additional therapeutic agent, e.g., as described below.

Pharmaceutical compositions of the present invention comprise a therapeutically effective amount of one or more antibodies dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one antibody and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g., antibacterial agents, antifungal agents), isotonic agents, salts, stabilizers and combinations thereof, as would be known to one of ordinary skill in the art.

Parenteral compositions include those designed for administration by injection, e.g., subcutaneous, intradermal, intralesional, intravenous, intraarterial intramuscular, intrathecal or intraperitoneal injection. For injection, the antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer.

In addition to the compositions described previously, the fusion proteins may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the fusion proteins of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The antibody of the invention may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

Therapeutic Methods and Compositions

Any of the anti-human CD19 antibodies provided herein may be used in therapeutic methods, either alone or in combination, either as monospecific antibody or as multispecific antibody.

CD19 is expressed on most B-cells (pan-B-cell marker) with the exception of stem cells and plasma cells, and is frequently expressed on most human B-cell malignancies (tumor associated antigen), such as lymphoma and leukemias except for multiple myeloma, e.g. in non-Hodgkin lymphoma and acute lymphoblastic leukemia.

Bispecific antibodies recognizing two cell surface proteins on different cell populations hold the promise to redirect cytotoxic immune cells for destruction of pathogenic target cells.

In one aspect, an anti-human CD19 antibody for use as a medicament is provided. In further aspects, an anti-human CD19 antibody for use in treating a B-cell cancer is provided. In certain embodiments, an anti-human CD19 antibody for use in a method of treatment is provided. In certain embodiments, herein is provided an anti-human CD19 antibody for use in a method of treating an individual having a B-cell cancer comprising administering to the individual an effective amount of the anti-human CD19 antibody. In one such embodiment, the method further comprises administering to the individual an effective amount of at least one additional therapeutic agent. In further embodiments, herein is provided an anti-human CD19 antibody for use in depleting B-cells. In certain embodiments, herein is provided an anti-human CD19 antibody for use in a method of depleting B-cells in an individual comprising administering to the individual an effective amount of the anti-human CD19 antibody to deplete B-cells. An "individual" according to any of the above embodiments is preferably a human. The B-cell cancer is in one embodiment a B-cell lymphoma or a B-cell leukemia. In one embodiment the B-cell cancer is non-Hodgkin lymphoma or acute lymphoblastic leukemia.

In further aspects, an anti-human CD19 antibody for use in cancer immunotherapy is provided. In certain embodiments, an anti-human CD19 antibody for use in a method of cancer immunotherapy is provided. An "individual" according to any of the above embodiments is preferably a human.

In a further aspect, herein is provided for the use of an anti-human CD19 antibody in the manufacture or preparation of a medicament. In one embodiment, the medicament is for treatment of a B-cell cancer. In a further embodiment, the medicament is for use in a method of treating a B-cell cancer comprising administering to an individual having a B-cell cancer an effective amount of the medicament. In one such embodiment, the method further comprises administering to the individual an effective amount of at least one additional therapeutic agent, e.g., as described below. In a further embodiment, the medicament is for depleting B-cells. In a further embodiment, the medicament is for use in a method of depleting B-cells in an individual comprising administering to the individual an amount effective of the medicament to deplete B-cells. An "individual" according to any of the above embodiments may be a human. The B-cell cancer is in one embodiment a B-cell lymphoma or a B-cell leukemia. In one embodiment the B-cell cancer is non-Hodgkin lymphoma or acute lymphoblastic leukemia.

In a further aspect, herein is provided a method for treating a B-cell cancer. In one embodiment, the method comprises administering to an individual having such B-cell cancer an effective amount of an anti-human CD19 antibody. In one such embodiment, the method further comprises administering to the individual an effective amount of at least one additional therapeutic agent, as described below. An "individual" according to any of the above embodiments may be a human. The B-cell cancer is in one embodiment a B-cell lymphoma or a B-cell leukemia. In one embodiment the B-cell cancer is non-Hodgkin lymphoma or acute lymphoblastic leukemia.

In a further aspect, herein is provided a method for depleting B-cells in an individual. In one embodiment, the method comprises administering to the individual an effective amount of an anti-human CD19 antibody to deplete B-cells. In one embodiment, an "individual" is a human. The B-cell cancer is in one embodiment a B-cell lymphoma or a B-cell leukemia. In one embodiment the B-cell cancer is non-Hodgkin lymphoma or acute lymphoblastic leukemia.

In a further aspect, herein is provided pharmaceutical formulations comprising any of the anti-human CD19 antibodies as reported herein, e.g., for use in any of the above therapeutic methods. In one embodiment, a pharmaceutical formulation comprises any of the anti-human CD19 antibodies as reported herein and a pharmaceutically acceptable carrier. In another embodiment, a pharmaceutical formulation comprises any of the anti-human CD19 antibodies as reported herein and at least one additional therapeutic agent.

Antibodies as reported herein can be used either alone or in combination with other agents in a therapy. For instance, an antibody as reported herein may be co-administered with at least one additional therapeutic agent.

Such combination therapies noted above encompass combined administration (where two or more therapeutic agents are included in the same or separate formulations), and separate administration, in which case, administration of the antibody as reported herein can occur prior to, simultaneously, and/or following, administration of the additional therapeutic agent or agents. In one embodiment, administration of the anti-human CD19 antibody and administration of an additional therapeutic agent occur within about one month, or within about one, two or three weeks, or within about one, two, three, four, five, or six days, of each other.

An antibody as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody as reported herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Herein are further provided methods for treating an inflammatory disease, an autoimmune disease, rheumatoid arthritis, lupus, psoriasis, and a bone disease, comprising administering to a patient diagnosed as having such disease (and therefore being in need of such a therapy) an antibody specifically binding to human CD19 as reported herein. The antibody may be administered alone, in a pharmaceutical composition, or alternatively in combination with other medicaments for treating an inflammatory disease, an autoimmune disease, rheumatoid arthritis, lupus, psoriasis, or a bone disease. The antibody is administered in a pharmaceutically effective amount.

Herein is further provided the use of an antibody as reported herein for the treatment of an inflammatory disease, an autoimmune disease, rheumatoid arthritis, lupus, psoriasis or a bone disease, and for the manufacture of a pharmaceutical composition comprising an antibody as reported herein. In addition, herein is provided a method for the manufacture of a pharmaceutical composition comprising an antibody as reported herein.

Herein is further provided an antibody as reported herein for the treatment of an inflammatory disease, an autoimmune disease, rheumatoid arthritis, lupus, psoriasis, or a bone disease.

Further provided herein is the use of an antibody as reported herein for the manufacture of a pharmaceutical composition for the treatment of an inflammatory disease, an autoimmune disease, rheumatoid arthritis, lupus, psoriasis, or a bone disease. The antibody is used in a pharmaceutically effective amount.

Further provided herein is the use of an antibody as reported herein for the manufacture of a pharmaceutical composition for the treatment of an inflammatory disease, an autoimmune disease, rheumatoid arthritis, lupus, psoriasis, or a bone disease. The antibody is used in a pharmaceutically effective amount.

It is understood that any of the above formulations or therapeutic methods may be carried out using an immunoconjugate as reported herein in place of or in addition to an anti-human CD19 antibody.

Other Agents and Treatments

The antigen binding molecules of the invention may be administered in combination with one or more other agents in therapy. For instance, an antigen binding molecule of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

Such other agents are suitably present in combination in amounts that are effective for the purpose intended. The effective amount of such other agents depends on the amount of the antigen binding molecules used, the type of disorder or treatment, and other factors discussed above. The antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antigen binding molecule of the invention can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a TNF ligand trimer-containing antigen binding molecule of the invention.

The label or package insert indicates that the composition is used for treating the condition of choice. Moreover, the article of manufacture may comprise (a) a first container with a composition contained therein, wherein the composition comprises an antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE C

| | | (Sequences): |
|---|---|---|

| SEQ ID NO: | Name | Sequence |
|---|---|---|
| 1 | human CD19 ectodomain | UniProt no. P15391, AA |
| 2 | cynomolgus CD19 ectodomain | AA |
| 3 | Nucleotide sequence of Fc hole chain | see Table 2 |
| 4 | Nucleotide sequence of human CD19 antigen Fc knob chain avi tag | see Table 2 |
| 5 | Fc hole chain | see Table 2 |
| 6 | human CD19 antigen Fc knob chain avi tag | see Table 2 |
| 7 | Nucleotide sequence of cynomolgus CD19 antigen Fc knob chain avi tag | see Table 2 |
| 8 | cynomolgus CD19 antigen Fc knob chain avi tag | see Table 2 |
| 9 | Nucleotide sequence of CD19 (8B8) VH Parental clone | CAAGTTCAATTGGTTCAATCTGGTGCTGAACT AAAAAAACCGGGCGCTTCCGTTAAAGTGAGCT GCAAAGCATCTGGTTACACCTTCACTGACTAT ATCATGCACTGGGTTCGTCAGGCCCCGGGCCA GGGTCTGGAGTGGATGGGCTACATTAACCCAT ACAACGACGGTTCCAAATATACCGAGAAATTC CAGGGCCGCGTCACGATGACCAGCGACACTTC TATCTCCACCGCGTACATGGAACTGTCTAGAC TGCGTTCTGACGACACCGCTGTTTACTATTGTG CACGCGGTACTTACTACTACGGTTCCGCCCTCT TTGATTACTGGGGCCAAGGTACCACGGTGACC GTAAGCTCT |
| 10 | Nucleotide sequence of CD19 (8B8) VL Parental clone | GATATTGTTATGACTCAAACTCCACTGTCTCTG TCCGTGACCCCGGGTCAGCCAGCGAGCATTTC TTGCAAATCCAGCCAATCTCTGGAAAACTCCA ACGGCAACACGTACCTGAACTGGTATCTCCAG AAACCGGGTCAGAGCCCGCAGCTGCTGATCTA CCGTGTATCTAAGCGCTTCTCCGGCGTTCCTGA TCGTTTCAGCGGTTCTGGATCCGGCACCGACT TTACTCTGAAAATCAGCCGTGTGGAAGCTGAA GACGTTGGCGTCTACTATTGTCTGCAGTTGAC CCACGTTCCGTACACCTTCGGTCAAGGAACTA AACTGGAAATTAAA |
| 11 | CD19 L1 reverse random | see Table 4 |
| 12 | CD19 L2 forward random | see Table 4 |
| 13 | CD19 H1 reverse random | see Table 4 |
| 14 | CD19 H2 forward random | see Table 4 |
| 15 | CD19 H3 reverse constant | see Table 4 |
| 16 | LMB3 | see Table 4 |
| 17 | CD19 L1 forward constant | see Table 5 |
| 18 | CD19 L3 reverse random | see Table 5 |
| 19 | CD19 L3 forward constant | see Table 5 |
| 20 | CD19 H3 reverse random | see Table 5 |
| 21 | Nucleotide sequence of SNAP tag human CD19 ECD-PDGFR | GGCCGCCGCTAGCGGCATCGACTACAAGGACGAC GATGACAAGGCCGGCATCGATGCCATCATGGACA AAGACTGCGAAATGAAGCGCACCACCCTGGATAG CCCTCTGGGCAAGCTGGAACTGTCTGGGTGCGAAC AGGGCCTGCACGAGATCAAGCTGCTGGGCAAAGG AACATCTGCCGCCGACGCCGTGGAAGTGCCTGCCC |

TABLE C-continued

| (Sequences): | | |
|---|---|---|
| SEQ ID NO: | Name | Sequence |

| | | CAGCCGCCGTGCTGGGCGGACCAGAGCCACTGAT |
| | | GCAGGCCACCGCCTGGCTCAACGCCTACTTTCACC |
| | | AGCCTGAGGCCATCGAGGAGTTCCCTGTGCCAGCC |
| | | CTGCACCACCCAGTGTTCCAGCAGGAGAGCTTTAC |
| | | CCGCCAGGTGCTGTGGAAACTGCTGAAAGTGGTGA |
| | | AGTTCGGAGAGGTCATCAGCTACCAGCAGCTGGCC |
| | | GCCCTGGCCGGCAATCCCGCCGCCACCGCCGCCGT |
| | | GAAAACCGCCCTGAGCGGAAATCCCGTGCCCATTC |
| | | TGATCCCCTGCCACCGGGTGGTGTCTAGCTCTGGC |
| | | GCCGTGGGGGGCTACGAGGGCGGGCTCGCCGTGA |
| | | AAGAGTGGCTGCTGGCCCACGAGGGCCACAGACT |
| | | GGGCAAGCCTGGGCTGGGTGATATCCCCGAGGAA |
| | | CCCCTGGTCGTGAAGGTGGAAGAGGGCGACAATG |
| | | CCGTGCTGCAGTGCCTGAAGGGCACCTCCGATGGC |
| | | CCTACCCAGCAGCTGACCTGGTCCAGAGAGAGCCC |
| | | CCTGAAGCCCTTCCTGAAGCTGTCTCTGGGCCTGC |
| | | CTGGCCTGGGCATCCATATGAGGCCTCTGGCCATC |
| | | TGGCTGTTCATCTTCAACGTGTCCCAGCAGATGGG |
| | | CGGCTTCTACCTGTGTCAGCCTGGCCCCCCCATCTG |
| | | AGAAGGCTTGGCAGCCTGGCTGGACCGTGAACGT |
| | | GGAAGGATCCGGCGAGCTGTTCCGGTGGAACGTGT |
| | | CCGATCTGGGCGGCCTGGGATGCGGCCTGAAGAA |
| | | CAGATCTAGCGAGGGCCCCAGCAGCCCCAGCGGC |
| | | AAACTGATGAGCCCCAAGCTGTACGTGTGGGCCAA |
| | | GGACAGACCCGAGATCTGGGAGGGCGAGCCTCCT |
| | | TGCCTGCCCCCTAGAGACAGCCTGAACCAGAGCCT |
| | | GAGCCAGGACCTGACAATGGCCCCTGGCAGCACA |
| | | CTGTGGCTGAGCTGTGGCGTGCCCACCCGACTCTGT |
| | | GTCTAGAGGCCCTCTGAGCTGGACCCACGTGCACC |
| | | CTAAGGGCCCTAAGAGCCTGCTGAGCCTGGAACTG |
| | | AAGGACGACAGGCCCGCCAGAGATATGTGGGTCA |
| | | TGGAAACCGGCCTGCTGCTGCCTAGAGCCACAGCC |
| | | CAGGATGCCGGCAAGTACTACTGCCACAGAGGCA |
| | | ACCTGACCATGAGCTTCCACCTGGAAATCACCGCC |
| | | AGACCCGTGCTGTGGCACTGGCTGCTGAGAACAGG |
| | | CGGCTGGAAGGTCGACGAACAAAAACTCATCTCA |
| | | GAAGAGGATCTGAATGCTGTGGGCCAGGACACGC |
| | | AGGAGGTCATCGTGGTGCCACACTCCTTGCCCTTT |
| | | AAGGTGGTGGTGATCTCAGCCATCCTGGCCCTGGT |
| | | GGTGCTCACCATCATCTCCCTTATCATCCTCATCAT |
| | | GCTTTGGCAGAAGAAGCCACGT |
| 22 | Nucleotide sequence of SNAP tag cynomolgus CD19 ECD-PDGFR | CCGGCCGCCGCTAGCGGCATCGACTACAAGGACG |
| | | ACGATGACAAGGCCGGCATCGATGCCATCATGGA |
| | | CAAAGACTGCGAAATGAAGCGCACCACCCTGGAT |
| | | AGCCCTCTGGGCAAGCTGGAACTGTCTGGGTGCGA |
| | | ACAGGGCCTGCACGAGATCAAGCTGCTGGGCAAA |
| | | GGAACATCTGCCGCCGACGCCGTGGAAGTGCCTGC |
| | | CCCAGCCGCCGTGCTGGGCGGACCAGAGCCACTG |
| | | ATGCAGGCCACCGCCTGGCTCAACGCCTACTTTCA |
| | | CCAGCCTGAGGCCATCGAGGAGTTCCCTGTGCCAG |
| | | CCCTGCACCACCCAGTGTTCCAGCAGGAGAGCTTT |
| | | ACCCGCCAGGTGCTGTGGAAACTGCTGAAAGTGGT |
| | | GAAGTTCGGAGAGGTCATCAGCTACCAGCAGCTG |
| | | GCCGCCCTGGCCGGCAATCCCGCCGCCACCGCCGC |
| | | CGTGAAAACCGCCCTGAGCGGAAATCCCGTGCCCA |
| | | TTCTGATCCCCTGCCACCGGGTGGTGTCTAGCTCTG |
| | | GCGCCGTGGGGGGCTACGAGGGCGGGCTCGCCGT |
| | | GAAAGAGTGGCTGCTGGCCCACGAGGGCCACAGA |
| | | CTGGGCAAGCCTGGGCTGGGTGATATCCCCCAGGA |
| | | ACCCCTGGTCGTGAAGGTGGAAGAGGGCGACAAT |
| | | GCCGTGCTCCAGTGTCTCGAGGGCACCTCCGATGG |
| | | CCCTACACAGCAGCTCGTGTGGTGCAGAGACAGCC |
| | | CCTTCGAGCCCTTCCTGAACCTGTCTCTGGGCCTGC |
| | | CTGGCATGGGCATCAGAATGGGCCCTCTGGGCATC |
| | | TGGCTGCTGATCTTCAACGTGTCCAACCAGACCGG |
| | | CGGCTTCTACCTGTGTCAGCCTGGCCTGCCAAGCG |
| | | AGAAGGCTTGGCAGCCTGGATGGACCGTGTCCGTG |
| | | GAAGGATCTGGCGAGCTGTTCCGGTGGAACGTGTC |
| | | CGATCTGGGCGGCCTGGGATGCGGCCTGAAGAAC |
| | | AGAAGCAGCGAGGGCCCCTAGCAGCCCCAGCGGCA |
| | | AGCTGAATAGCAGCCAGCTGTACGTGTGGGCCAA |
| | | GGACAGACCCGAGATGTGGGAGGGCGAGCCTGTG |
| | | TGTGGCCCCCCTAGAGATAGCCTGAACCAGAGCCT |
| | | GAGCCAGGACCTGACAATGGCCCCTGGCAGCACA |

TABLE C-continued (Sequences):

| SEQ ID NO: | Name | Sequence |
|---|---|---|
| | | CTGTGGCTGAGCTGTGGCGTGCCACCCGACTCTGT<br>GTCCAGAGGCCCTCTGAGCTGGACACACGTGCGGC<br>CTAAGGGCCCTAAGAGCAGCCTGCTGAGCCTGGA<br>ACTGAAGGACGACCGGCCCGACCGGGATATGTGG<br>GTGGTGGATACAGGCCTGCTGCTGACCAGAGCCAC<br>AGCCCAGGATGCCGGCAAGTACTACTGCCACAGA<br>GGCAACTGGACCAAGAGCTTTTACCTGGAAATCAC<br>CGCCAGACCCGCCCTGTGGCACTGGCTGCTGAGAA<br>TCGGAGGCTGGAAGGTCGACGAGCAGAAGCTGAT<br>CTCCGAAGAGGACCTGAACGCCGTGGGCCAGGAT<br>ACCCAGGAAGTGATCGTGGTGCCCCACAGCCTGCC<br>CTTCAAGGTGGTCGTGATCAGCGCCATTCTGGCCC<br>TGGTGGTGCTGACCATCATCAGCCTGATCATCCTG<br>ATTATGCTGTGGCAGAAAAAGCCCCGC |
| 23 | SNAP tag human CD19 ECD-PDGFR | PAAASGIDYKDDDDKAGIDAIMDKDCEMKRTTLDSP<br>LGKLELSGCEQGLHEIKLLGKGTSAADAVEVPAPAA<br>VLGGPEPLMQATAWLNAYFHQPEAIEEFPVPALHHP<br>VFQQESFTRQVLWKLLKVVKFGEVISYQQLAALAGN<br>PAATAAVKTALSGNPVPILIPCHRVVSSSGAVGGYEG<br>GLAVKEWLLAHEGHRLGKPGLGDIPEEPLVVKVEEG<br>DNAVLQCLKGTSDGPTQQLTWSRESPLKPFLKLSLG<br>LPGLGIHMRPLAIWLFIFNVSQQMGGFYLCQPGPPSE<br>KAWQPGWTVNVEGSGELFRWNVSDLGGLGCGLKN<br>RSSEGPSSPSGKLMSPKLYVWAKDRPEIWEGEPPCLP<br>PRDSLNQSLSQDLTMAPGSTLWLSCGVPPDSVSRGPL<br>SWTHVHPKGPKSLLSLELKDDRPARDMWVMETGLL<br>LPRATAQDAGKYYCHRGNLTMSFHLEITARPVLWH<br>WLLRTGGWKVDEQKLISEEDLNAVGQDTQEVIVVP<br>HSLPFKVVVISAILALVVLTIISLIILIMLWQKKPR |
| 24 | SNAP tag cynomolgus CD19 ECD-PDGFR | PAAASGIDYKDDDDKAGIDAIMDKDCEMKRTTLDSP<br>LGKLELSGCEQGLHEIKLLGKGTSAADAVEVPAPAA<br>VLGGPEPLMQATAWLNAYFHQPEAIEEFPVPALHHP<br>VFQQESFTRQVLWKLLKVVKFGEVISYQQLAALAGN<br>PAATAAVKTALSGNPVPILIPCHRVVSSSGAVGGYEG<br>GLAVKEWLLAHEGHRLGKPGLGDIPQEPLVVKVEEG<br>DNAVLQCLEGTSDGPTQQLVWCRDSPFEPFLNLSLG<br>LPGMGIRMGPLGIWLLIFNVSNQTGGFYLCQPGLPSE<br>KAWQPGWTVSVEGSGELFRWNVSDLGGLGCGLKN<br>RSSEGPSSPSGKLNSSQLYVWAKDRPEMWEGEPVCG<br>PPRDSLNQSLSQDLTMAPGSTLWLSCGVPPDSVSRGP<br>LSWTHVRPKGPKSSLLSLELKDDRPDRDMWVVDTG<br>LLLTRATAQDAGKYYCHRGNWTKSFYLEITARPAL<br>WHWLLRIGGWKVDEQKLISEEDLNAVGQDTQEVIV<br>VPHSLPFKVVVISAILALVVLTIISLIILIMLWQKKPR |
| 25 | CD19 (8B8-5H09) CDR-L1 | see Table 7 |
| 26 | CD19 (8B8-5H09) CDR-L2 | see Table 7 |
| 27 | CD19 (8B8-5H09) CDR-L3 | see Table 7 |
| 28 | CD19 (8B8-5H09) CDR-H1 | see Table 8 |
| 29 | CD19 (8B8-5H09) CDR-H2 | see Table 8 |
| 30 | CD19 (8B8-5H09) CDR-H3 | see Table 8 |
| 31 | CD19 (8B8-7H07) CDR-L1 | see Table 7 |
| 32 | CD19 (8B8-7H07) CDR-L2 | see Table 7 |
| 33 | CD19 (8B8-7H07) CDR-L3 | see Table 7 |
| 34 | CD19 (8B8-7H07) CDR-H1 | see Table 8 |
| 35 | CD19 (8B8-7H07) CDR-H2 | see Table 8 |
| 36 | CD19 (8B8-7H07) CDR-H3 | see Table 8 |
| 37 | CD19 (8B8-2B03) CDR-L1 | see Table 7 |
| 38 | CD19 (8B8-2B03) CDR-L2 | see Table 7 |

TABLE C-continued

| | (Sequences): | |
|---|---|---|
| SEQ ID NO: | Name | Sequence |
| 39 | CD19 (8B8-2B03) CDR-L3 | see Table 7 |
| 40 | CD19 (8B8-2B03) CDR-H1 | see Table 8 |
| 41 | CD19 (8B8-2B03) CDR-H2 | see Table 8 |
| 42 | CD19 (8B8-2B03) CDR-H3 | see Table 8 |
| 43 | CD19 (8B8-2B11) CDR-L1 | see Table 7 |
| 44 | CD19 (8B8-2B11) CDR-L2 | see Table 7 |
| 45 | CD19 (8B8-2B11) CDR-L3 | see Table 7 |
| 46 | CD19 (8B8-2B11) CDR-H1 | see Table 8 |
| 47 | CD19 (8B8-2B11) CDR-H2 | see Table 8 |
| 48 | CD19 (8B8-2B11) CDR-H3 | see Table 8 |
| 49 | CD19 (8B8-5A07) CDR-L1 | see Table 7 |
| 50 | CD19 (8B8-5A07) CDR-L2 | see Table 7 |
| 51 | CD19 (8B8-5A07) CDR-L3 | see Table 7 |
| 52 | CD19 (8B8-5A07) CDR-H1 | see Table 8 |
| 53 | CD19 (8B8-5A07) CDR-H2 | see Table 8 |
| 54 | CD19 (8B8-5A07) CDR-H3 | see Table 8 |
| 55 | CD19 (8B8-5B08) CDR-L1 | see Table 7 |
| 56 | CD19 (8B8-5B08) CDR-L2 | see Table 7 |
| 57 | CD19 (8B8-5B08) CDR-L3 | see Table 7 |
| 58 | CD19 (8B8-5B08) CDR-H1 | see Table 8 |
| 59 | CD19 (8B8-5B08) CDR-H2 | see Table 8 |
| 60 | CD19 (8B8-5B08) CDR-H3 | see Table 8 |
| 61 | CD19 (8B8-5D08) CDR-L1 | see Table 7 |
| 62 | CD19 (8B8-5D08) CDR-L2 | see Table 7 |
| 63 | CD19 (8B8-5D08) CDR-L3 | see Table 7 |
| 64 | CD19 (8B8-5D08) CDR-H1 | see Table 8 |
| 65 | CD19 (8B8-5D08) CDR-H2 | see Table 8 |
| 66 | CD19 (8B8-5D08) CDR-H3 | see Table 8 |
| 67 | nucleotide sequence of CD19 (8B8) parental light chain | see Table 9 |
| 68 | nucleotide sequence of CD19 (8B8) parental heavy chain | see Table 9 |
| 69 | CD19 (8B8) parental light chain | see Table 9 |
| 70 | CD19 (8B8) parental heavy chain | see Table 9 |
| 71 | nucleotide sequence of CD19 (8B8-2B11) light chain | see Table 10 |

TABLE C-continued

| (Sequences): | | |
| --- | --- | --- |

| SEQ ID NO: | Name | Sequence |
| --- | --- | --- |
| 72 | nucleotide sequence of CD19 (8B8-2B11) heavy chain | see Table 10 |
| 73 | CD19 (8B8-2B11) light chain | see Table 10 |
| 74 | CD19 (8B8-2B11) heavy chain | see Table 10 |
| 75 | nucleotide sequence of CD19 (8B8-7H07) light chain | see Table 10 |
| 76 | nucleotide sequence of CD19 (8B8-7H07) heavy chain | see Table 10 |
| 77 | CD19 (8B8-7H07) light chain | see Table 10 |
| 78 | CD19 (8B8-7H07) heavy chain | see Table 10 |
| 79 | nucleotide sequence of CD19 (8B8-2B03) light chain | see Table 10 |
| 80 | nucleotide sequence of CD19 (8B8-2B03) heavy chain | see Table 10 |
| 81 | CD19 (8B8-2B03) light chain | see Table 10 |
| 82 | CD19 (8B8-2B03) heavy chain | see Table 10 |
| 83 | nucleotide sequence of CD19 (8B8-5A07) light chain | see Table 10 |
| 84 | nucleotide sequence of CD19 (8B8-5A07) heavy chain | see Table 10 |
| 85 | CD19 (8B8-5A07) light chain | see Table 10 |
| 86 | CD19 (8B8-5A07) heavy chain | see Table 10 |
| 87 | nucleotide sequence of CD19 (8B8-5D08) light chain | see Table 10 |
| 88 | nucleotide sequence of CD19 (8B8-5D08) heavy chain | see Table 10 |
| 89 | CD19 (8B8-5D08) light chain | see Table 10 |
| 90 | CD19 (8B8-5D08) heavy chain | see Table 10 |
| 91 | nucleotide sequence of CD19 (8B8-5B08) light chain | see Table 10 |
| 92 | nucleotide sequence of CD19 (8B8-5B08) heavy chain | see Table 10 |

TABLE C-continued

| | (Sequences): | |
|---|---|---|
| SEQ ID NO: | Name | Sequence |
| 93 | CD19 (8B8-5B08) light chain | see Table 10 |
| 94 | CD19 (8B8-5B08) heavy chain | see Table 10 |
| 95 | nucleotide sequence of CD19 (8B8-5H09) light chain | see Table 10 |
| 96 | nucleotide sequence of CD19 (8B8-5H09) heavy chain | see Table 10 |
| 97 | CD19 (8B8-5H09) light chain | see Table 10 |
| 98 | CD19 (8B8-5H09) heavy chain | see Table 10 |
| 99 | CD19 (8B8-2B11) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSS |
| 100 | CD19 (8B8-2B11) VL | DIVMTQTPLSLSVTPGQPASISCKSSQSLETSTGTTYL NWYLQKPGQSPQLLIYRVSKRFSGVPDRFSGSGSGTD FTLKISRVEAEDVGVYYCLQLLEDPYTFGQGTKLEIK |
| 101 | CD19 (8B8-7H07) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ELFDYWGQGTTVTVSS |
| 102 | CD19 (8B8-7H07) VL | DIVMTQTPLSLSVTPGQPASISCKSSQSLETSTGNTYL NWYLQKPGQSPQLLIYRVSKRFSGVPDRFSGSGSGTD FTLKISRVEAEDVGVYYCLQATHIPYTFGQGTKLEIK |
| 103 | CD19 (8B8-2B03) VH | QVQLVQSGAEVKKPGASVKVSCKASGYTFTDYITH WVRQAPGQGLEWMGYINPYNDGSKYTEKFQGRVT MTSDTSISTAYMELSRLRSDDTAVYYCARGTYYYGP DLFDYWGQGTTVTVSS |
| 104 | CD19 (8B8-2B03) VL | DIVMTQTPLSLSVTPGQPASISCKSSQSLETSTGNTYL NWYLQKPGQSPQLLIYRVSKRFSGVPDRFSGSGSGTD FTLKISRVEAEDVGVYYCLQLTHVPYTFGQGXKLEIK |
| 105 | CD19 (8B8-5A07) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSS |
| 106 | CD19 (8B8-5A07) VL | DIVMTQTPLSLSVTPGQPASISCKSSQSLETSTGNTYL NWYLQKPGQSPQLLIYRVSKRFSGVPDRFSGSGSGTD FTLKISRVEAEDVGVYYCLQPGHYPGTFGQGTKLEIK |
| 107 | CD19 (8B8-5D08) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ELFDYWGQGTTVTVSS |
| 108 | CD19 (8B8-5D08) VL | DIVMTQTPLSLSVTPGQPASISCKSSQSLETSTGNTYL NWYLQKPGQSPQLLIYRVSKRFSGVPDRFSGSGSGTD FTLKISRVEAEDVGVYYCLQLTHEPYTFGQGTKLEIK |
| 109 | CD19 (8B8-5B08) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGP QLFDYWGQGTTVTVSS |
| 110 | CD19 (8B8-5B08) VL | DIVMTQTPLSLSVTPGQPASISCKSSQSLETSTGNTYL NWYLQKPGQSPQLLIYRVSKRFSGVPDRFSGSGSGTD FTLKISRVEAEDVGVYYCLQLDSYPNTFGQGTKLEIK |

TABLE C-continued (Sequences):

| SEQ ID NO: | Name | Sequence |
|---|---|---|
| 111 | CD19 (8B8-5H09) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSS |
| 112 | CD19 (8B8-5H09) VL | DIVMTQTPLSLSVTPGQPASISCKSSQSLESSTGNTYL NWYLQKPGQSPQLLIYRVSKRFSGVPDRFSGSGSGTD FTLKISRVEAEDVGVYYCLQLIDYPVTFGQGTKLEIK |
| 113 | CD19 (8B8) VH | QVQLVQSGAEVKKPGASVKVSCKASGYTFTDYIMH WVRQAPGQGLEWMGYINPYNDGSKYTEKFQGRVT MTSDTSISTAYMELSRLRSDDTAVYYCARGTYYYGS ALFDYWGQGTTVTVSS |
| 114 | CD19 (8B8) VL | DIVMTQTPLSLSVTPGQPASISCKSSQSLENSNGNTYL NWYLQKPGQSPQLLIYRVSKRFSGVPDRFSGSGSGTD FTLKISRVEAEDVGVYYCLQLTHVPYTFGQGTKLEIK |
| 115 | human CD19 | UniProt no. P15391 |

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to the numbering systems according to Kabat (Kabat, E. A., et al., Sequences of Proteins of Immunological Interest, 5th ed., Public Health Service, National Institutes of Health, Bethesda, MD (1991)) as defined above.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2× PBS on a Dionex HPLC-System. The eluted protein was quantified by UV absorbance and integration of peak areas. BioRad Gel Filtration Standard 151-1901 served as a standard.

Determination of Binding and Binding Affinity of Antibodies to the Respective Antigens Using Surface Plasmon Resonance (SPR) (BIACORE)

Binding of the generated antibodies to the respective antigens is investigated by surface plasmon resonance using a BIACORE instrument (GE Healthcare Biosciences AB, Uppsala, Sweden). Briefly, for affinity measurements Goat-Anti-Human IgG, JIR 109-005-098 antibodies are immobilized on a CMS chip via amine coupling for presentation of the antibodies against the respective antigen. Binding is measured in HBS buffer (HBS-P (10 mM HEPES, 150 mM NaCl, 0.005% Tween 20, ph 7.4), 25° C. (or alternatively at 37° C.). Antigen (R&D Systems or in house purified) was added in various concentrations in solution. Association was measured by an antigen injection of 80 seconds to 3 minutes; dissociation was measured by washing the chip surface with HBS buffer for 3-10 minutes and a KD value was estimated using a 1:1 Langmuir binding model. Negative control data (e.g. buffer curves) are subtracted from sample curves for correction of system intrinsic baseline drift and for noise signal reduction. The respective Biacore Evaluation Software is used for analysis of sensorgrams and for calculation of affinity data.

Example 1

Preparation, Purification and Characterization of Antigens Fc Fusion for Phage Display Campaign In order to express and purify the human and cynomolgus CD19 ectodomain (Table 1) in a monomeric state, the respective DNA fragment was fused to a human IgG1 Fc gene segment containing the "knob" mutations (human SEQ ID NO: 4; cynomolgus: SEQ ID NO: 7) and was transfected with an "Fc-hole" (SEQ ID NO: 3) counterpart (Merchant et al. (1998) Nat Biotechnol 16, 677-681). An IgA cleavage site (PTPPTP (SEQ ID NO: 119)) was introduced between an antigen ectodomain and the Fc knob chain. An Avi tag for directed biotinylation was introduced at the C-terminus of the antigen-Fc knob chain and mutations H435R and Y436F were introduced in the Fc hole for purification purposes (Jendeberg L. et al, J Immunological methods, 1997). Combination of the antigen-Fc knob chain containing the S354C/T366W mutations (human: SEQ ID NO: 6; cynomolgus: SEQ ID NO: 8), with a Fc hole chain containing the Y349C/T366S/L368A/Y407V mutations (SEQ ID NO: 5) allows generation of a heterodimeric Fc fusion fragment which includes a single copy of the CD19 ectodomain. Table 2 lists the cDNA and amino acid sequences of the antigen Fc-fusion construct.

TABLE 1

Amino acid numbering of antigen ectodomains (ECD) and their origin

| SEQ ID NO: | Construct | Origin | ECD |
|---|---|---|---|
| 1 | human CD19 ECD | Synthesized according to Uniprot# P15391 | aa 20-292 |
| 2 | cynomolgus CD19 ECD | Synthesized according to internal data | aa 20-293 |

TABLE 2 cDNA and Amino acid sequences of monomeric human and cynomolgus CD19 Fc(kih) fusion molecule

| SEQ ID NO: | Antigen | Sequence |
|---|---|---|
| 3 | Nucleotide sequence Fc hole chain | GACAAAACTCACACATGCCCACCGTGCCCAGCACCTGAAG CTGCAGGGGGACCGTCAGTCTTCCTCTTCCCCCCAAAACCC AAGGACACCCTCATGATCTCCCGGACCCCTGAGGTCACATG CGTGGTGGTGGACGTGAGCCACGAAGACCCTGAGGTCAAG TTCAACTGGTACGTGGACGGCGTGGAGGTGCATAATGCCA AGACAAAGCCGCGGGAGGAGCAGTACAACAGCACGTACC GTGTGGTCAGCGTCCTCACCGTCCTGCACCAGGACTGGCTG AATGGCAAGGAGTACAAGTGCAAGGTCTCCAACAAAGCCC TCGGCGCCCCCATCGAGAAAACCATCTCCAAAGCCAAAGG GCAGCCCCGAGAACCACAGGTGTGCACCCTGCCCCCATCC CGGGATGAGCTGACCAAGAACCAGGTCAGCCTCTCGTGCG CAGTCAAAGGCTTCTATCCCAGCGACATCGCCGTGGAGTG GGAGAGCAATGGGCAGCCGGAGAACAACTACAAGACCAC GCCTCCCGTGCTGGACTCCGACGGCTCCTTCTTCCTCGTGA GCAAGCTCACCGTGGACAAGAGCAGGTGGCAGCAGGGGA ACGTCTTCTCATGCTCCGTGATGCATGAGGCTCTGCACAAC CGCTTCACGCAGAAGAGCCTCTCCCTGTCTCCGGGTAAA |
| 4 | Nucleotide sequence human CD19 antigen Fc knob chain avi tag | CCCGAGGAACCCCTGGTCGTGAAGGTGGAAGAGGGCGACA ATGCCGTGCTGCAGTGCCTGAAGGGCACCTCCGATGGCCCT ACCCAGCAGCTGACCTGGTCCAGAGAGAGCCCCCTGAAGC CCTTCCTGAAGCTGTCTCTGGGCCTGCCTGGCCTGGGCATC CATATGAGGCCTCTGGCCATCTGGCTGTTCATCTTCAACGT GTCCCAGCAGATGGGCGGCTTCTACCTGTGTCAGCCTGGCC CCCATCTGAGAAGGCTTGGCAGCCTGGCTGGACCGTGAA CGTGGAAGGATCCGGCGAGCTGTTCCGGTGGAACGTGTCC GATCTGGGCGGCCTGGGATGCGGCCTGAAGAACAGATCTA GCGAGGGCCCCAGCAGCCCCAGCGGCAAACTGATGAGCCC CAAGCTGTACGTGTGGGCCAAGGACAGACCCGAGATCTGG GAGGGCGAGCCTCCTTGCCTGCCCCCTAGAGACAGCCTGA ACCAGAGCCTGAGCCAGGACCTGACAATGGCCCCTGGCAG |

TABLE 2-continued cDNA and Amino acid sequences of monomeric human
and cynomolgus CD19 Fc(kih) fusion molecule

| SEQ ID NO: | Antigen | Sequence |
|---|---|---|
| | | CACACTGTGGCTGAGCTGTGGCGTGCCACCCGACTCTGTGT CTAGAGGCCCTCTGAGCTGGACCCACGTGCACCCTAAGGG CCCTAAGAGCCTGCTGAGCCTGGAACTGAAGGACGACAGG CCCGCCAGAGATATGTGGGTCATGGAAACCGGCCTGCTGC TGCCTAGAGCCACAGCCCAGGATGCCGGCAAGTACTACTG CCACAGAGGCAACCTGACCATGAGCTTCCACCTGGAAATC ACCGCCAGACCCGTGCTGTGGCACTGGCTGCTGAGAACAG GCGGCTGGAAGGTCGACGCTAGCGGTGGTAGTCCGACACC TCCGACACCCGGGGGTGGTTCTGCAGACAAAACTCACACA TGCCCACCGTGCCCAGCACCTGAAGCCGCAGGGGGACCGT CAGTCTTCCTCTTCCCCCCAAAACCCAAGGACACCCTCATG ATCTCCCGGACCCCTGAGGTCACATGCGTGGTGGTGGACGT GAGCCACGAAGACCCTGAGGTCAAGTTCAACTGGTACGTG GACGGCGTGGAGGTGCATAATGCCAAGACAAAGCCGCGGG AGGAGCAGTACAACAGCACGTACCGTGTGGTCAGCGTCCT CACCGTCCTGCACCAGGACTGGCTGAATGGCAAGGAGTAC AAGTGCAAGGTCTCCAACAAAGCCCTCGGAGCCCCCATCG AGAAAACCATCTCCAAAGCCAAAGGGCAGCCCCGAGAACC ACAGGTGTACACCCTGCCCCCCATGCCGGGATGAGCTGACC AAGAACCAGGTCAGCCTGTGGTGCCTGGTCAAAGGCTTCT ATCCCAGCGACATCGCCGTGGAGTGGGAGAGCAATGGGCA GCCGGAGAACAACTACAAGACCACGCCTCCCGTGCTGGAC TCCGACGGCTCCTTCTTCCTCTACAGCAAGCTCACCGTGGA CAAGAGCAGGTGGCAGCAGGGGAACGTCTTCTCATGCTCC GTGATGCATGAGGCTCTGCACAACCACTACACGCAGAAGA GCCTCTCCCTGTCTCCGGGTAAATCCGGAGGCCTGAACGAC ATCTTCGAGGCCCAGAAGATTGAATGGCACGAG |
| 5 | Polypeptide sequence Fc hole chain | DKTHTCPPCPAPEAAGGPSVFLFPPKPKDTLMISRTPEVTCVV VDVSHEDPEVKFNWYVDGVEVHNAKTKPREEQYNSTYRVVS VLTVLHQDWLNGKEYKCKVSNKALGAPIEKTISKAKGQPREP QVCTLPPSRDELTKNQVSLSCAVKGFYPSDIAVEWESNGQPE NNYKTTPPVLDSDGSFFLVSKLTVDKSRWQQGNVFSCSVMHE ALHNRFTQKSLSLSPGK |
| 6 | Polypeptide sequence human CD19 antigen Fc knob chain avi tag | PEEPLVVKVEEGDNAVLQCLKGTSDGPTQQLTWSRESPLKPF LKLSLGLPGLGIHMRPLAIWLFIFNVSQQMGGFYLCQPGPPSE KAWQPGWTVNVEGSGELFRWNVSDLGGLGCGLKNRSSEGPS SPSGKLMSPKLYVWAKDRPEIWEGEPPCLPPRDSLNQSLSQDL TMAPGSTLWLSCGVPPDSVSRGPLSWTHVHPKGPKSLLSLEL KDDRPARDMWVMETGLLLPRATAQDAGKYYCHRGNLTMSF HLEITARPVLWHWLLRTGGWKVDASGGSPTPPTPGGGSADK THTCPPCPAPEAAGGPSVFLFPPKPKDTLMISRTPEVTCVVVD VSHEDPEVKFNWYVDGVEVHNAKTKPREEQYNSTYRVVSVL TVLHQDWLNGKEYKCKVSNKALGAPIEKTISKAKGQPREPQV YTLPPCRDELTKNQVSLWCLVKGFYPSDIAVEWESNGQPENN YKTTPPVLDSDGSFFLYSKLTVDKSRWQQGNVFSCSVMHEAL HNHYTQKSLSLSPGKSGGLNDIFEAQKIEWHE |
| 7 | Nucleotide sequence cynomolgus CD19 antigen Fc knob chain avi tag | CCCCAGGAACCCCTGGTCGTGAAGGTGGAAGAGGGCGACA ATGCCGTGCTCCAGTGCCTGGAAGGCACCTCCGATGGCCCT ACACAGCAGCTCGTGTGGTGCAGAGACAGCCCCTTCGAGC CCTTCCTGAACCTGTCTCTGGGCCTGCCCTGGCATGGGCATC AGAATGGGCCCTCTGGGCATCTGGCTGCTGATCTTCAACGT GTCCAACCAGACCGGCGGCTTCTACCTGTGTGTCAGCCTGGCC TGCCAAGCGAGAAGGCTTGGCAGCCTGGATGGACCGTGTC CGTGGAAGGATCTGGCGAGCTGTTCCGGTGGAACGTGTCC GATCTGGGCGGCCTGGGATGCGGCCTGAAGAACAGAAGCA GCGAGGGCCCTAGCAGCCCCAGCGGCAAGCTGAATAGCAG CCAGCTGTACGTGTGGGCCAAGGACAGACCCGAGATGTGG GAGGGCGAGCCTGTGTGTGGCCCCCCCTAGAGATAGCCTGA ACCAGAGCCTGAGCCAGGACCTGACAATGGCCCCTGGCAG CACACTGTGGCTGAGCTGTGGCGTGCCACCCGACTCTGTGT CCAGAGGCCCTCTGAGCTGGACACACGTGCGGCCAAAGGG CCCTAAGAGCAGCCTGCTGAGCCTGGAACTGAAGGACGAC CGGCCCGACCGGGATATGTGGGTGGTGGATACAGGCCTGC TGCTGACCAGAGCCACAGCCCAGGATGCCGGCAAGTACTA CTGCCACAGAGGCAACTGGACCAAGAGCTTTTACCTGGAA ATCACCGCCAGACCCGCCCTGTGGCACTGGCTGCTGAGAAT CGGAGGCTGGAAGGTCGACGCTAGCGGTGGTAGTCCGACA CCTCCGACACCCGGGGGTGGTTCTGCAGACAAAACTCACA CATGCCCACCGTGCCCAGCACCTGAAGCCGCAGGGGGACC GTCAGTCTTCCTCTTCCCCCCAAAACCCAAGGACACCCTCA TGATCTCCCGGACCCCTGAGGTCACATGCGTGGTGGTGGAC |

TABLE 2-continued cDNA and Amino acid sequences of monomeric human
and cynomolgus CD19 Fc(kih) fusion molecule

| SEQ ID NO: | Antigen | Sequence |
|---|---|---|
| | | GTGAGCCACGAAGACCCTGAGGTCAAGTTCAACTGGTACG |
| | | TGGACGGCGTGGAGGTGCATAATGCCAAGACAAAGCCGCG |
| | | GGAGGAGCAGTACAACAGCACGTACCGTGTGGTCAGCGTC |
| | | CTCACCGTCCTGCACCAGGACTGGCTGAATGGCAAGGAGT |
| | | ACAAGTGCAAGGTCTCCAACAAAGCCCTCGGAGCCCCCAT |
| | | CGAGAAAACCATCTCCAAAGCCAAAGGGCAGCCCCGAGAA |
| | | CCACAGGTGTACACCCTGCCCCCCATGCCGGGATGAGCTGA |
| | | CCAAGAACCAGGTCAGCCTGTGGTGCCTGGTCAAAGGCTT |
| | | CTATCCCAGCGACATCGCCGTGGAGTGGGAGAGCAATGGG |
| | | CAGCCGGAGAACAACTACAAGACCACGCCTCCCGTGCTGG |
| | | ACTCCGACGGCTCCTTCTTCCTCTACAGCAAGCTCACCGTG |
| | | GACAAGAGCAGGTGGCAGCAGGGGAACGTCTTCTCATGCT |
| | | CCGTGATGCATGAGGCTCTGCACAACCACTACACGCAGAA |
| | | GAGCCTCTCCCTGTCTCCGGGTAAATCCGGAGGCCTGAACG |
| | | ACATCTTCGAGGCCCAGAAGATTGAATGGCACGAG |
| 8 | Polypeptide sequence cynomolgus CD19 antigen Fc knob chain avi tag | PQEPLVVKVEEGDNAVLQCLEGTSDGPTQQLVWCRDSPFEPF LNLSLGLPGMGIRMGPLGIWLLIFNVSNQTGGFYLCQPGLPSE KAWQPGWTVSVEGSGELFRWNVSDLGGLGCGLKNRSSEGPS SPSGKLNSSQLYVWAKDRPEMWEGEPVCGPPRDSLNQSLSQD LTMAPGSTLWLSCGVPPDSVSRGPLSWTHVRPKGPKSSLLSLE LKDDRPDRDMWVVDTGLLLTRATAQDAGKYYCHRGNWTKS FYLEITARPALWHWLLRIGGWKVDASGGSPTPPTPGGGSADK THTCPPCPAPEAAGGPSVFLFPPKPKDTLMISRTPEVTCVVVD VSHEDPEVKFNWYVDGVEVHNAKTKPREEQYNSTYRVVSVL TVLHQDWLNGKEYKCKVSNKALGAPIEKTISKAKGQPREPQV YTLPPCRDELTKNQVSLWCLVKGFYPSDIAVEWESNGQPENN YKTTPPVLDSDGSFFLYSKLTVDKSRWQQGNVFSCSVMHEAL HNHYTQKSLSLSPGKSGGLNDIFEAQKIEWHE |

For the production of the monomeric antigen/Fc fusion molecules, exponentially growing suspension CHO cells were co-transfected with two plasmids encoding the two components of fusion protein (knob and hole chains) using standard methods.

Secreted protein was purified from cell culture supernatant by affinity chromatography using Protein A, followed by size exclusion chromatography. For affinity chromatography, the supernatant was loaded on a MabSelect Sure column volume (CV)=5-15 mL, resin from GE Healthcare) equilibrated with Sodium Phosphate (20 mM), Sodium Citrate (20 mM), 0.5M sodium chloride buffer (pH 7.5). Unbound protein was removed by washing with at least 6 column volumes of the same buffer. The bound protein was eluted using a linear gradient; step 1, 10 CV from 0 to 60% elution buffer (20 mM sodium citrate, 500 mM Sodium chloride buffer (pH 2.5)); step 2, 2 CV from 60 to 100% elution buffer. For the linear gradient an additional 2 column volumes step elution with 100% elution buffer was applied.

The pH of collected fractions was adjusted by adding 1/40 (v/v) of 2M Tris, pH8.0. The protein was concentrated and filtered prior to loading on a HiLoad Superdex 200 column (GE Healthcare) equilibrated with 2 mM MOPS, 150 mM sodium chloride, 0.02% (w/v) sodium azide solution of pH 7.4.

Table 3 summarizes the yield and final monomer content of monomeric human and cynomolgus CD19 Fc(kih) fusion protein.

TABLE 3

Biochemical analysis of monomeric human and cynomolgus CD19 Fc(kih) fusion protein

| Construct | Monomer [%] (SEC) | Yield [mg/l] |
|---|---|---|
| monomeric human CD19 Fc(kih) fusion protein | 91 | 0.2 |
| monomeric cynomolgus CD19 Fc(kih) fusion protein | 95 | 3.56 |

Part of the purified antigen was in vitro biotinylated using the BirA biotin-protein ligase standard reaction kit (Avidity, Cat. #BirA500) according to the manufacturer's instructions. The biotinylation degree for the human CD19-containing fusion was 94%, for the respective cynomolgus CD19 construct 100%. The biotinylated protein was then used for selection, screening and characterization of affinity-matured 8B8-derived clones devoid of the de-amidation hotspots N27d and N28.

Example 2

Selection of Affinity Matured CD19-Specific Antibodies

De-amidation of the asparagine residues at positions 27d and 28, located in CDR1 of the light chain of the humanized clone 8B8 (described in WO 2011/147834), leads to a significant reduction in the biological activity. Therefore, 2 phage display libraries were generated in which a) both asparagine residues at positions 27d and 28 were eliminated and b) additional CDRs of heavy and light chain were randomized in order to select for 8B8 variants with an improved affinity.

2.1 Generation of 8B8 Affinity Maturation Libraries Devoid of LCDR1 Hotspots

Figure 1:
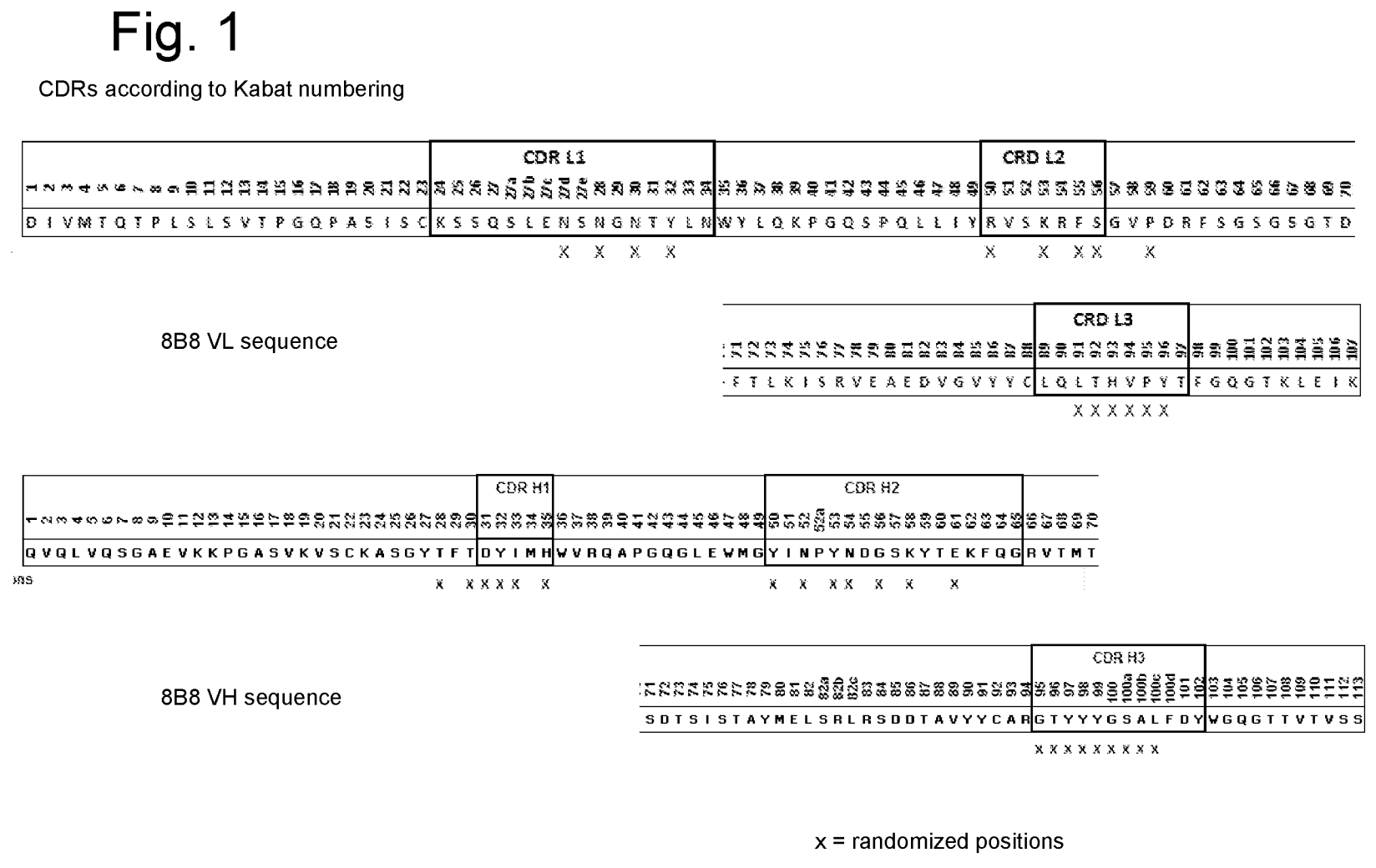

Generation of affinity-matured 8B8-derived antibodies without the de-amidation sites N27d and N28, located in LCDR1, was carried out by phage display using standard protocols (Silacci et al, 2005). In a first step, the VL and VH DNA sequences of the humanized parental clone 8B8 (SEQ ID NO: 9 and SEQ ID NO: 10) were cloned into our phagemid which was then used as a template for randomization. In a next step, two libraries were generated for the selection of favourable clones by phage display. In order to eliminate the above-mentioned hotspot positions, a LCDR1 randomization primer (SEQ ID NO: 11) that only allowed amino acids S T Q E at positions 27d and 28 was used for both libraries. Maturation library 1 was randomized in CDR1 and 2 of both the light and the heavy chain, while maturation library 2 was randomized in CDR1 and 3 of the light chain and in CDR3 of the heavy chain. The randomized positions in the respective CDR regions are shown in FIG. 1. For the generation of the maturation library 1, randomized in CDR1 and 2 of both the light and the heavy chain, three fragments were assembled by "splicing by overlapping extension" (SOE) PCR and cloned into the phage vector (FIG. 2). The following primer combinations were used to generate the library fragments: fragment 1 (LMB3 (SEQ ID NO: 16) and CD19 L1 reverse random (SEQ ID NO: 11), fragment 2 (CD19 L2 forward random (SEQ ID NO: 12) and CD19 H1 reverse random (SEQ ID NO: 13), and fragment 3 (CD19 H2 forward random (SEQ ID NO: 14) and CD19 H3 reverse constant (SEQ ID NO: 15) (Table 4). After assembly of sufficient amounts of full length randomized fragment, it was digested with NcoI/NheI alongside with identically treated acceptor phagemid vector. A 3-fold molar excess of library insert was ligated with 10 μg of phagemid vector. Purified ligations were used for 20 transformations resulting in 2×10 exp9 transformants. Phagemid particles displaying the 8B8 affinity maturation library were rescued and purified by PEG/NaCl purification to be used for selections.

The generation of the second library, randomized in CDR1 and 3 of the light chain and in CDR3 of the heavy chain, was done similarly. The following primer combinations were used to generate the library fragments: fragment 1 (LMB3 (SEQ ID NO: 16) and CD19 L1 reverse random (SEQ ID NO: 11), fragment 2 (CD19 L1 forward constant (SEQ ID NO 223) and CD19 L3 reverse random (SEQ ID NO 224), and fragment 3 (CD19 L3 forward constant (SEQ ID NO 225) and CD19 H3 reverse random (SEQ ID NO: 226) (Table 5). After assembly of sufficient amounts of full length randomized fragment, it was digested with NcoI/KpnI alongside with identically treated acceptor phagemid vector. A 3-fold molar excess of library insert was ligated with 20 ug of phagemid vector. Purified ligations were used for 40 transformations resulting in 2×10 exp9 transformants. Phagemid particles displaying the 8B8 affinity maturation library were rescued and purified by PEG/NaCl purification to be used for selections.

TABLE 4

| Primers for 8B8 affinity maturation and hotspot removal library L1_L2/H1_H2 | | |
|---|---|---|
| SEQ ID | Name | Sequence |
| 11 | CD19 L1 reverse random | CAG CTG CGG GCT CTG ACC CGG TTT CTG GAG ATA CCA GTT CAG 1 CGT 2 GCC 3 GGA 4 TTC CAG AGA TTG GCT GGA TTT GCA AGA AAT G<br>1: 40% Y, 6% A/S/T/G/P/D/N/E/Q/V<br>2: 40% N, 6% A/S/T/Y/G/P/D/E/Q/V<br>3: 25% S/T/Q/E<br>4: 25% S/T/Q/E |
| 12 | CD19 L2 forward random | CTC CAG AAA CCG GGT CAG AGC CCG CAG CTG CTG ATC TAC 5 GTA TCT 6 CGC 7 8 GGC GTT 9 GAT CGT TTC AGC GGT TCT GGA TCC GGC ACC<br>5: 30% R, 20% E,<br>5% A/S/T/Y/G/P/D/N/Q/V<br>6: 30% K, 20% S,<br>5% A/N/T/Y/G/P/D/E/Q/V<br>7: 40% F,<br>5% A/S/T/Y/G/P/D/E/Q/V/I/L<br>8: 40% S, 6.6% A/T/Y/G/P/D/E/Q/V<br>9: 50% P, 50% L |
| 13 | CD19 H1 reverse random | CAT CCA CTC CAG ACC CTG GCC CGG GGC CTG ACG AAC CCA 10 CAT 11 12 13 14 GAA 15 GTA ACC AGA TGC TTT GCA GCT CAC TTT AAC GGA AGC<br>10: 52% H,<br>4% G/A/S/P/T/N/Y/D/E/Q/V/I<br>11: 30% I, 15% Y,<br>5% G/A/S/T/P/N/H/D/E/Q/V<br>12: 52% Y,<br>4% G/A/S/P/T/N/H/D/E/Q/V/I<br>13: 30% D, 15% G,<br>5% A/S/P/Y/N/H/D/E/Q/V/I<br>14: 52% T,<br>4% G/A/S/P/Y/N/H/D/E/Q/V/I<br>15: 52% T,<br>4% G/A/S/P/Y/N/H/D/E/Q/V/I |
| 14 | CD19 H2 forward random | CAG GCC CCG GGC CAG GGT CTG GAG TGG ATG GGC 16 ATT 17 CCA 18 19 20 21 TCC 22 TAT ACC 23 AAA TTC CAG GGC CGC GTC ACG ATG ACC<br>16: 45% Y,<br>5% A/S/P/T/N/H/D/E/Q/V/I<br>17: 52% N,<br>4% G/A/S/P/Y/T/H/D/E/Q/V/I<br>18: 40% Y,<br>5% G/A/S/P/T/N/H/D/E/Q/V/I<br>19: 30% N, 15% S,<br>5% G/A/T/P/Y/H/D/E/Q/V/I<br>20: 30% D, 15% G,<br>5% A/S/T/P/Y/N/H/E/Q/V/I<br>21: 52% G,<br>4% N/A/S/P/Y/T/H/D/E/Q/V/I<br>22: 30% K, 15% N,<br>4% G/A/S/P/Y/T/H/D/E/Q/V/I<br>23: 30% E, 15% Q,<br>5% G/A/S/T/P/Y/N/H/D/V/I |
| 15 | CD19 H3 reverse constant | CGTCACCGGTTCGGGGAAGTAGTCCTTGACC AG |
| 16 | LMB3 | CAGGAAACAGCTATGACCATGATTAC |

TABLE 5

Primers for 8B8 affinity maturation
and hotspot removal library L1_L3/H3

| SEQ ID | Name | Sequence |
|--------|------|----------|
| 17 | D19 L1 forward constant | TGGTATCTCCAGAAACCGGGTCAGAGCCCGCAG |
| 11 | CD19 L1 reverse random | See Table 4 |
| 18 | CD19 L3 reverse random | TTT AAT TTC CAG TTT AGT TCC TTG ACC GAA GGT 24 25 26 27 28 29 CTG CAG ACA ATA GTA GAC GCC AAC GTC TTC AGC<br>24: 52% Y,<br>4% G/A/S/T/N/P/D/E/Q/V/L/I<br>25: 52% P,<br>4% G/A/S/T/Y/N/H/D/E/Q/V/I<br>26: 42% V, 10% L,<br>4% G/A/S/T/Y/N/P/D/E/Q/V/I<br>27: 52% H,<br>4% G/A/S/T/Y/N/P/D/E/Q/V/I<br>28: 42% T, 10% I,<br>4% G/A/S/T/Y/N/P/D/E/Q/V/L<br>29: 45% L, 11% G,<br>4% A/S/T/Y/N/P/D/E/Q/V/I |
| 19 | CD19 L3 forward constant | ACCTTCGGTCAAGGAACTAAACTGGAAATTAAA CG |
| 20 | CD19 H3 reverse random | TT GGT GCT AGC AGA GCT TAC GGT CAC CGT GGT ACC TTG GCC CCA GTA ATC AAA 30 31 32 33 34 35 36 37 38 GCG TGC ACA ATA GTA AAC AGC GGT GTC<br>30: 50% L,<br>3.8% G/A/S/T/P/H/Y/N/D/E/Q/V/I<br>31: 50% A,<br>4.2% G/S/T/P/H/Y/N/D/E/Q/V/I<br>32: 50% S,<br>4.2% G/A/T/P/H/Y/N/D/E/Q/V/I<br>33: 50% G,<br>4.2% S/A/T/P/H/Y/N/D/E/Q/V/I<br>34: 50% Y,<br>4.2% G/A/T/P/H/S/N/D/E/Q/V/I<br>35: 50% Y,<br>4.2% G/A/T/P/H/S/N/D/E/Q/V/I<br>36: 50% Y,<br>4.2% G/A/T/P/H/S/N/D/E/Q/V/I<br>37: 50% T,<br>4.2% G/A/Y/P/H/S/N/D/E/Q/V/I<br>38: 50% G,<br>4.2% Y/A/T/P/H/S/N/D/E/Q/V/I |
| 16 | LMB3 | See Table 4 |

2.2 Selection of Affinity Matured 8B8-Derived Clones Devoid of LCDR1 Hotspots N27d and N28

For the selection of affinity-matured clones devoid of the LCDR1 hotspots N27d and N28, two selection approaches by phage display were performed:

In the first approach, the selection was executed on human CD19-Fc fusion protein using both phage display libraries Panning rounds were performed in solution according to the following pattern: 1. binding of ~$10^{-12}$ phagemid particles to 30 nM biotinylated CD19-Fc protein for 0.5 h in a total volume of 1 ml, 2. capture of biotinylated CD19-Fc protein and specifically bound phage particles by addition of 5.4× $10^7$ streptavidin-coated magnetic beads for 10 min, 3. washing of beads using 5× 1 ml PBS/Tween20 and 5× 1 ml PBS, 4. elution of phage particles by addition of 1 ml 100 mM TEA for 10 min and neutralization by adding 500 ul 1M Tris/HCl pH 7.4, 5. re-infection of exponentially growing E. coli TG1 bacteria, and 6.infection with helperphage VCSM13 and subsequent PEG/NaCl precipitation of phagemid particles to be used in subsequent selection rounds. Selections were carried out over 3 rounds using decreasing antigen concentrations ($30\times10^{-9}$ M, $10\times10^{-9}$ M, and $3\times10^{-9}$ M). In round 2 and 3, capture of antigen:phage complexes was performed using neutravidin plates instead of streptavidin beads. Neutravidin plates were washed with 5×PBS/ Tween20 and 5×PBS. In round 3, the neutravidin plate was incubated overnight in 2 liters PBS for an "off-rate" selection before phage was eluted from the plate. Furthermore, cynomolgus CD19-Fc protein was used in round 2 in order to enrich cross-reactive binders.

In the second selection approach, the phage panning was executed on cells transiently expressing either the human or cynomolgus CD19 ECD on the cell surface. For the transient transfection of HEK cells, expression plasmids were generated that harbor the DNA sequences (from 5' to 3') for the following protein segments: A Flag tag, a SNAP tag, the CD19 ECD of either human or cynomolgus origin, and the transmembrane region of the Platelet-derived growth factor receptor (PDGFR) (SEQ ID NOs: 21 and 22). The expression of the respective proteins (SEQ ID NOs: 23 and 24) on the cell surface was confirmed by flow cytometry using an anti-Flag antibody for detection. Both libraries were exposed in the first selection round to cells either expressing the human or cynomolgus CD19 ECD-containing protein fusion. For the subsequent panning rounds, the species of the CD19 ECD was alternated accordingly. Cells transiently transfected with an irrelevant membrane protein were used for pre-clearing.

Panning rounds were performed according to the following pattern: 1. Transfection of HEK cells with constructs expressing either CD19 ECD or an irrelevant transmembrane protein according to the standard procedure described before, 2. Incubation of the cells for total 48 h at 37° C. in an incubator with a 5% $CO_2$ atmosphere, 3. Isolation of cells by centrifugation (3 min at 250×g) and re-suspension of 1×10E7 CD19 ECD-positive cells and 1×10E7 negative cells in PBS/5% BSA, respectively, 3. Pre-clearing of unspecific phage by incubating the phage library with 1×107 CD19-negative cells for 60 min at 4° C. using a gently rotating tube rotator, 4. Centrifugation of cells at 250×g for 3 min and transfer of supernatant into a fresh tube. Addition of 1×10E7 CD19-positive cells and incubation for 60 min at 4° C. by gentle rotation on a tube rotator, 5. Washing of cells by centrifugation for 1 min at 250×g, aspiration of the supernatant, and re-suspension in 1 ml PBS (8 times), 6. Phage elution with 1 ml 100 mM TEA, incubation for 5 min at RT, and neutralization of the eluate with 500 ul 1M Tris-HCl, pH7.6, 7. re-infection of exponentially growing E. coli TG1 bacteria, and 8.infection with helperphage VCSM13 and subsequent PEG/NaCl precipitation of phagemid particles to be used in subsequent selection rounds. Selections were carried out over 3 rounds.

For both selection approaches, specific binders were identified by ELISA as follows: 100 ul of 30 nM biotinylated CD19-Fc protein per well were coated on neutravidin plates. Fab-containing bacterial supernatants were added and binding Fabs were detected via their Flag-tags using an anti-Flag/HRP secondary antibody.

Clones that were ELISA-positive on recombinant human CD19 were further tested in a cell-based ELISA using cells that were transiently transfected with the human CD19 ECD-containing expression plasmid (SEQ ID NO: 227). This analysis was performed as follows: 48 h after transfection, HEK cells were harvested and centrifuged at 250×g for 5 min Cells were then re suspended in ice-cold PBS BSA 2% to 4×10⁶ cells/ml and incubated for 20 min on ice to block unspecific binding sites. 4×10⁵ cells in 100 ul were distributed to each well of a 96 well plate and centrifuged at 250×g and 4° C. for 3 min. Supernatant was aspirated off and 50 ul bacterial supernatant containing soluble Fab fragments was diluted with 50 ul ice-cold PBS/BSA 2%, added to the plate, mixed with the cells and incubated for 1 h at 4° C. Afterwards, cells were washed 3 times with ice cold PBS before 100 ul PBS BSA 2% per well containing a 1:2000 dilution of anti-Fab-HRP antibody were added. After an incubation time of 1 h, cells were washed again 3 times with ice-cold PBS. For the development, 100 ul "1-step ultra TMB-ELISA" substrate was added per well. After an incubation time of 10 minutes, supernatant was transferred to a new 96-well plate containing 40 ul H₂SO₄ 1M per well and absorbance was measured at 450 nM. Clones exhibiting significant signals over background were subjected to a kinetic screening experiment by SPR-analysis using ProteOn XPR36.

2.3 Identification of Affinity-Matured 8B8-Derived Variants by SPR

In order to further characterize the ELISA-positive clones, the off-rate was measured by surface plasmon resonance using a ProteOn XPR36 machine and compared with the parental humanized clone 8B8.

Figure 3:
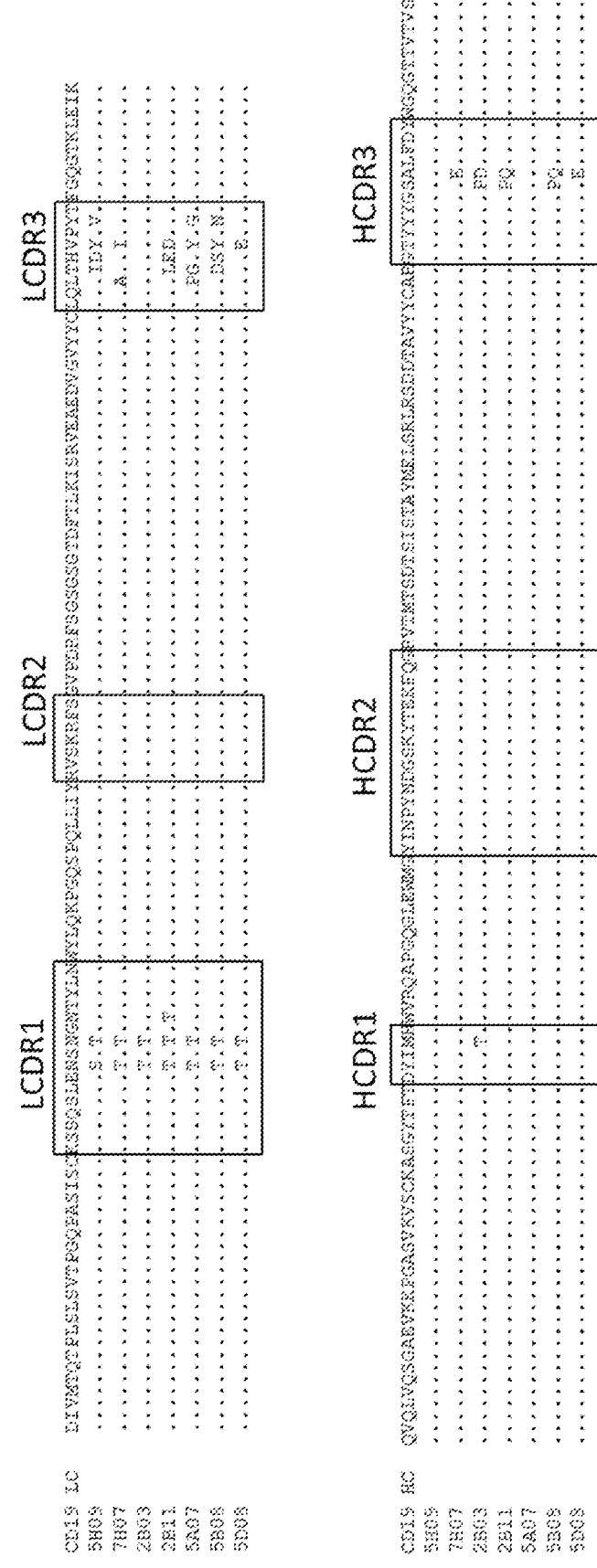
FIG. 3 shows the alignment of the parental anti-CD19 clone 8B8 with the selected affinity-matured binders. Shown are the sequences of clone 8B8 and all selected affinity-matured binders. CDRs of both heavy and light chains are framed.
Figures 4A, 4B:
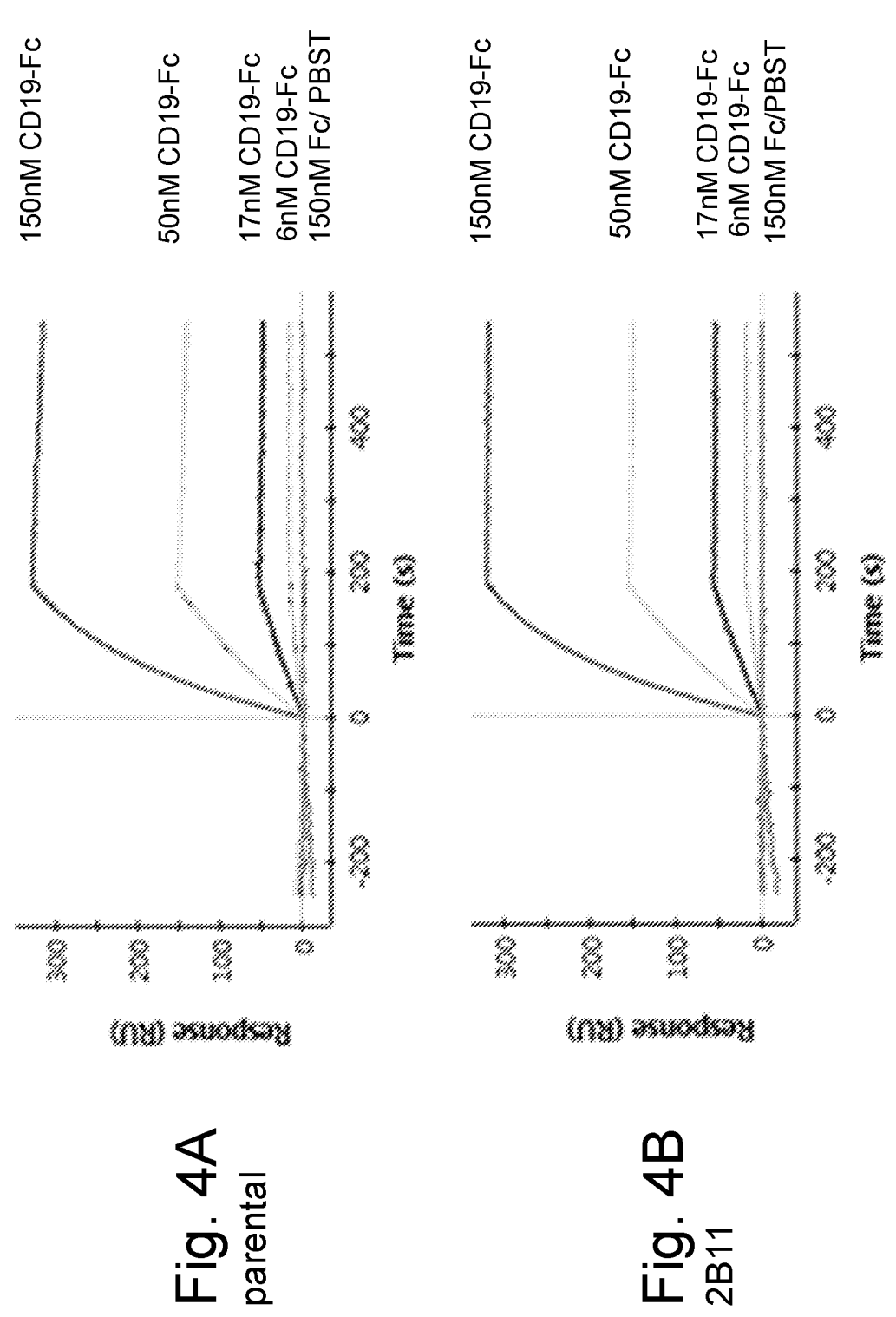
FIGS. 4A to 4H relate to the SPR analysis of the parental 8B8 clone and its affinity-matured variants. Shown are the sensorgrams of clone 8B8 and its affinity-matured derivatives that are devoid of the LCDR1 N27d and N28 hotspots.
Figures 4C, 4D:
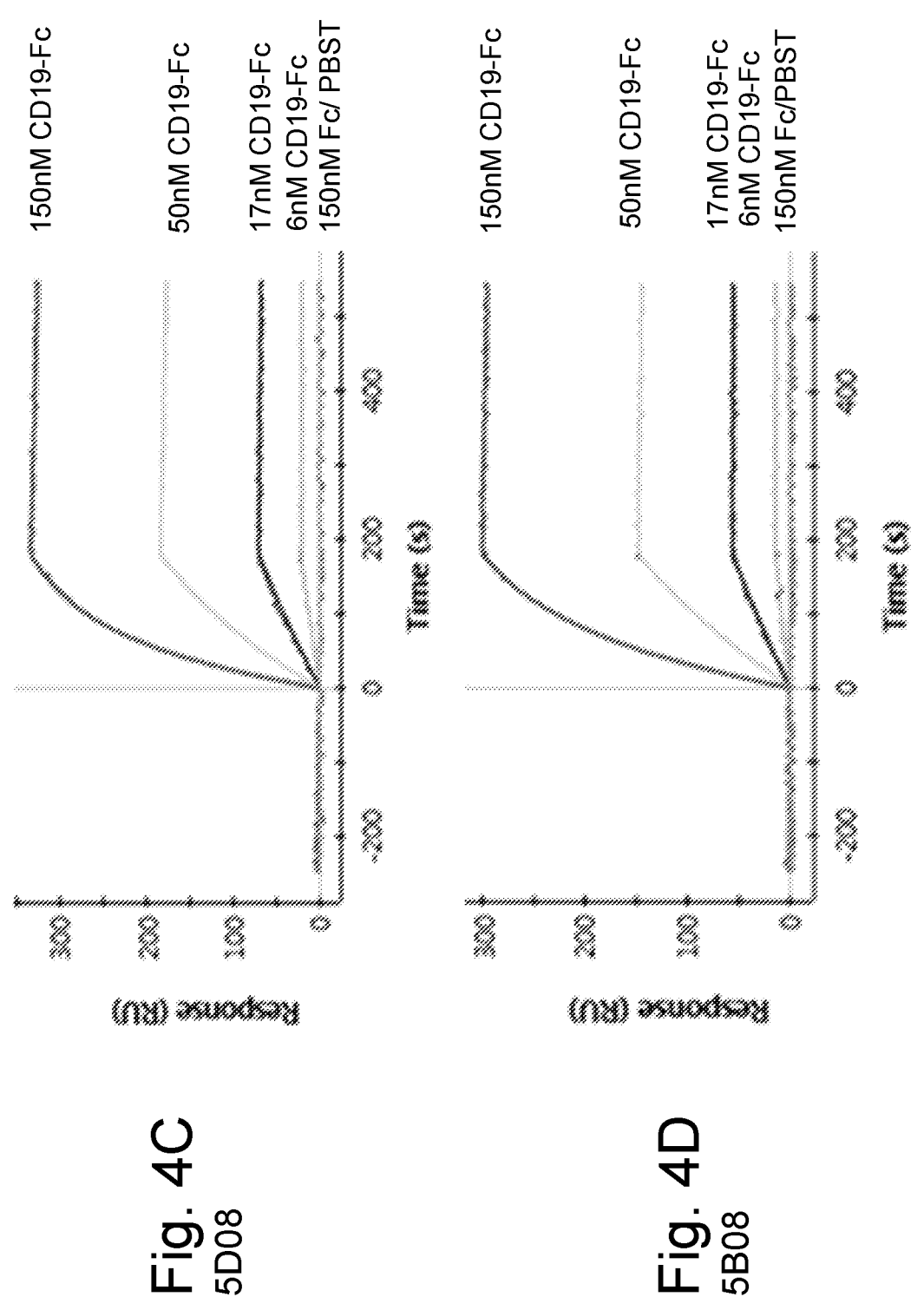
Figures 4E, 4F:
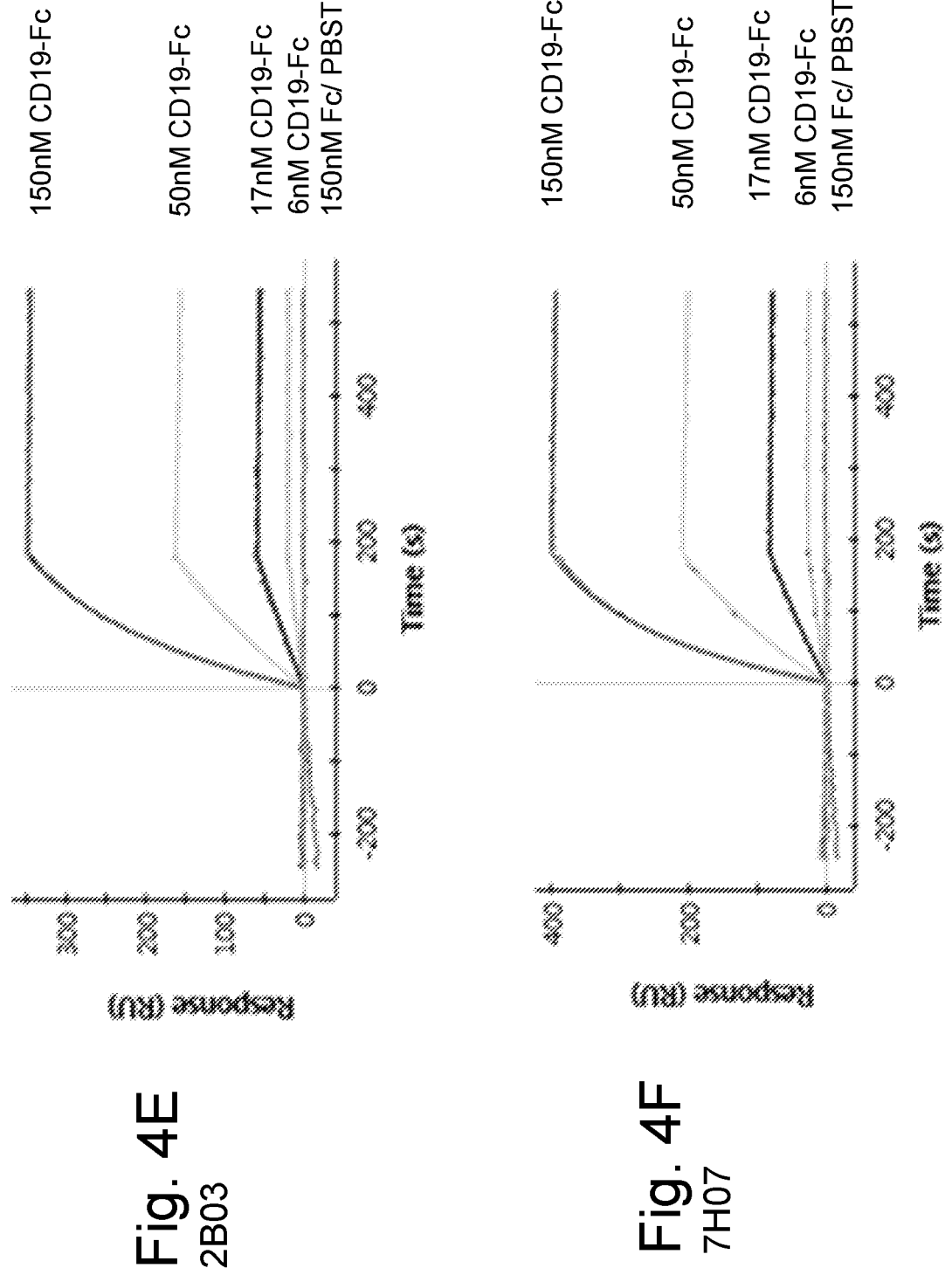
Figures 4G, 4H:
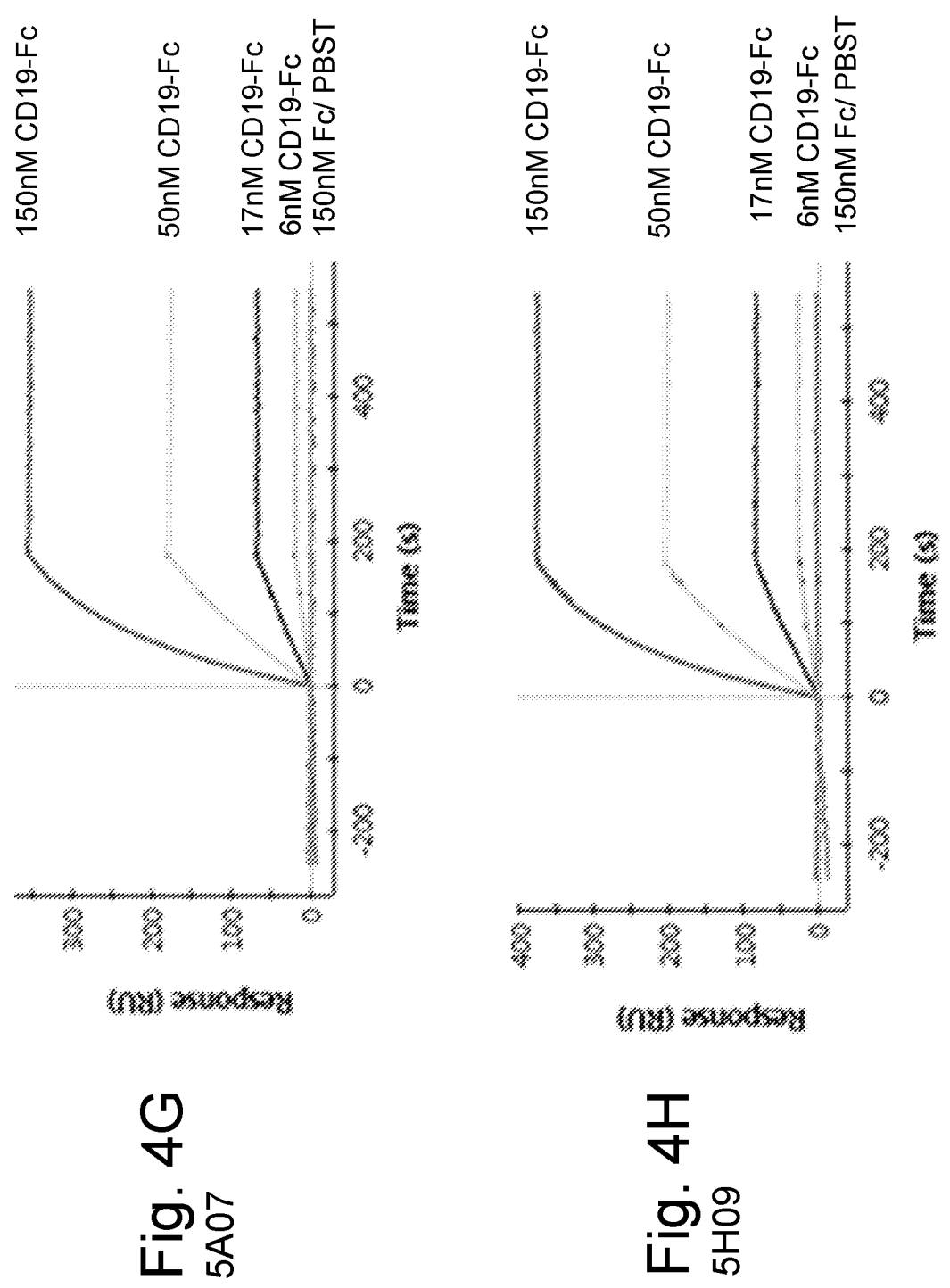

For this experiment, 7000 RU of polyclonal anti-human Fab antibody were immobilized on all 6 channels of a GLM chip by Amine coupling (NaAcetate pH4.5, 25 µl/min, 240 s) (vertical orientation). Each antibody-containing bacterial supernatant was filtered and 2-fold diluted with PBS, and then injected for 360 s at 25 µl/minute to achieve immobilization levels of between 100 and 400 response units (RU) in vertical orientation. Injection of monomeric CD19-Fc: For one-shot kinetics measurements, injection direction was changed to horizontal orientation, three-fold dilution series of purified monomeric CD19-Fc (varying concentration ranges between 150 and 6 nM) were injected simultaneously at 50 µl/min along separate channels 1-4, with association times of 180 s, and dissociation times of 300 s. A human IgG Fc fragment (150 nM) was injected in channel 5 as a negative control for specific binding to monomeric CD19-Fc. Buffer (PBST) was injected along the sixth channel to provide an "in-line" blank for referencing. Regeneration was performed by two pulses of 10 mM glycine pH 1.5 and 50 mM NaOH for 30 s at 90 ul/min (horizontal orientation). Dissociation rate constants ($k_{off}$) were calculated using a simple one-to-one Langmuir binding model in ProteOn Manager v3.1 software by simultaneously fitting the sensorgrams. Clones expressing Fabs with the slowest dissociation rate constants were identified (Table 6). Of note, the dissociation rate constants of clones 5A07 and 5B08 could not be determined due to inadequate fitting. Nevertheless, both clones were selected because results obtained suggested a very slow dissociation. The variable domains of the corresponding phagemids were sequenced. Importantly, both asparagine residue in LCDR1 (position 27d and 28) were replaced by a serine or a threonine, demonstrating that both de-amidation sites were removed. An alignment is shown in FIG. 3. The CDRs of the best clones are listed in Table 7 (variable regions of the light chain) and Table 8 (variable regions of the heavy chain) (clone 5H09: (SEQ ID NO:25-30); clone 7H07: (SEQ ID NO:31-36); clone 2B03: (SEQ ID NO: 37-42); clone 2B11: (SEQ ID NO:43-48); clone 5A07: (SEQ ID NO:49-54); clone 5B08: (SEQ ID NO:55-60); clone 5D08: (SEQ ID NO:61-66).

TABLE 6

Dissociation constants of selected clones obtained in screening analysis with bacterial supernatant

| clone | Dissociation constant kd (1/s) |
|---|---|
| Parental 8B8 | 3.01E-4 |
| 5H09 | 2.58E-4 |
| 7H07 | 5.75E-5 |
| 2B03 | 3.24E-5 |
| 2B11 | 4.37E-6 |
| 5A07 | n.d. |
| 5B08 | n.d. |
| 5D08 | 1.95E-4 |

TABLE 7

CDR sequences of the selected 8B8 light chains

| clone | SEQ ID NO | CDR-L1 | SEQ ID NO | CDR-L2 | SEQ ID NO | CDR-L3 |
|---|---|---|---|---|---|---|
| 5H09 | 25 | KSSQSLES STGNTYLN | 26 | RVSKRFS | 27 | LQLIDYPVT |
| 7H07 | 31 | KSSQSLET STGNTYLN | 32 | RVSKRFS | 33 | LQATHIPYT |
| 2B03 | 37 | KSSQSLET STGNTYLN | 38 | RVSKRFS | 39 | LQLTHVPYT |
| 2B11 | 43 | KSSQSLET STGTTYLN | 44 | RVSKRFS | 45 | LQLLEDPYT |
| 5A07 | 49 | KSSQSLET STGNTYLN | 50 | RVSKRFS | 51 | LQPGHYPGT |
| 5B08 | 55 | KSSQSLET STGNTYLN | 56 | RVSKRFS | 57 | LQLDSYPNT |
| 5D08 | 61 | KSSQSLET STGNTYLN | 62 | RVSKRFS | 63 | LQLTHEPYT |

TABLE 8

CDR sequences of the selected 8B8 heavy chains

| clone | SEQ ID NO | CDR-H1 | SEQ ID NO | CDR-H2 | SEQ ID NO | CDR-H3 |
|---|---|---|---|---|---|---|
| 5H09 | 28 | DYIMH | 29 | YINPYNDGS KYTEKFQG | 30 | GTYYYGSALFDY |
| 7H07 | 34 | DYIMH | 35 | YINPYNDGS KYTEKFQG | 36 | GTYYYGSELFDY |
| 2B03 | 40 | DYITH | 41 | YINPYNDGS KYTEKFQG | 42 | GTYYYGPDLFDY |
| 2B11 | 46 | DYIMH | 47 | YINPYNDGS KYTEKFQG | 48 | GTYYYGPQLFDY |
| 5A07 | 52 | DYIMH | 53 | YINPYNDGS KYTEKFQG | 54 | GTYYYGSALFDY |
| 5B08 | 58 | DYIMH | 59 | YINPYNDGS KYTEKFQG | 60 | GTYYYGPQLFDY |
| 5D08 | 64 | DYIMH | 65 | YINPYNDGS KYTEKFQG | 66 | GTYYYGSELFDY |

Example 3

Characterization of Affinity-Matured 8B8-Derived Antibodies 3.1 Cloning of Variable Antibody Domains into Expression Vectors The variable regions of heavy and light chain DNA sequences of the selected anti-CD19 binders were subcloned in frame with either the constant heavy chain or the constant light chain of human IgG1. In the heavy chain, Pro329Gly, Leu234Ala and Leu235Ala mutations have been introduced in order to abrogate binding to Fc gamma receptors according to the method described in International Patent Appl. Publ. No. WO 2012/130831 A1.

The cDNA and amino acid sequences of the anti-CD19 IgGs are shown in Table 9 and 10 Table 10, respectively. All antibody-encoding sequences were cloned into an expression vector, which drives transcription of the insert with a chimeric MPSV promoter and contains a synthetic polyA signal sequence located at the 3' end of the CDS. In addition, the vector contains an EBV OriP sequence for episomal maintenance of the plasmid.

TABLE 9 cDNA and amino acid sequences of
anti-CD19 clone 8B8 in P329GLALA human
IgG1 format

| SEQ ID NO: | Clone and Chain | Sequence |
|---|---|---|
| 67 | 8B8 Parental light chain | GATGCTGTGATGACCCAAACTCCACTCTCCCTGCCTG TCAGTCTTGGAGATCAAGCCTCCATCTCTTGCAGGTC TAGTCAGAGCCTTGAAAACAGTAATGGAAACACCTAT TTGAACTGGTACCTCCAGAAACCAGGCCAGTCTCCAC AACTCCTGATCTACAGGGTTTCCAAACGATTTTCTGG GGTCCTAGACAGGTTCAGTGGTAGTGGATCAGGGACA GATTTCACACTGAAAATCAGCAGAGTGGAGGCTGAGG ATTTGGGAGTTTATTTCTGCCTACAACTTACACATGT CCCGTACACGTTCGGAGGGGGGACCAAGCTGGAAATA AAACGTACGGTGGCTGCACCATCTGTCTTCATCTTCC CGCCATCTGATGAGCAGTTGAAATCTGGAACTGCCTC TGTTGTGTGCCTGCTGAATAACTTCTATCCCAGAGAG GCCAAAGTACAGTGGAAGGTGGATAACGCCCTCCAAT CGGGTAACTCCCAGGAGAGTGTCACAGAGCAGGACAG CAAGGACAGCACCTACAGCCTCAGCAGCACCCTGACG CTGAGCAAAGCAGACTACGAGAAACACAAAGTCTACG CCTGCGAAGTCACCCATCAGGGCCTGAGCTCGCCCGT CACAAAGAGCTTCAACAGGGGAGAGTGT |
| 68 | 8B8 parental heavy chain | GAGGTCCAGCTGCAGCAGTCTGGACCTGAGCTGGTAA AGCCTGGGGCTTCAGTGAAGATGGCCTGCAAGGCTTC TGGATACACATTCACTGACTATATTATGCACTGGGTG AAGCAGAAGACTGGGCAGGGCCTTGAGTGGATTGGAT ATATTAATCCTTACAATGATGGTTCTAAGTACACTGA |

TABLE 9-continued cDNA and amino acid sequences of
anti-CD19 clone 8B8 in P329GLALA human
IgG1 format

| SEQ ID NO: | Clone and Chain | Sequence |
|---|---|---|
| | | GAAGTTCAACGGCAAGGCCACACTGACTTCAGACAAA TCTTCCATCACAGCCTACATGGAGCTCAGCAGCCTGA CCTCTGAGGACTCTGCGGTCTATTACTGTGCAAGAGG GACCTATTATTATGGTAGCGCCCTCTTTGACTACTGG GGCCAAGGCACCACTCTCACAGTCTCCTCGGCTAGCA CCAAGGGCCCATCGGTCTTCCCCCTGGCACCCTCCTC CAAGAGCACCTCTGGGGGCACAGCGGCCCTGGGCTGC CTGGTCAAGGACTACTTCCCCGAACCGGTGACGGTGT CGTGGAACTCAGGCGCCCTGACCAGCGGCGTGCACAC CTTCCCGGCTGTCCTACAGTCCTCAGGACTCTACTCC CTCAGCAGCGTGGTGACCGTGCCCTCCAGCAGCTTGG GCACCCAGACCTACATCTGCAACGTGAATCACAAGCC CAGCAACACCAAGGTGGACAAGAAAGTTGAGCCCAAA TCTTGTGACAAAACTCACACATGCCCACCGTGCCCAG CACCTGAAGCTGCAGGGGGGACCGTCAGTCTTCCTCTT CCCCCCAAAACCCAAGGACACCCTCATGATCTCCCGG ACCCCTGAGGTCACATGCGTGGTGGTGGACGTGAGCC ACGAAGACCCTGAGGTCAAGTTCAACTGGTACGTGGA CGGCGTGGAGGTGCATAATGCCAAGACAAAGCCGCGG GAGGAGCAGTACAACAGCACGTACCGTGTGGTCAGCG TCCTCACCGTCCTGCACCAGGACTGGCTGAATGGCAA GGAGTACAAGTGCAAGGTCTCCAACAAAGCCCTCGGC GCCCCCATCGAGAAAACCATCTCCAAAGCCAAAGGGC AGCCCCGAGAACCACAGGTGTACACCCTGCCCCCCATC CCGGGATGAGCTGACCAAGAACCAGGTCAGCCTGACC TGCCTGGTCAAAGGCTTCTATCCCAGCGACATCGCCG TGGAGTGGGAGAGCAATGGGCAGCCGGAGAACAACTA CAAGACCACGCCTCCCGTGCTGGACTCCGACGGCTCC TTCTTCCTCTACAGCAAGCTCACCGTGGACAAGAGCA GGTGGCAGCAGGGGAACGTCTTCTCATGCTCCGTGAT GCATGAGGCTCTGCACAACCACTACACGCAGAAGAGC CTCTCCCTGTCTCCGGGTAAA |
| 69 | 8B8 Parental light chain | DIVMTQTPLSLSVTPGQPASISCKSSQSLENSNGNTY LNWYLQKPGQSPQLLIYRVSKRFSGVPDRFSGSGSGT DFTLKISRVEAEDVGVYCLQLTHVPYTFGQGTKLEI KRTVAAPSVFIFPPSDEQLKSGTASVVCLLNNFYPRE AKVQWKVDNALQSGNSQESVTEQDSKDSTYSLSSTLT LSKADYEKHKVYACEVTHQGLSSPVTKSFNRGEC |
| 70 | 8B8 parental heavy chain | QVQLVQSGAEVKKPGASVKVSCKASGYTFTDYIMHWV RQAPGQGLEWMGYINPYNDGSKYTEKFQGRVTMTSDT SISTAYMELSRLRSDDTAVYYCARGTYYYGSALFDYW GQGTTVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPK SCDKTHTCPPCPAPEAAGGPSVFLFPPKPKDTLMISR TPEVTCVVVDVSHEDPEVKFNWYVDGVEVHNAKTKPR EEQYNSTYRVVSVLTVLHQDWLNGKEYKCKVSNKALG APIEKTISKAKGQPREPQVYTLPPSRDELTKNQVSLT CLVKGFYPSDIAVEWESNGQPENNYKTTPPVLDSDGS FFLYSKLTVDKSRWQQGNVFSCSVMHEALHNHYTQKS LSLSPGK |

TABLE 10 cDNA and amino acid sequences of
affinity matured anti-CD19 clones in
P329GLALA human IgG1 format

| SEQ ID NO: | Clone and Chain | Sequence |
|---|---|---|
| 71 | 2B11 light chain | GATATTGTCATGACTCAAACTCCACTGTCTCTGTCCGTGACCCCGGGT CAGCCAGCGAGCATTTCTTGCAAATCCAGCCAATCTCTGGAAACCTCC ACCGGCACCACGTACCTGAACTGGTATCTCCAGAAACCGGGTCAGAG CCCGCAGCTGCTGATCTACCGTGTATCTAAGCGCTTCTCCGGCGTTCC TGATCGTTTCAGCGGTTCTGGATCCGGCACCGACTTTACTCTGAAAAT |

TABLE 10-continued cDNA and amino acid sequences of
affinity matured anti-CD19 clones in
P329GLALA human IgG1 format

| SEQ ID NO: | Clone and Chain | Sequence |
|---|---|---|
| | | CAGCCGTGTGGAAGCTGAAGACGTTGGCGTCTACTATTGTCTGCAGCT GCTGGAAGATCCATACACCTTCGGTCAAGGAACGAAACTGGAAATTA AACGTACGGTGGCTGCACCATCTGTCTTCATCTTCCCGCCATCTGATG AGCAGTTGAAATCTGGAACTGCCTCTGTTGTGTGCCTGCTGAATAACT TCTATCCCAGAGAGGCCAAAGTACAGTGGAAGGTGGATAACGCCCTC CAATCGGGTAACTCCCAGGAGAGTGTCACAGAGCAGGACAGCAAGG ACAGCACCTACAGCCTCAGCAGCACCCTGACGCTGAGCAAAGCAGAC TACGAGAAACACAAAGTCTACGCCTGCGAAGTCACCCATCAGGGCCT GAGCTCGCCCGTCACAAAGAGCTTCAACAGGGGAGAGTGT |
| 72 | 2B11 heavy chain | CAGGTGCAATTGGTTCAATCTGGTGCTGAAGTAAAAAAACCGGGCGC TTCCGTTAAAGTGAGCTGCAAAGCATCTGGTTACACCTTCACTGACTA TATCATGCACTGGGTTCGTCAGGCCCCGGGCCAGGGTCTGGAGTGGA TGGGCTACATTAACCCATACAACGACGGTTCCAAATATACCGAGAAA TTCCAGGGCCGCGTCACGATGACCAGCGACACTTCTATCTCCACCGCG TACATGGAACTGTCTAGACTGCGTTCTGACGACACCGCTGTTTACTAT TGTGCACGCGGTACCTACTACTACGGTCCACAGCTGTTTGATTACTGG GGCCAAGGTACCACGGTGACCGTAAGCTCTGCTAGCACCAAGGGCCC ATCGGTCTTCCCCCTGGCACCCTCCTCCAAGAGCACCTCTGGGGGCAC AGCGGCCCTGGGCTGCCTGGTCAAGGACTACTTCCCCGAACCGGTGA CGGTGTCGTGGAACTCAGGCGCCCTGACCAGCGGCGTGCACACCTTC CCGGCTGTCCTACAGTCCTCAGGACTCTACTCCCTCAGCAGCGTGGTG ACCGTGCCCTCCAGCAGCTTGGGCACCCAGACCTACATCTGCAACGT GAATCACAAGCCCAGCAACACCAAGGTGGACAAGAAAGTTGAGCCC AAATCTTGTGACAAAACTCACACATGCCCACCGTGCCCAGCACCTGA AGCTGCAGGGGGACCGTCAGTCTTCCTCTTCCCCCCAAAACCCAAGG ACACCCTCATGATCTCCCGGACCCCTGAGGTCACATGCGTGGTGGTG GACGTGAGCCACGAAGACCCTGAGGTCAAGTTCAACTGGTACGTGGA CGGCGTGGAGGTGCATAATGCCAAGACAAAGCCGCGGGAGGAGCAG TACAACAGCACGTACCGTGTGGTCAGCGTCCTCACCGTCCTGCACCA GGACTGGCTGAATGGCAAGGAGTACAAGTGCAAGGTCTCCAACAAA GCCCTCGGCGCCCCCATCGAGAAAACCATCTCCAAAGCCAAAGGGCA GCCCCGAGAACCACAGGTGTACACCCTGCCCCCATCCCGGGATGAGC TGACCAAGAACCAGGTCAGCCTGACCTGCCTGGTCAAAGGCTTCTAT CCCAGCGACATCGCCGTGGAGTGGGAGAGCAATGGGCAGCCGGAGA ACAACTACAAGACCACGCCTCCCGTGCTGGACTCCGACGGCTCCTTCT TCCTCTACAGCAAGCTCACCGTGGACAAGAGCAGGTGGCAGCAGGGG AACGTCTTCTCATGCTCCGTGATGCATGAGGCTCTGCACAACCACTAC ACGCAGAAGAGCCTCTCCCTGTCTCCGGGTAAA |
| 73 | 2B11 light chain | DIVMTQTPLSLSVTPGQPASISCKSSQSLETSTGTTYLNWYLQKPGQSPQL LIYRVSKRFSGVPDRFSGSGSGTDFTLKISRVEAEDVGVYYCLQLLEDPY TFGQGTKLEIKRTVAAPSVFIFPPSDEQLKSGTASVVCLLNNFYPREAKV QWKVDNALQSGNSQESVTEQDSKDSTYSLSSTLTLSKADYEKHKVYAC EVTHQGLSSPVTKSFNRGEC |
| 74 | 2B11 heavy chain | QVQLVQSGAEVKKPGASVKVSCKASGYTFTDYIMHWVRQAPGQGLEW MGYINPYNDGSKYTEKFQGRVTMTSDTSISTAYMELSRLRSDDTAVYYC ARGTYYYGPQLFDYWGQGTTVTVSSASTKGPSVFPLAPSSKSTSGGTAA LGCLVKDYFPEPVTVSWNSGALTSGVHTFPAVLQSSGLYSLSSVVTVPSS SLGTQTYICNVNHKPSNTKVDKKVEPKSCDKTHTCPPCPAPEAAGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALGAPIEKTISK AKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHY TQKSLSLSPGK |
| 75 | 7H07 light chain | GATATTGTTATGACTCAAACTCCACTGTCTCTGTCCGTGACCCCGGGT CAGCCAGCGAGCATTTCTTGCAAATCCAGCCAATCTCTGGAAACCTCC ACCGGCAACACGTACCTGAACTGGTATCTCCAGAAACCGGGTCAGAG CCCGCAGCTGCTGATCTACCGTGTATCTAAGCGCTTCTCCGGCGTTCC TGATCGTTTCAGCGGTTCTGGATCCGGCACCGACTTTACTCTGAAAAT CAGCCGTGTGGAAGCTGAAGACGTTGGCGTCTACTATTGTCTGCAGG CAACCCATATCCCATACACCTTCGGTCAAGGAACTAAACTGGAAATT AAACGTACGGTGGCTGCACCATCTGTCTTCATCTTCCCGCCATCTGAT GAGCAGTTGAAATCTGGAACTGCCTCTGTTGTGTGCCTGCTGAATAAC TTCTATCCCAGAGAGGCCAAAGTACAGTGGAAGGTGGATAACGCCCT CCAATCGGGTAACTCCCAGGAGAGTGTCACAGAGCAGGACAGCAAG GACAGCACCTACAGCCTCAGCAGCACCCTGACGCTGAGCAAAGCAGA CTACGAGAAACACAAAGTCTACGCCTGCGAAGTCACCCATCAGGGCC TGAGCTCGCCCGTCACAAAGAGCTTCAACAGGGGAGAGTGT |

TABLE 10-continued cDNA and amino acid sequences of
affinity matured anti-CD19 clones in
P329GLALA human IgG1 format

| SEQ ID NO: | Clone and Chain | Sequence |
|---|---|---|
| 76 | 7H07 heavy chain | CAGGTGCAATTGGTTCAATCTGGTGCTGAAGTAAAAAAACCGGGCGC TTCCGTTAAAGTGAGCTGCAAAGCATCTGGTTACACCTTCACTGACTA TATCATGCACTGGGTTCGTCAGGCCCCGGGCCAGGGTCTGGAGTGGA TGGGCTACATTAACCCATACAACGACGGTTCCAAATATACCGAGAAA TTCCAGGGCCGCGTCACGATGACCAGCGACACTTCTATCTCCACCGCG TACATGGAACTGTCTAGACTGCGTTCTGACGACACCGCTGTTTACTAT TGTGCACGCGGTACCTACTACTACGGTTCTGAACTGTTTGATTACTGG GGCCAAGGTACCACGGTGACCGTAAGCTCTGCTAGCACCAAGGGCCC ATCGGTCTTCCCCCTGGCACCCTCCTCCAAGAGCACCTCTGGGGGCAC AGCGGCCCTGGGCTGCCTGGTCAAGGACTACTTCCCCGAACCGGTGA CGGTGTCGTGGAACTCAGGCGCCCTGACCAGCGGCGTGCACACCTTC CCGGCTGTCCTACAGTCCTCAGGACTCTACTCCCTCAGCAGCGTGGTG ACCGTGCCCTCCAGCAGCTTGGGCACCCAGACCTACATCTGCAACGT GAATCACAAGCCCAGCAACACCAAGGTGGACAAGAAAGTTGAGCCC AAATCTTGTGACAAAACTCACACATGCCCACCGTGCCCAGCACCTGA AGCTGCAGGGGGACCGTCAGTCTTCCTCTTCCCCCCAAAACCCAAGG ACACCCTCATGATCTCCCGGACCCCTGAGGTCACATGCGTGGTGGTG GACGTGAGCCACGAAGACCCTGAGGTCAAGTTCAACTGGTACGTGGA CGGCGTGGAGGTGCATAATGCCAAGACAAAGCCGCGGGAGGAGCAG TACAACAGCACGTACCGTGTGGTCAGCGTCCTCACCGTCCTGCACCA GGACTGGCTGAATGGCAAGGAGTACAAGTGCAAGGTCTCCAACAAA GCCCTCGGCGCCCCCATCGAGAAAACCATCTCCAAAGCCAAAGGGCA GCCCCGAGAACCACAGGTGTACACCCTGCCCCCATCCCGGGATGAGC TGACCAAGAACCAGGTCAGCCTGACCTGCCTGGTCAAAGGCTTCTAT CCCAGCGACATCGCCGTGGAGTGGGAGAGCAATGGGCAGCCGGAGA ACAACTACAAGACCACGCCTCCCGTGCTGGACTCCGACGGCTCCTTCT TCCTCTACAGCAAGCTCACCGTGGACAAGAGCAGGTGGCAGCAGGGG AACGTCTTCTCATGCTCCGTGATGCATGAGGCTCTGCACAACCACTAC ACGCAGAAGAGCCTCTCCCTGTCTCCGGGTAAA |
| 77 | 7H07 light chain | DIVMTQTPLSLSVTPGQPASISCKSSQSLETSTGNTYLNWYLQKPGQSPQL LIYRVSKRFSGVPDRFSGSGSGTDFTLKISRVEAEDVGVYYCLQATHIPYT FGQGTKLEIKRTVAAPSVFIFPPSDEQLKSGTASVVCLLNNFYPREAKVQ WKVDNALQSGNSQESVTEQDSKDSTYSLSSTLTLSKADYEKHKVYACE VTHQGLSSPVTKSFNRGEC |
| 78 | 7H07 heavy chain | QVQLVQSGAEVKKPGASVKVSCKASGYTFTDYIMHWVRQAPGQGLEW MGYINPYNDGSKYTEKFQGRVTMTSDTSISTAYMELSRLRSDDTAVYYC ARGTYYYGSELFDYWGQGTTVTVSSASTKGPSVFPLAPSSKSTSGGTAA LGCLVKDYFPEPVTVSWNSGALTSGVHTFPAVLQSSGLYSLSSVVTVPSS SLGTQTYICNVNHKPSNTKVDKKVEPKSCDKTHTCPPCPAPEAAGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALGAPIEKTISK AKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHY TQKSLSLSPGK |
| 79 | 2B03 light chain | GATATTGTTATGACTCAAACTCCACTGTCTCTGTCCGTGACCCCGGGT CAGCCAGCGAGCATTTCTTGCAAATCCAGCCAATCTCTGGAAACCTC CACCGGCAACACGTACCTGAACTGGTATCTCCAGAAACCGGGTCAGA GCCCGCAGCTGCTGATCTACCGTGTATCTAAGCGCTTCTCCGGCGTTC CTGATCGTTTCAGCGGTTCTGGATCCGGCACCGACTTTACTCTGAAAA TCAGCCGTGTGGAAGCTGAAGACGTTGGCGTCTACTATTGTCTGCAG TTGACCCACGTTCCGTACACCTTCGGTCAAGGAANNAAAACTGGAAAT TAAACGTACGGTGGCTGCACCATCTGTCTTCATCTTCCCGCCATCTGA TGAGCAGTTGAAATCTGGAACTGCCTCTGTTGTGTGCCTGCTGAATAA CTTCTATCCCAGAGAGGCCAAAGTACAGTGGAAGGTGGATAACGCCC TCCAATCGGGTAACTCCCAGGAGAGTGTCACAGAGCAGGACAGCAA GGACAGCACCTACAGCCTCAGCAGCACCCTGACGCTGAGCAAAGCA GACTACGAGAAACACAAAGTCTACGCCTGCGAAGTCACCCATCAGGG CCTGAGCTCGCCCGTCACAAAGAGCTTCAACAGGGGAGAGTGT |
| 80 | 2B03 heavy chain | CAGGTGCAATTGGTTCAATCTGGTGCTGAAGTAAAAAAACCGGGCGC TTCCGTTAAAGTGAGCTGCAAAGCATCTGGTTACACCTTCACTGACTA TATCACGCACTGGGTTCGTCAGGCCCCGGGCCAGGGTCTGGAGTGGA TGGGCTACATTAACCCATACAACGACGGTTCCAAATATACCGAGAAA TTCCAGGGCCGCGTCACGATGACCAGCGACACTTCTATCTCCACCGCG GTACATGGAACTGTCTAGACTGCGTTCTGACGACACCGCTGTTTACTA TTGTGCACGCGGTACCTACTACTACGGTCCAGATCTGTTTGATTACTG GGGCCAAGGTACCACGGTGACCGTAAGCTCTGCTAGCACCAAGGGCC CATCGGTCTTCCCCCTGGCACCCTCCTCCAAGAGCACCTCTGGGGGCA CAGCGGCCCTGGGCTGCCTGGTCAAGGACTACTTCCCCGAACCGGTG |

TABLE 10-continued cDNA and amino acid sequences of
affinity matured anti-CD19 clones in
P329GLALA human IgG1 format

| SEQ ID NO: | Clone and Chain | Sequence |
|---|---|---|
| | | ACGGTGTCGTGGAACTCAGGCGCCCTGACCAGCGGCGTGCACACCTT |
| | | CCCGGCTGTCCTACAGTCCTCAGGACTCTACTCCCTCAGCAGCGTGGT |
| | | GACCGTGCCCTCCAGCAGCTTGGGCACCCAGACCTACATCTGCAACG |
| | | TGAATCACAAGCCCAGCAACACCAAGGTGGACAAGAAAGTTGAGCC |
| | | CAAATCTTGTGACAAAACTCACACATGCCCACCGTGCCCAGCACCTG |
| | | AAGCTGCAGGGGGACCGTCAGTCTTCCTCTTCCCCCCAAAACCCAAG |
| | | GACACCCTCATGATCTCCCGGACCCCTGAGGTCACATGCGTGGTGGT |
| | | GGACGTGAGCCACGAAGACCCTGAGGTCAAGTTCAACTGGTACGTGG |
| | | ACGGCGTGGAGGTGCATAATGCCAAGACAAAGCCGCGGGAGGAGCA |
| | | GTACAACAGCACGTACCGTGTGGTCAGCGTCCTCACCGTCCTGCACC |
| | | AGGACTGGCTGAATGGCAAGGAGTACAAGTGCAAGGTCTCCAACAA |
| | | AGCCCTCGGCGCCCCCATCGAGAAAACCATCTCCAAAGCCAAAGGGC |
| | | AGCCCCGAGAACCACAGGTGTACACCCTGCCCCCATCCCGGGATGAG |
| | | CTGACCAAGAACCAGGTCAGCCTGACCTGCCTGGTCAAAGGCTTCTA |
| | | TCCCAGCGACATCGCCGTGGAGTGGGAGAGCAATGGGCAGCCGGAG |
| | | AACAACTACAAGACCACGCCTCCCGTGCTGGACTCCGACGGCTCCTT |
| | | CTTCCTCTACAGCAAGCTCACCGTGGACAAGAGCAGGTGGCAGCAGG |
| | | GGAACGTCTTCTCATGCTCCGTGATGCATGAGGCTCTGCACAACCACT |
| | | ACACGCAGAAGAGCCTCTCCCTGTCTCCGGGTAAA |
| 81 | 2B03 light chain | DIVMTQTPLSLSVTPGQPASISCKSSQSLETSTGNTYLNWYLQKPGQSPQ |
| | | LLIYRVSKRFSGVPDRFSGSGSGTDFTLKISRVEAEDVGVYYCLQLTHVP |
| | | YTFGQGXKLEIKRTVAAPSVFIFPPSDEQLKSGTASVVCLLNNFYPREAK |
| | | VQWKVDNALQSGNSQESVTEQDSKDSTYSLSSTLTLSKADYEKHKVYA |
| | | CEVTHQGLSSPVTKSFNRGEC |
| 82 | 2B03 heavy chain | QVQLVQSGAEVKKPGASVKVSCKASGYTFTDYITHWVRQAPGQGLEW |
| | | MGYINPYNDGSKYTEKFQGRVTMTSDTSISTAYMELSRLRSDDTAVYYC |
| | | ARGTYYYGPDLFDYWGQGTTVTVSSASTKGPSVFPLAPSSKSTSGGTAA |
| | | LGCLVKDYFPEPVTVSWNSGALTSGVHTFPAVLQSSGLYSLSSVVTVPSS |
| | | SLGTQTYICNVNHKPSNTKVDKKVEPKSCDKTHTCPPCPAPEAAGGPSV |
| | | FLFPPKPKDTLMISRTPEVTCVVVDVSHEDPEVKFNWYVDGVEVHNAKT |
| | | KPREEQYNSTYRVVSVLTVLHQDWLNGKEYKCKVSNKALGAPIEKTISK |
| | | AKGQPREPQVYTLPPSRDELTKNQVSLTCLVKGFYPSDIAVEWESNGQP |
| | | ENNYKTTPPVLDSDGSFFLYSKLTVDKSRWQQGNVFSCSVMHEALHNH |
| | | YTQKSLSLSPGK |
| 83 | 5A07 light chain | GATATTGTTATGACTCAAACTCCACTGTCTCTGTCCGTGACCCCCGGGT |
| | | CAGCCAGCGAGCATTTCTTGCAAATCCAGCCAATCTCTGGAAACCTC |
| | | CACCGGCAACACGTACCTGAACTGGTATCTCCAGAAACCGGGTCAGA |
| | | GCCCGCAGCTGCTGATCTACCGTGTATCTAAGCGCTTCTCCGGCGTTC |
| | | CTGATCGTTTCAGCGGTTCTGGATCCGGCACCGACTTTACTCTGAAAA |
| | | TCAGCCGTGTGGAAGCTGAAGACGTTGGCGTCTACTATTGTCTGCAG |
| | | CCAGGTCATTACCCAGGTACCTTCGGTCAAGGAACTAAACTGGAAAT |
| | | TAAACGTACGGTGGCTGCACCATCTGTCTTCATCTTCCCGCCATCTGA |
| | | TGAGCAGTTGAAATCTGGAACTGCCTCTGTTGTGTGCCTGCTGAATAA |
| | | CTTCTATCCCAGAGAGGCCAAAGTACAGTGGAAGGTGGATAACGCCC |
| | | TCCAATCGGGTAACTCCCAGGAGAGTGTCACAGAGCAGGACAGCAA |
| | | GGACAGCACCTACAGCCTCAGCAGCACCCTGACGCTGAGCAAAGCA |
| | | GACTACGAGAAACACAAAGTCTACGCCTGCGAAGTCACCCATCAGGG |
| | | CCTGAGCTCGCCCGTCACAAAGAGCTTCAACAGGGGAGAGTGT |
| 84 | 5A07 heavy chain | CAGGTGCAATTGGTTCAATCTGGTGCTGAAGTAAAAAAACCGGGCGC |
| | | TTCCGTTAAAGTGAGCTGCAAAGCATCTGGTTACACCTTCACTGACTA |
| | | TATCATGCACTGGGTTCGTCAGGCCCCGGGCCAGGGTCTGGAGTGGA |
| | | TGGGCTACATTAACCCATACAACGACGGTTCCAAATATACCGAGAAA |
| | | TTCCAGGGCCGCGTCACGATGACCAGCGACACTTCTATCTCCACCGC |
| | | GTACATGGAACTGTCTAGACTGCGTTCTGACGACACCGCTGTTTACTA |
| | | TTGTGCACGCGGTACTTACTACTACGGTCCGCCCTCTTTGATTACTG |
| | | GGGCCAAGGTACCACGGTGACCGTAAGCTCTGCTAGCACCAAGGGCC |
| | | CATCGGTCTTCCCCCTGGCACCCTCCTCCAAGAGCACCTCTGGGGGCA |
| | | CAGCGGCCCTGGGCTGCCTGGTCAAGGACTACTTCCCCGAACCGGTG |
| | | ACGGTGTCGTGGAACTCAGGCGCCCTGACCAGCGGCGTGCACACCTT |
| | | CCCGGCTGTCCTACAGTCCTCAGGACTCTACTCCCTCAGCAGCGTGGT |
| | | GACCGTGCCCTCCAGCAGCTTGGGCACCCAGACCTACATCTGCAACG |
| | | TGAATCACAAGCCCAGCAACACCAAGGTGGACAAGAAAGTTGAGCC |
| | | CAAATCTTGTGACAAAACTCACACATGCCCACCGTGCCCAGCACCTG |
| | | AAGCTGCAGGGGGACCGTCAGTCTTCCTCTTCCCCCCAAAACCCAAG |
| | | GACACCCTCATGATCTCCCGGACCCCTGAGGTCACATGCGTGGTGGT |
| | | GGACGTGAGCCACGAAGACCCTGAGGTCAAGTTCAACTGGTACGTGG |
| | | ACGGCGTGGAGGTGCATAATGCCAAGACAAAGCCGCGGGAGGAGCA |
| | | GTACAACAGCACGTACCGTGTGGTCAGCGTCCTCACCGTCCTGCACC |

TABLE 10-continued cDNA and amino acid sequences of
affinity matured anti-CD19 clones in
P329GLALA human IgG1 format

| SEQ ID NO: | Clone and Chain | Sequence |
|---|---|---|
| | | AGGACTGGCTGAATGGCAAGGAGTACAAGTGCAAGGTCTCCAACAA<br>AGCCCTCGGCGCCCCCATCGAGAAAACCATCTCCAAAGCCAAAGGGC<br>AGCCCCGAGAACCACAGGTGTACACCCTGCCCCCATCCCGGGATGAG<br>CTGACCAAGAACCAGGTCAGCCTGACCTGCCTGGTCAAAGGCTTCTA<br>TCCCAGCGACATCGCCGTGGAGTGGGAGAGCAATGGGCAGCCGGAG<br>AACAACTACAAGACCACGCCTCCCGTGCTGGACTCCGACGGCTCCTT<br>CTTCCTCTACAGCAAGCTCACCGTGGACAAGAGCAGGTGGCAGCAGG<br>GGAACGTCTTCTCATGCTCCGTGATGCATGAGGCTCTGCACAACCACT<br>ACACGCAGAAGAGCCTCTCCCTGTCTCCGGGTAAA |
| 85 | 5A07 light chain | DIVMTQTPLSLSVTPGQPASISCKSSQSLETSTGNTYLNWYLQKPGQSPQ<br>LLIYRVSKRFSGVPDRFSGSGSGTDFTLKISRVEAEDVGVYYCLQPGHYP<br>GTFGQGTKLEIKRTVAAPSVFIFPPSDEQLKSGTASVVCLLNNFYPREAK<br>VQWKVDNALQSGNSQESVTEQDSKDSTYSLSSTLTLSKADYEKHKVYA<br>CEVTHQGLSSPVTKSFNRGEC |
| 86 | 5A07 heavy chain | QVQLVQSGAEVKKPGASVKVSCKASGYTFTDYIMHWVRQAPGQGLEW<br>MGYINPYNDGSKYTEKFQGRVTMTSDTSISTAYMELSRLRSDDTAVYYC<br>ARGTYYYGSALFDYWGQGTTVTVSSASTKGPSVFPLAPSSKSTSGGTAA<br>LGCLVKDYFPEPVTVSWNSGALTSGVHTFPAVLQSSGLYSLSSVVTVPSS<br>SLGTQTYICNVNHKPSNTKVDKKVEPKSCDKTHTCPPCPAPEAAGGPSV<br>FLFPPKPKDTLMISRTPEVTCVVVDVSHEDPEVKFNWYVDGVEVHNAKT<br>KPREEQYNSTYRVVSVLTVLHQDWLNGKEYKCKVSNKALGAPIEKTISK<br>AKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNH<br>YTQKSLSLSPGK |
| 87 | 5D08 light chain | GATATTGTTATGACTCAAACTCCACTGTCTCTGTCCGTGACCCCGGGT<br>CAGCCAGCGAGCATTTCTTGCAAATCCAGCCAATCTCTGGAAACCTC<br>CACCGGCAACACGTACCTGAACTGGTATCTCCAGAAACCGGGTCAGA<br>GCCCGCAGCTGCTGATCTACCGTGTATCTAAGCGCTTCTCCGGCGTTC<br>CTGATCGTTTCAGCGGTTCTGGATCCGGCACCGACTTTACTCTGAAAA<br>TCAGCCGTGTGGAAGCTGAAGACGTTGGCGTCTACTATTGTCTGCAG<br>CTGACCCATGAACCATACACCTTCGGTCAAGGAACTAAACTGGAAAT<br>TAAACGTACGGTGGCTGCACCATCTGTCTTCATCTTCCCGCCATCTGA<br>TGAGCAGTTGAAATCTGGAACTGCCTCTGTTGTGTGCCTGCTGAATAA<br>CTTCTATCCCAGAGAGGCCAAAGTACAGTGGAAGGTGGATAACGCCC<br>TCCAATCGGGTAACTCCCAGGAGAGTGTCACAGAGCAGGACAGCAA<br>GGACAGCACCTACAGCCTCAGCAGCACCCTGACGCTGAGCAAAGCA<br>GACTACGAGAAACACAAAGTCTACGCCTGCGAAGTCACCCATCAGGG<br>CCTGAGCTCGCCCGTCACAAAGAGCTTCAACAGGGGAGAGTGT |
| 88 | 5D08 heavy chain | CAGGTGCAATTGGTTCAATCTGGTGCTGAAGTAAAAAAACCGGGCGC<br>TTCCGTTAAAGTGAGCTGCAAAGCATCTGGTTACACCTTCACTGACTA<br>TATCATGCACTGGGTTCGTCAGGCCCCGGGCCAGGGTCTGGAGTGGA<br>TGGGCTACATTAACCCATACAACGACGGTTCCAAATATACCGAGAAA<br>TTCCAGGGCCGCGTCACGATGACCAGCGACACTTCTATCTCCACCGC<br>GTACATGGAACTGTCTAGACTGCGTTCTGACGACACCGCTGTTTACTA<br>TTGTGCACGCGGTACCTACTACTACGGTTCTGAACTGTTTGATTACTG<br>GGGCCAAGGTACCACGGTGACCGTAAGCTCTGCTAGCACCAAGGGCC<br>CATCGGTCTTCCCCCTGGCACCCTCCTCCAAGAGCACCTCTGGGGGCA<br>CAGCGGCCCTGGGCTGCCTGGTCAAGGACTACTTCCCCGAACCGGTG<br>ACGGTGTCGTGGAACTCAGGCGCCCTGACCAGCGGCGTGCACACCTT<br>CCCGGCTGTCCTACAGTCCTCAGGACTCTACTCCCTCAGCAGCGTGGT<br>GACCGTGCCCTCCAGCAGCTTGGGCACCCAGACCTACATCTGCAACG<br>TGAATCACAAGCCCAGCAACACCAAGGTGGACAAGAAAGTTGAGCC<br>CAAATCTTGTGACAAAACTCACACATGCCCACCGTGCCCAGCACCTG<br>AAGCTGCAGGGGGACCGTCAGTCTTCCTCTTCCCCCCAAAACCCAAG<br>GACACCCTCATGATCTCCCGGACCCCTGAGGTCACATGCGTGGTGGT<br>GGACGTGAGCCACGAAGACCCTGAGGTCAAGTTCAACTGGTACGTGG<br>ACGGCGTGGAGGTGCATAATGCCAAGACAAAGCCGCGGGAGGAGCA<br>GTACAACAGCACGTACCGTGTGGTCAGCGTCCTCACCGTCCTGCACC<br>AGGACTGGCTGAATGGCAAGGAGTACAAGTGCAAGGTCTCCAACAA<br>AGCCCTCGGCGCCCCCATCGAGAAAACCATCTCCAAAGCCAAAGGGC<br>AGCCCCGAGAACCACAGGTGTACACCCTGCCCCCATCCCGGGATGAG<br>CTGACCAAGAACCAGGTCAGCCTGACCTGCCTGGTCAAAGGCTTCTA<br>TCCCAGCGACATCGCCGTGGAGTGGGAGAGCAATGGGCAGCCGGAG<br>AACAACTACAAGACCACGCCTCCCGTGCTGGACTCCGACGGCTCCTT<br>CTTCCTCTACAGCAAGCTCACCGTGGACAAGAGCAGGTGGCAGCAGG<br>GGAACGTCTTCTCATGCTCCGTGATGCATGAGGCTCTGCACAACCACT<br>ACACGCAGAAGAGCCTCTCCCTGTCTCCGGGTAAA |

TABLE 10-continued cDNA and amino acid sequences of
affinity matured anti-CD19 clones in
P329GLALA human IgG1 format

| SEQ ID NO: | Clone and Chain | Sequence |
|---|---|---|
| 89 | 5D08 light chain | DIVMTQTPLSLSVTPGQPASISCKSSQSLETSTGNTYLNWYLQKPGQSPQ<br>LLIYRVSKRFSGVPDRFSGSGSGTDFTLKISRVEAEDVGVYYCLQLTHEP<br>YTFGQGTKLEIKRTVAAPSVFIFPPSDEQLKSGTASVVCLLNNFYPREAK<br>VQWKVDNALQSGNSQESVTEQDSKDSTYSLSSTLTLSKADYEKHKVYA<br>CEVTHQGLSSPVTKSFNRGEC |
| 90 | 5D08 heavy chain | QVQLVQSGAEVKKPGASVKVSCKASGYTFTDYIMHWVRQAPGQGLEW<br>MGYINPYNDGSKYTEKFQGRVTMTSDTSISTAYMELSRLRSDDTAVYYC<br>ARGTYYYGSELFDYWGQGTTVTVSSASTKGPSVFPLAPSSKSTSGGTAA<br>LGCLVKDYFPEPVTVSWNSGALTSGVHTFPAVLQSSGLYSLSSVVTVPSS<br>SLGTQTYICNVNHKPSNTKVDKKVEPKSCDKTHTCPPCPAPEAAGGPSV<br>FLFPPKPKDTLMISRTPEVTCVVVDVSHEDPEVKFNWYVDGVEVHNAKT<br>KPREEQYNSTYRVVSVLTVLHQDWLNGKEYKCKVSNKALGAPIEKTISK<br>AKGQPREPQVYTLPPSRDELTKNQVSLTCLVKGFYPSDIAVEWESNGQP<br>ENNYKTTPPVLDSDGSFFLYSKLTVDKSRWQQGNVFSCSVMHEALHNH<br>YTQKSLSLSPGK |
| 91 | 5B08 light chain | GATATTGTTATGACTCAAACTCCACTGTCTCTGTCCGTGACCCCGGGT<br>CAGCCAGCGAGCATTTCTTGCAAATCCAGCCAATCTCTGGAAACCTC<br>CACCGGCAACACGTACCTGAACTGGTATCTCCAGAAACCGGGTCAGA<br>GCCCGCAGCTGCTGATCTACCGTGTATCTAAGCGCTTCTCCGGCGTTC<br>CTGATCGTTTCAGCGGTTCTGGATCCGGCACCGACTTTACTCTGAAAA<br>TCAGCCGTGTGGAAGCTGAAGACGTTGGCGTCTACTATTGTCTGCAG<br>CTGGATTCTTACCCAAACACCTTCGGTCAAGGAACTAAACTGGAAAT<br>TAAACGTACGGTGGCTGCACCATCTGTCTTCATCTTCCCGCCATCTGA<br>TGAGCAGTTGAAATCTGGAACTGCCTCTGTTGTGTGCCTGCTGAATAA<br>CTTCTATCCCAGAGAGGCCAAAGTACAGTGGAAGGTGGATAACGCCC<br>TCCAATCGGGTAACTCCCAGGAGAGTGTCACAGAGCAGGACAGCAA<br>GGACAGCACCTACAGCCTCAGCAGCACCCTGACGCTGAGCAAAGCA<br>GACTACGAGAAACACAAAGTCTACGCCTGCGAAGTCACCCATCAGGG<br>CCTGAGCTCGCCCGTCACAAAGAGCTTCAACAGGGGGAGAGTGT |
| 92 | 5B08 heavy chain | CAGGTGCAATTGGTTCAATCTGGTGCTGAAGTAAAAAAACCGGGCGC<br>TTCCGTTAAAGTGAGCTGCAAAGCATCTGGTTACACCTTCACTGACTA<br>TATCATGCACTGGGTTCGTCAGGCCCCGGGCCAGGGTCTGGAGTGGA<br>TGGGCTACATTAACCCATACAACGACGGTTCCAAATATACCGAGAAA<br>TTCCAGGGCCGCGTCACGATGACCAGCGACACTTCTATCTCCACCGC<br>GTACATGGAACTGTCTAGACTGCGTTCTGACGACACCGCTGTTTACTA<br>TTGTGCACGCGGTACCTACTACTACGGTCCACAGCTGTTTGATTACTG<br>GGGCCAAGGTACCACGGTGACCGTAAGCTCTGCTAGCACCAAGGGCC<br>CATCGGTCTTCCCCCTGGCACCCTCCTCCAAGAGCACCTCTGGGGGCA<br>CAGCGGCCCTGGGCTGCCTGGTCAAGGACTACTTCCCCGAACCGGTG<br>ACGGTGTCGTGGAACTCAGGCGCCCTGACCAGCGGCGTGCACACCTT<br>CCCGGCTGTCCTACAGTCCTCAGGACTCTACTCCCTCAGCAGCGTGGT<br>GACCGTGCCCTCCAGCAGCTTGGGCACCCAGACCTACATCTGCAACG<br>TGAATCACAAGCCCAGCAACACCAAGGTGGACAAGAAAGTTGAGCC<br>CAAATCTTGTGACAAAACTCACACATGCCCACCGTGCCCAGCACCTG<br>AAGCTGCAGGGGGACCGTCAGTCTTCCTCTTCCCCCCAAAACCCAAG<br>GACACCCTCATGATCTCCCGGACCCCTGAGGTCACATGCGTGGTGGT<br>GGACGTGAGCCACGAAGACCCTGAGGTCAAGTTCAACTGGTACGTGG<br>ACGGCGTGGAGGTGCATAATGCCAAGACAAAGCCGCGGGAGGAGCA<br>GTACAACAGCACGTACCGTGTGGTCAGCGTCCTCACCGTCCTGCACC<br>AGGACTGGCTGAATGGCAAGGAGTACAAGTGCAAGGTCTCCAACAA<br>AGCCCTCGGCGCCCCCATCGAGAAAACCATCTCCAAAGCCAAAGGGC<br>AGCCCCGAGAACCACAGGTGTACACCCTGCCCCCATCCCGGGATGAG<br>CTGACCAAGAACCAGGTCAGCCTGACCTGCCTGGTCAAAGGCTTCTA<br>TCCCAGCGACATCGCCGTGGAGTGGGAGAGCAATGGGCAGCCGGAG<br>AACAACTACAAGACCACGCCTCCCGTGCTGGACTCCGACGGCTCCTT<br>CTTCCTCTACAGCAAGCTCACCGTGGACAAGAGCAGGTGGCAGCAGG<br>GGAACGTCTTCTCATGCTCCGTGATGCATGAGGCTCTGCACAACCACT<br>ACACGCAGAAGAGCCTCTCCCTGTCTCCGGGTAAA |
| 93 | 5B08 light chain | DIVMTQTPLSLSVTPGQPASISCKSSQSLETSTGNTYLNWYLQKPGQSPQ<br>LLIYRVSKRFSGVPDRFSGSGSGTDFTLKISRVEAEDVGVYYCLQLDSYP<br>NTFGQGTKLEIKRTVAAPSVFIFPPSDEQLKSGTASVVCLLNNFYPREAK<br>VQWKVDNALQSGNSQESVTEQDSKDSTYSLSSTLTLSKADYEKHKVYA<br>CEVTHQGLSSPVTKSFNRGEC |
| 94 | 5B08 heavy chain | QVQLVQSGAEVKKPGASVKVSCKASGYTFTDYIMHWVRQAPGQGLEW<br>MGYINPYNDGSKYTEKFQGRVTMTSDTSISTAYMELSRLRSDDTAVYYC<br>ARGTYYYGPQLFDYWGQGTTVTVSSASTKGPSVFPLAPSSKSTSGGTAA<br>LGCLVKDYFPEPVTVSWNSGALTSGVHTFPAVLQSSGLYSLSSVVTVPSS |

TABLE 10-continued cDNA and amino acid sequences of
affinity matured anti-CD19 clones in
P329GLALA human IgG1 format

| SEQ ID NO: | Clone and Chain | Sequence |
|---|---|---|
| | | SLGTQTYICNVNHKPSNTKVDKKVEPKSCDKTHTCPPCPAPEAAGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALGAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK |
| 95 | 5H09 light chain | GATATTGTTATGACTCAAACTCCACTGTCTCTGTCCGTGACCCCGGGT CAGCCAGCGAGCATTTCTTGCAAATCCAGCCAATCTCTGGAATCTTCC ACCGGCAACACGTACCTGAACTGGTATCTCCAGAAACCGGGTCAGAG CCCGCAGCTGCTGATCTACCGTGTATCTAAGCGCTTCTCCGGCGTTCC TGATCGTTTCAGCGGTTCTGGATCCGGCACCGACTTTACTCTGAAAAT CAGCCGTGTGGAAGCTGAAGACGTTGGCGTCTACTATTGTCTGCAGC TGATCGATTACCCAGTTACCTTCGGTCAAGGAACTAAACTGGAAATT AAACGTACGGTGGCTGCACCATCTGTCTTCATCTTCCCGCCATCTGAT GAGCAGTTGAAATCTGGAACTGCCTCTGTTGTGTGCCTGCTGAATAA CTTCTATCCCAGAGAGGCCAAAGTACAGTGGAAGGTGGATAACGCCC TCCAATCGGGTAACTCCCAGGAGAGTGTCACAGAGCAGGACAGCAA GGACAGCACCTACAGCCTCAGCAGCACCCTGACGCTGAGCAAAGCA GACTACGAGAAACACAAAGTCTACGCCTGCGAAGTCACCCATCAGGG CCTGAGCTCGCCCGTCACAAAGAGCTTCAACAGGGGAGAGTGT |
| 96 | 5H09 heavy chain | CAGGTGCAATTGGTTCAATCTGGTGCTGAAGTAAAAAAACCGGGCGC TTCCGTTAAAGTGAGCTGCAAAGCATCTGGTTACACCTTCACTGACTA TATCATGCACTGGGTTCGTCAGGCCCCGGGCCAGGGTCTGGAGTGGA TGGGCTACATTAACCCATACAACGACGGTTCCAAATATACCGAGAAA TTCCAGGGCCGCGTCACGATGACCAGCGACACTTCTATCTCCACCGC GTACATGGAACTGTCTAGACTGCGTTCTGACGACACCGCTGTTTACTA TTGTGCACGCGGTACCTACTACTACGGTTCTGCACTGTTTGATTACTG GGGCCAAGGTACCACGGTGACCGTAAGCTCTGCTAGCACCAAGGGCC CATCGGTCTTCCCCCTGGCACCCTCCTCCAAGAGCACCTCTGGGGGCA CAGCGGCCCTGGGCTGCCTGGTCAAGGACTACTTCCCCGAACCGGTG ACGGTGTCGTGGAACTCAGGCGCCCTGACCAGCGGCGTGCACACCTT CCCGGCTGTCCTACAGTCCTCAGGACTCTACTCCCTCAGCAGCGTGGT GACCGTGCCCTCCAGCAGCTTGGGCACCCAGACCTACATCTGCAACG TGAATCACAAGCCCAGCAACACCAAGGTGGACAAGAAAGTTGAGCC CAAATCTTGTGACAAAACTCACACATGCCCACCGTGCCCAGCACCTG AAGCTGCAGGGGGACCGTCAGTCTTCCTCTTCCCCCCAAAACCCAAG GACACCCTCATGATCTCCCGGACCCCTGAGGTCACATGCGTGGTGGT GGACGTGAGCCACGAAGACCCTGAGGTCAAGTTCAACTGGTACGTGG ACGGCGTGGAGGTGCATAATGCCAAGACAAAGCCGCGGGAGGAGCA GTACAACAGCACGTACCGTGTGGTCAGCGTCCTCACCGTCCTGCACC AGGACTGGCTGAATGGCAAGGAGTACAAGTGCAAGGTCTCCAACAA AGCCCTCGGCGCCCCCATCGAGAAAACCATCTCCAAAGCCAAAGGGC AGCCCCGAGAACCACAGGTGTACACCCTGCCCCCATCCCGGGATGAG CTGACCAAGAACCAGGTCAGCCTGACCTGCCTGGTCAAAGGCTTCTA TCCCAGCGACATCGCCGTGGAGTGGGAGAGCAATGGGCAGCCGGAG AACAACTACAAGACCACGCCTCCCGTGCTGGACTCCGACGGCTCCTT CTTCCTCTACAGCAAGCTCACCGTGGACAAGAGCAGGTGGCAGCAGG GGAACGTCTTCTCATGCTCCGTGATGCATGAGGCTCTGCACAACCACT ACACGCAGAAGAGCCTCTCCCTGTCTCCGGGTAAA |
| 97 | 5H09 light chain | DIVMTQTPLSLSVTPGQPASISCKSSQSLESSTGNTYLNWYLQKPGQSPQ LLIYRVSKRFSGVPDRFSGSGSGTDFTLKISRVEAEDVGVYYCLQLIDYP VTFGQGTKLEIKRTVAAPSVFIFPPSDEQLKSGTASVVCLLNNFYPREAK VQWKVDNALQSGNSQESVTEQDSKDSTYSLSSTLTLSKADYEKHKVYA CEVTHQGLSSPVTKSFNRGEC |
| 98 | 5H09 heavy chain | QVQLVQSGAEVKKPGASVKVSCKASGYTFTDYIMHWVRQAPGQGLEW MGYINPYNDGSKYTEKFQGRVTMTSDTSISTAYMELSRLRSDDTAVYYC ARGTYYYGSALFDYWGQGTTVTVSSASTKGPSVFPLAPSSKSTSGGTAA LGCLVKDYFPEPVTVSWNSGALTSGVHTFPAVLQSSGLYSLSSVVTVPSS SLGTQTYICNVNHKPSNTKVDKKVEPKSCDKTHTCPPCPAPEAAGGPSV FLFPPKPKDTLMISRTPEVTCVVVDVSHEDPEVKFNWYVDGVEVHNAKT KPREEQYNSTYRVVSVLTVLHQDWLNGKEYKCKVSNKALGAPIEKTISK AKGQPREPQVYTLPPSRDELTKNQVSLTCLVKGFYPSDIAVEWESNGQP ENNYKTTPPVLDSDGSFFLYSKLTVDKSRWQQGNVFSCSVMHEALHNH YTQKSLSLSPGK |

3.2 Affinity Determination of Selected Antibodies by SPR

For the exact determination of the affinities by SPR, the selected anti-CD19 antibodies were produced by co-transfecting HEK293-EBNA cells with the mammalian expression vectors using polyethylenimine. The cells were transfected with the corresponding expression vectors in a 1:1 ratio ("vector heavy chain": "vector light chain") according to the standard procedure. 7 days after transfection, the antibody titer in the supernatant was measured and all titers were equilibrated to 10 µg/ml.

The Affinity ($K_D$) of the parental antibody 8B8 as well as it derivatives was measured by SPR using a ProteOn XPR36 instrument (Biorad) at 25° C. 7000 RU of polyclonal anti-human Fab antibody were immobilized on all 6 channels of a GLM chip by Amine coupling (NaAcetate pH4.5, 25 ul/min, 240 s) (vertical orientation). Each antibody-containing HEK supernatant was filtered, diluted with PBST (10 mM phosphate, 150 mM sodium chloride pH 7.4, 0.005% Tween 20) to a concentration of 10 ug/ml, and then injected at a for 360 s at 25 µl/minute to achieve immobilization levels between 500 and 800 response units (RU) in vertical orientation. Injection of monomeric CD19-Fc: For one-shot kinetics measurements, injection direction was changed to horizontal orientation, three-fold dilution series of purified monomeric CD19-Fc (varying concentration ranges between 150 and 6 nM) were injected simultaneously at 50 µl/min along separate channels 1-4, with association times of 180 s, and dissociation times of 300 s. A human IgG Fc fragment (150 nM) was injected in channel 5 as a negative control for specific binding to monomeric CD19-Fc. Buffer (PB ST) was injected along the sixth channel to provide an "in-line" blank for referencing. An overview of the respective sensorgrams is shown in FIGS. 4A to 4H. Regeneration was performed by two pulses of 10 mM glycine pH 1.5 and 50 mM NaOH for 30 s at 90 ul/min (vertical orientation). Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. A summary of the kinetic and thermodynamic data is shown in Table 11. The dissociation constant of all affinity-matured clones was improved compared to their parental clone 8B8.

TABLE 11

Summary of the kinetic and thermodynamic data for the interaction between anti-CD19 huIgG1 and human CD19

| clone | ka (1/Ms) | kd (1/s) | KD (M) |
|---|---|---|---|
| Parental 8B8 | 5.66E+4 | 1.34E−4 | 2.36E−9 |
| 5H09 | 7.91E+4 | 1.50E−5 | 1.89E−10 |
| 7H07 | 7.45E+4 | 5.57E−5 | 7.47E−10 |
| 2B03 | 6.02E+4 | 5.00E−5 | 8.31E−10 |
| 2B11 | 6.34E+4 | 3.14E−5 | 4.95E−10 |
| 5A07 | 6.98E+4 | 3.07E−5 | 4.40E−10 |
| 5B08 | 6.81E+4 | 5.26E−5 | 7.72E−10 |
| 5D08 | 8.88E+4 | 8.44E−5 | 9.51E−10 |

Example 4

Preparation and Purification of Anti-CD19 IgG1 P329G LALA

The selected anti-CD19 antibodies were produced by co-transfecting HEK293-EBNA cells with the mammalian expression vectors using polyethylenimine. The cells were transfected with the corresponding expression vectors in a 1:1 ratio ("vector heavy chain": "vector light chain").

For the production in 500 mL shake flasks, 400 million HEK293 EBNA cells were seeded 24 hours before transfection. Before the transfection, cells were centrifuged for 5 minutes at 210×g, and the supernatant was replaced by pre-warmed CD CHO medium. Expression vectors (200 µg of total DNA) were mixed in 20 mL CD CHO medium. After addition of 540 µL PEI, the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% CO2 atmosphere. After the incubation, 160 mL of F17 medium was added and cells were cultured for 24 hours. One day after transfection 1 mM valproic acid and 7% Feed with supplements were added. After culturing for 7 days, the supernatant was collected by centrifugation for 15 minutes at 210×g. The solution was sterile filtered (0.22 µm filter), supplemented with sodium azide to a final concentration of 0.01% (w/v), and kept at 4° C.

Purification of antibody molecules from cell culture supernatants was carried out by affinity chromatography using Protein A as described above for purification of antigen Fc fusions. The protein was concentrated and filtered prior to loading on a HiLoad Superdex 200 column (GE Healthcare) equilibrated with 20 mM Histidine, 140 mM NaCl solution of pH 6.0.

The protein concentration of purified antibodies was determined by measuring the OD at 280 nm, using the molar extinction coefficient calculated on the basis of the amino acid sequence. Purity and molecular weight of the antibodies were analyzed by CE-SDS in the presence and absence of a reducing agent (Invitrogen, USA) using a LabChipGXII (Caliper). The aggregate content of antibody samples was analyzed using a TSKgel G3000 SW XL analytical size-exclusion column (Tosoh) equilibrated in a 25 mM $K_2HPO_4$, 125 mM NaCl, 200 mM L-Arginine Monohydrocloride, 0.02% (w/v) $NaN_3$, pH 6.7 running buffer at 25° C. (Table 12).

TABLE 12

Biochemical analysis of anti-CD19 P329G LALA IgG1 clones

| Clone | Yield [mg/l] | Monomer [%] | CE-SDS (non red) |
|---|---|---|---|
| Parental 8B8 | 25.3 | 100 | 99.1 |
| 2B11 | 35.4 | 100 | 98.4 |
| 7H07 | 89.8 | 100 | 99.4 |
| 2B03 | 182 | 100 | 100 |
| 5A07 | 90.2 | 100 | 99.4 |
| 5D08 | 90.2 | 100 | 99.3 |
| 5B08 | 24.1 | 99.6 | 100 |
| 5H09 | 29.9 | 100 | 98.1 |

For the preparation of bispecific constructs clone 2B11 was chosen because it lacks the three deamidation hotspots.

Example 5

Binding on CD19-Expressing Tumor Cells

To check the binding of the IgG1 clones to CD19-expressing cells, the WSU-DLCL2 cells (DSMZ No. ACC 575) derived from the pleural effusion of a 41-year-old Caucasian man with B-cell non-Hodgkin lymphoma were used. $0.1 \times 10^6$ tumor cells resuspended in DPBS (Gibco by Life Technologies, Cat. No. 14190 326) were added to each well of a round-bottom suspension cell 96-well plate (greiner bio-one, cellstar, Cat. No. 650185). Cells were washed once with 200 µL DPBS. Cells were resuspended in 100 µL/well of 4° C. cold DPBS buffer containing 1:5000 diluted Fixable Viability Dye eFluor 660 (eBioscience, Cat. No. 65-0864-18) and plates were incubated for 30 minutes at 4° C. Cells were washed once with 200 µL/well 4° C. cold DPBS buffer and resuspended in 50 µL/well of 4° C. cold FACS buffer (DPBS supplied with 2% FBS, 5 mM EDTA pH8 (Amresco, Cat. No. E177) and 7.5 mM Sodium azide (Sigma-Aldrich S2002)) containing the CD19 binders at a series of concentrations, followed by incubation for 1 hour at 4° C. After extensive washing, cells were further stained with 50 µL/well of 4° C. cold FACS buffer containing 5 µg/mL PE-conjugated AffiniPure anti-human IgG F(ab')2-fragment-specific goat F(ab')2 fragment (Jackson ImmunoResearch, Cat. No. 109 116 098) for 30 minutes at 4° C. Cells were then washed twice with 200 µL/well 4° C. FACS buffer and cells were fixed in 50 µL/well DPBS containing 1% Formaldehyde (Sigma, HT501320-9.5L). Cells were resuspended in 100 µL/well FACS-buffer and acquired using the FACS LSR II (BD Biosciences). Data was analyzed using FlowJo V10 (FlowJo, LLC) and GraphPad Prism 6.04 (GraphPad Software, Inc).

Figure 5:
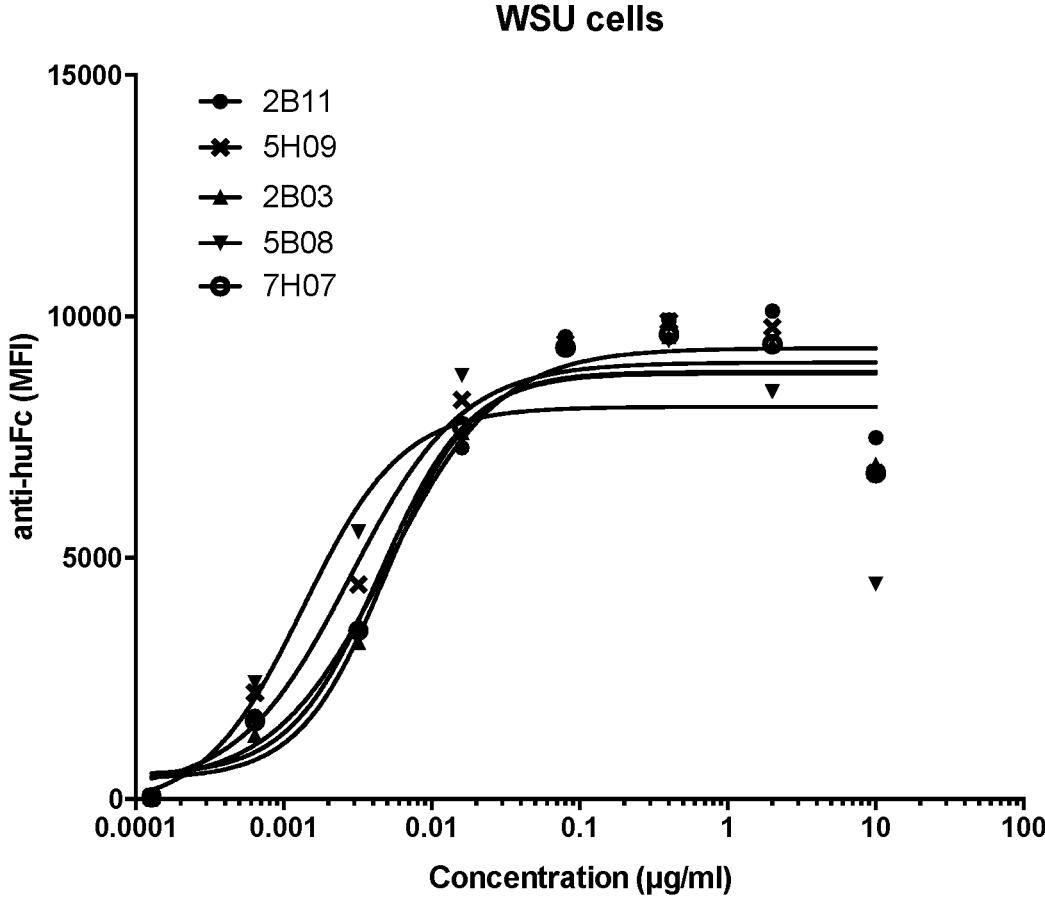
FIG. 5 shows the binding of different CD19 IgG1 clones to human CD19-expressing tumor cells (WSU-DLCL2 cells). Binding was detected with PE-conjugated AffiniPure anti-human IgG F(ab')2-fragment-specific goat F(ab')2 fragment. Shown is the median of fluorescence intensity (MFI) versus the concentration of tested clones.

FIG. 5 shows the binding of the CD19 IgG1 clones to human CD19-expressing WSU-DLCL2 cells. Table 13 shows the $EC_{50}$ values as measured.

TABLE 13

| Binding to human FAP-expressing tumor cells | |
| --- | --- |
| Clone | $EC_{50}$ [pM] CD19⁺ WSU-DLCL2 |
| 2B11 | 34 |
| 5H09 | 20 |
| 2B03 | 41 |
| 5B08 | 14 |
| 7H07 | 34 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

SEQUENCE LISTING

```
Sequence total quantity: 135
SEQ ID NO: 1            moltype = AA  length = 273
FEATURE                 Location/Qualifiers
source                  1..273
                        mol_type = protein
                        organism = Homo sapiens
SEQUENCE: 1
PEEPLVVKVE EGDNAVLQCL KGTSDGPTQQ LTWSRESPLK PFLKLSLGLP GLGIHMRPLA  60
IWLFIFNVSQ QMGGFYLCQP GPPSEKAWQP GWTVNVEGSG ELFRWNVSDL GGLGCGLKNR  120
SSEGPSSPSG KLMSPKLYVW AKDRPEIWEG EPPCLPPRDS LNQSLSQDLT MAPGSTLWLS  180
CGVPPDSVSR GPLSWTHVHP KGPKSLLSLE LKDDRPARDM WVMETGLLLP RATAQDAGKY  240
YCHRGNLTMS FHLEITARPV LWHWLLRTGG WKV                              273

SEQ ID NO: 2            moltype = AA  length = 274
FEATURE                 Location/Qualifiers
source                  1..274
                        mol_type = protein
                        organism = Macaca fascicularis
SEQUENCE: 2
PQEPLVVKVE EGDNAVLQCL EGTSDGPTQQ LVWCRDSPFE PFLNLSLGLP GMGIRMGPLG  60
IWLLIFNVSN QTGGFYLCQP GLPSEKAWQP GWTVSVEGSG ELFRWNVSDL GGLGCGLKNR  120
SSEGPSSPSG KLNSSQLYVW AKDRPEMWEG EPVCGPPRDS LNQSLSQDLT MAPGSTLWLS  180
CGVPPDSVSR GPLSWTHVRP KGPKSSLLSL ELKDDRPDRD MWVVDTGLLL TRATAQDAGK  240
YYCHRGNWTK SFYLEITARP ALWHWLLRIG GWKV                             274

SEQ ID NO: 3            moltype = DNA  length = 681
FEATURE                 Location/Qualifiers
misc_feature            1..681
                        note = Description of Artificial Sequence: Synthetic
                        polynucleotide
misc_feature            1..681
                        note = Nucleotide sequence of Fc hole chain
source                  1..681
                        mol_type = other DNA
                        organism = synthetic construct
SEQUENCE: 3
gacaaaactc acacatgccc accgtgccca gcacctgaag ctgcagggg accgtcagtc   60
ttcctcttcc ccccaaaacc caaggacacc ctcatgatct cccggacccc tgaggtcaca  120
tgcgtggtgg tggacgtgag ccacgaagac cctgaggtca agttcaactg gtacgtggac  180
ggcgtggagg tgcataatgc caagacaaag ccgcgggagg agcagtacaa cagcacgtac  240
cgtgtggtca gcgtcctcac cgtcctgcac caggactggc tgaatggcaa ggagtacaag  300
tgcaaggtct ccaacaaagc cctcggcgcc cccatcgaga aaaccatctc caaagccaaa  360
gggcagcccc gagaaccaca ggtgtgcacc ctgcccccat cccgggatga gctgaccaag  420
aaccaggtca gcctctcgtg cgcagtcaaa ggcttctatc ccagcgacat cgccgtggag  480
tgggagagca atgggcagcc ggagaacaac tacaagacca cgcctcccgt gctggactcc  540
gacggctcct tcttcctcgt gagcaagctc accgtggaca agagcaggtg gcagcagggg  600
```

-continued

```
aacgtcttct catgctccgt gatgcatgag gctctgcaca accgcttcac gcagaagagc   660
ctctccctgt ctccgggtaa a                                              681

SEQ ID NO: 4          moltype = DNA  length = 1602
FEATURE               Location/Qualifiers
misc_feature          1..1602
                      note = Description of Artificial Sequence: Synthetic
                       polynucleotide
misc_feature          1..1602
                      note = Nucleotide sequence of human CD19 antigen Fc knob
                       chain avi tag
source                1..1602
                      mol_type = other DNA
                      organism = synthetic construct
SEQUENCE: 4
cccgaggaac ccctggtcgt gaaggtggaa gagggcgaca atgccgtgct gcagtgcctg    60
aagggcacct ccgatggccc tacccagcag ctgacctggt ccagagagag ccccctgaag   120
cccttcctga agctgtctct gggcctgcct ggctgggcc tccatatgag gcctctgcc     180
atctggctgt tcatcttcaa cgtgcccag cagatgggcg gcttctacct gtgtcagcct    240
ggccccccat ctgagaaggc ttggcagcct ggctggaccg tgaacgtgga aggatccggc    300
gagctgttcc ggtggaacgt gtccgatctg ggcggcctgg gatgcggcct gaagaacaga   360
tctagcgagg gccccagcag ccccagcccg aaactgatga gccccaagct gtacgtgtgg    420
gccaaggaca gacccgagat ctgggagggc gagcctcctt gcctgccccc tagagacagc   480
ctgaaccaga gcctgagcca ggacctgaca atgcccctg gcagcacact gtggctgagc    540
tgtggcgtgc caccccgactc tgtgtctaga ggccctctga gctggaccca cgtgcacct    600
aagggcccta agagcctgct gagcctggaa ctgaaggacg acaggcccgc cagagatatg    660
tgggtcatgg aaaccggcct gctgctgcct agagccacag cccaggatgc cggcaagtac    720
tactgccaca gaggcaacct gaccatgagc ttccacctgg aaatcaccgc cagacccgtg    780
ctgtggcact ggctgctgag aacaggcggc tggaaggtcg acgctagcgg tggtagtccg    840
acacctccga caccggggg tggttctgca gacaaaactc acacatgccc accgtgccca    900
gcacctgaag ccgcaggggg accgtcagtc ttcctcttcc ccccaaaacc caaggacacc    960
ctcatgatct cccggacccc tgaggtcaca tgcgtggtgg tggacgtgag ccacgaagac   1020
cctgaggtca agttcaactg gtacgtggac ggcgtggagg tgcataatgc caagacaaag   1080
ccgcgggagg agcagtacaa cagcacgtac cgtgtggtca gcgtcctcac cgtcctgcac   1140
caggactggc tgaatggcaa ggagtacaag tgcaaggtct ccaacaaagc cctcggagcc   1200
cccatcgaga aaaccatctc caaagccaaa gggcagcccc gagaaccaca ggtgtacacc   1260
ctgccccat gccgggatga gctgaccaag aaccaggtca gcctgtggt cctggtcaaa   1320
ggcttctatc ccagcgacat cgccgtggag tgggagagca atgggcagcc ggagaacaac   1380
tacaagacca cgcctcccgt gctggactcc gacggctcct tcttcctcta cagcaagctc   1440
accgtggaca gagcaggtg gcagcagggg aacgtcttct catgctccgt gatgcatgag   1500
gctctgcaca accactacac gcagaagagc ctctccctgt ctccgggtaa atccggaggc   1560
ctgaacgaca tcttcgaggc ccagaagatt gaatggcacg ag                      1602

SEQ ID NO: 5          moltype = AA  length = 227
FEATURE               Location/Qualifiers
REGION                1..227
                      note = Description of Artificial Sequence: Synthetic
                       polypeptide
REGION                1..227
                      note = Fc hole chain
source                1..227
                      mol_type = protein
                      organism = synthetic construct
SEQUENCE: 5
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALGA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNRFTQKS LSLSPGK                 227

SEQ ID NO: 6          moltype = AA  length = 534
FEATURE               Location/Qualifiers
REGION                1..534
                      note = Description of Artificial Sequence: Synthetic
                       polypeptide
REGION                1..534
                      note = human CD19 antigen Fc knob chain avi tag
source                1..534
                      mol_type = protein
                      organism = synthetic construct
SEQUENCE: 6
PEEPLVVKVE EGDNAVLQCL KGTSDGPTQQ LTWSRESPLK PFLKLSLGLP GLGIHMRPLA    60
IWLFIFNVSQ QMGGFYLCQP GPPSEKAWQP GWTVNVEGSG ELFRWNVSDL GGLGCGLKNR   120
SSEGPSSPSG KLMSPKLYVW AKDRPEIWEG EPPCLPPRDS LNQSLSQDLT MAPGSTLWLS   180
CGVPPDSVSR GPLSWTHVHP KGPKSLLSLE LKDDRPARDM WVMETGLLLP RATAQDAGKY   240
YCHRGNLTMS FHLEITARPV LWHWLLRTGG WKVDASGGSP TPPTPGGGSA DKTHTCPPCP   300
APEAAGGPSV FLFPPKPKDT LMISRTPEVT CVVVDVSHED PEVKFNWYVD GVEVHNAKTK   360
PREEQYNSTY RVVSVLTVLH QDWLNGKEYK CKVSNKALGA PIEKTISKAK GQPREPQVYT   420
LPPCRDELTK NQVSLWCLVK GFYPSDIAVE WESNGQPENN YKTTPPVLDS DGSFFLYSKL   480
TVDKSRWQQG NVFSCSVMHE ALHNHYTQKS LSLSPGKSGG LNDIFEAQKI EWHE          534
```

-continued

```
SEQ ID NO: 7              moltype = DNA  length = 1605
FEATURE                   Location/Qualifiers
misc_feature              1..1605
                          note = Description of Artificial Sequence: Synthetic
                          polynucleotide
misc_feature              1..1605
                          note = Nucleotide sequence of cynomolgus CD19 antigenFc
                          knob chain avi tag
source                    1..1605
                          mol_type = other DNA
                          organism = synthetic construct
SEQUENCE: 7
ccccaggaac ccctggtcgt gaaggtggaa gagggcgaca atgccgtgct ccagtgcctg  60
gaaggcacct ccgatggccc tacacagcag ctcgtgtggt gcagagacag ccccttcgag  120
cccttcctga acctgtctct gggcctgcct ggcatgggca tcagaatggg ccctctgggc  180
atctggctgc tgatcttcaa cgtgtccaac cagaccggcg gcttctacct gtgtcagcct  240
ggcctgccaa gcgagaaggc ttggcagcct ggatggaccg tgtccgtgga aggatctggc  300
gagctgttcc ggtggaacgt gtccgatctg ggcggcctgg gatgcggcct gaagaacaga  360
agcagcgagg ccctagcag ccccagcggc aagctgaata gcagccagct gtacgtgtgg  420
gccaaggaca gacccgagat gtgggagggc gagcctgtgt gtggccccc tagagatagc  480
ctgaaccaga gcctgagcca ggacctgaca atggcccctg gcgccacact gtggctgagc  540
tgtggcgtgc cacccgactc tgtgtccaga ggccctctga gctggacaca cgtgcgccca  600
aagggcccta agagcagcct gctgagcctg aactgaagg acgaccggcc cgaccgggat  660
atgtgggtgg tggatacagg cctgctgctg accagagcca cagcccagga tgccggcaag  720
tactactgcc acagaggcaa ctggaccaag agcttttacc tggaaatcac cgccagaccc  780
gccctgtggc actggctgct gagaatcgga ggctggaagg tcgacgctag cggtggtagt  840
ccgacacctc cgacacccgg gggtggttct gcagacaaaa ctcacacatg cccaccgtgc  900
ccagcacctg aagccgcagg gggaccgtca gtcttcctct tccccccaaa acccaaggac  960
accctcatga tctcccggac ccctgaggtc acatgcgtgg tggtggacgt gagccacgaa  1020
gaccctgagg tcaagttcaa ctggtacgtg gacggcgtgg aggtgcataa tgccaagaca  1080
aagccgcggg aggagcagta caacagcacg taccgtgtgg tcagcgtcct caccgtcctg  1140
caccaggact ggctgaatgg caaggagtac aagtgcaagg tctccaacaa agccctcgga  1200
gcccccatcg agaaaaccat ctccaaagcc aaagggcagc cccgagaacc acaggtgtac  1260
accctgcccc catgccggga tgagctgacc aagaaccagg tcagcctgtg gtgcctggtc  1320
aaaggcttct atcccagcga catcgccgtg gagtgggaga gcaatgggca gccggagaac  1380
aactacaaga ccacgcctcc cgtgctggac tccgacggct ccttcttcct ctacagcaag  1440
ctcaccgtgg acaagagcag gtggcagcag gggaacgtct tctcatgctc cgtgatgcat  1500
gaggctctgc acaaccacta cacgcagaag agcctctccc tgtctccggg taaatccgga  1560
ggcctgaacg acatcttcga ggcccagaag attgaatggc acgag            1605

SEQ ID NO: 8              moltype = AA  length = 535
FEATURE                   Location/Qualifiers
REGION                    1..535
                          note = Description of Artificial Sequence: Synthetic
                          polypeptide
REGION                    1..535
                          note = cynomolgus CD19 antigen Fc knob chain avi tag
source                    1..535
                          mol_type = protein
                          organism = synthetic construct
SEQUENCE: 8
PQEPLVVKVE EGDNAVLQCL EGTSDGPTQQ LVWCRDSPFE PFLNLSLGLP GMGIRMGPLG  60
IWLLIFNVSN QTGGFYLCQP GLPSEKAWQP GWTVSVEGSG ELFRWNVSDL GGLGCGLKNR  120
SSEGPSSPSG KLNSSQLYVW AKDRPEMWEG EPVCGPPRDS LNQSLSQDLT MAPGSTLWLS  180
CGVPPDSVSR GPLSWTHVRP KGPKSSLLSL ELKDDRPDRD MWVVDTGLLL TRATAQDAGK  240
YYCHRGNWTK SFYLEITARP ALWHWLLRIG GWKVDASGGS PTPPTPGGGS ADKTHTCPPC  300
PAPEAAGGPS VFLFPPKPKD TLMISRTPEV TCVVVDVSHE DPEVKFNWYV DGVEVHNAKT  360
KPREEQYNST YRVVSVLTVL HQDWLNGKEY KCKVSNKALG APIEKTISKA KGQPREPQVY  420
TLPPCRDELT KNQVSLWCLV KGFYPSDIAV EWESNGQPEN NYKTTPPVLD SDGSFFLYSK  480
LTVDKSRWQQ GNVFSCSVMH EALHNHYTQK SLSLSPGKSG GLNDIFEAQK IEWHE      535

SEQ ID NO: 9              moltype = DNA  length = 363
FEATURE                   Location/Qualifiers
misc_feature              1..363
                          note = Description of Artificial Sequence: Synthetic
                          polynucleotide
misc_feature              1..363
                          note = Nucleotide sequence CD19 (8B8) VH Parental clone DNA
source                    1..363
                          mol_type = other DNA
                          organism = synthetic construct
SEQUENCE: 9
caagttcaat tggttcaatc tggtgctgaa gtaaaaaaac cgggcgcttc cgttaaagtg  60
agctgcaaag catctggtta caccttcact gactatatca tgcactgggt tcgtcaggcc  120
ccgggccagg gtctggagtg gatgggctac attaacccat acaacgacgg ttccaaatat  180
accgagaaat tccagggccg cgtcacgatg accagcgaca cttctatctc caccgcgtac  240
atggaactgt ctagactgcg ttctgacgac accgctgttt actattgtgc acgcggtact  300
tactactacg gttccgccct ctttgattac tggggccaag gtaccacggt gaccgtaagc  360
```

```
tct                                                                    363

SEQ ID NO: 10            moltype = DNA  length = 336
FEATURE                  Location/Qualifiers
misc_feature             1..336
                         note = Description of Artificial Sequence: Synthetic
                          polynucleotide
misc_feature             1..336
                         note = Nucleotide sequence CD19 (8B8) VL Parental clone DNA
source                   1..336
                         mol_type = other DNA
                         organism = synthetic construct
SEQUENCE: 10
gatattgtta tgactcaaac tccactgtct ctgtccgtga ccccgggtca gccagcgagc  60
atttcttgca aatccagcca atctctggaa aactccaacg gcaacacgta cctgaactgg  120
tatctccaga aaccgggtca gagcccgcag ctgctgatct accgtgtatc taagcgcttc  180
tccggcgttc ctgatcgttt cagcggttct ggatccggca ccgactttac tctgaaaatc  240
agccgtgtgg aagctgaaga cgttggcgtc tactattgtc tgcagttgac ccacgttccg  300
tacaccttcg gtcaaggaac taaactggaa attaaa                            336

SEQ ID NO: 11            moltype = DNA  length = 94
FEATURE                  Location/Qualifiers
misc_feature             1..94
                         note = Description of Artificial Sequence: Synthetic primer
misc_feature             1..94
                         note = 43-45: 40% Y, 6% A/S/T/G/P/D/N/E/Q/V, 49-51: 40% N,
                          6%A/S/T/Y/G/P/D/E/Q/V, 55-57: 25% S/T/Q/E, 61-63: 25%
                          S/T/Q/E
misc_difference          43..45
                         note = modified_base - a, c, g or t
misc_difference          49..51
                         note = modified_base - a, c, g or t
misc_difference          55..57
                         note = modified_base - a, c, g or t
misc_difference          61..63
                         note = modified_base - a, c, g or t
source                   1..94
                         mol_type = other DNA
                         organism = synthetic construct
SEQUENCE: 11
cagctgcggg ctctgacccg gtttctggag ataccagttc agnnncgtnn ngccnnngga  60
nnnttccaga gattggctgg atttgcaaga aatg                              94

SEQ ID NO: 12            moltype = DNA  length = 99
FEATURE                  Location/Qualifiers
misc_feature             1..99
                         note = Description of Artificial Sequence: Synthetic primer
misc_feature             1..99
                         note = 40-42: 30% R, 20% E, 5% A/S/T/Y/G/P/D/N/Q/V. 49-51:
                          30% K, 20% S,5% A/N/T/Y/G/P/D/E/Q/V, 55-57: 40% F, 5%
                          A/S/T/Y/G/P/D/E/Q/V/I/L,58-60: 40% S, 6.6%
                          A/T/Y/G/P/D/E/Q/V, 67-69: 50% P, 50% L
misc_difference          40..42
                         note = modified_base - a, c, g or t
misc_difference          49..51
                         note = modified_base - a, c, g or t
misc_difference          55..60
                         note = modified_base - a, c, g or t
misc_difference          67..69
                         note = modified_base - a, c, g or t
source                   1..99
                         mol_type = other DNA
                         organism = synthetic construct
SEQUENCE: 12
ctccagaaac cgggtcagag cccgcagctg ctgatctacn nngtatctnn ncgcnnnnnn  60
ggcgttnnng atcgtttcag cggttctgga tccggcacc                        99

SEQ ID NO: 13            moltype = DNA  length = 99
FEATURE                  Location/Qualifiers
misc_feature             1..99
                         note = Description of Artificial Sequence: Synthetic primer
misc_feature             1..99
                         note = 40-42: 52% H, 4% G/A/S/P/T/N/Y/D/E/Q/V/I, 46-48: 30%
                          I, 15% Y, 5%G/A/S/T/P/N/H/D/E/Q/V, 49-51: 52% Y, 4%
                          G/A/S/P/T/N/H/D/E/Q/V/I,52-54: 30% D, 15% G, 5%
                          A/S/P/Y/N/H/D/E/Q/V/I, 55-57: 52% T,
                          4%G/A/S/P/Y/N/H/D/E/Q/V/I, 61-63: 52% T, 4%
                          G/A/S/P/Y/N/H/D/E/Q/V/I
misc_difference          40..42
```

```
                          note = modified_base - a, c, g or t
misc_difference           46..57
                          note = modified_base - a, c, g or t
misc_difference           61..63
                          note = modified_base - a, c, g or t
source                    1..99
                          mol_type = other DNA
                          organism = synthetic construct
SEQUENCE: 13
catccactcc agaccctggc ccggggcctg acgaacccan nncatnnnnn nnnnnnngaa   60
nnngtaacca gatgctttgc agctcacttt aacggaagc                          99

SEQ ID NO: 14            moltype = DNA  length = 99
FEATURE                  Location/Qualifiers
misc_feature             1..99
                          note = Description of Artificial Sequence: Synthetic primer
misc_feature             1..99
                          note = 34-36: 45% Y, 5% others, 40-42: 52% N, 4% others,
                          46-48: 40% Y,5% others, 49-51: 30% N, 15% S, 5% others,
                          52-54: 30% D, 15% G,5% others, 55-57: 52% G, 4% others,
                          61-63: 30% K, 15% N, 4%others, 70-72: 30% E, 15% Q, 5%
                          others
misc_difference           34..36
                          note = modified_base - a, c, g or t
misc_difference           40..42
                          note = modified_base - a, c, g or t
misc_difference           46..57
                          note = modified_base - a, c, g or t
misc_difference           61..63
                          note = modified_base - a, c, g or t
misc_difference           70..72
                          note = modified_base - a, c, g or t
source                    1..99
                          mol_type = other DNA
                          organism = synthetic construct
SEQUENCE: 14
caggccccgg gccagggtct ggagtggatg ggcnnnattn nnccannnnn nnnnnnntcc   60
nnntataccn nnaaattcca gggccgcgtc acgatgacc                          99

SEQ ID NO: 15            moltype = DNA  length = 33
FEATURE                  Location/Qualifiers
misc_feature             1..33
                          note = Description of Artificial Sequence: Synthetic primer
misc_feature             1..33
                          note = CD19 H3 reverse constant
source                    1..33
                          mol_type = other DNA
                          organism = synthetic construct
SEQUENCE: 15
cgtcaccggt tcggggaagt agtccttgac cag                                33

SEQ ID NO: 16            moltype = DNA  length = 26
FEATURE                  Location/Qualifiers
misc_feature             1..26
                          note = Description of Artificial Sequence: Synthetic primer
misc_feature             1..26
                          note = LMB3
source                    1..26
                          mol_type = other DNA
                          organism = synthetic construct
SEQUENCE: 16
caggaaacag ctatgaccat gattac                                        26

SEQ ID NO: 17            moltype = DNA  length = 33
FEATURE                  Location/Qualifiers
misc_feature             1..33
                          note = Description of Artificial Sequence: Synthetic primer
misc_feature             1..33
                          note = CD19 L1 forward constant
source                    1..33
                          mol_type = other DNA
                          organism = synthetic construct
SEQUENCE: 17
tggtatctcc agaaaccggg tcagagcccg cag                                33

SEQ ID NO: 18            moltype = DNA  length = 84
FEATURE                  Location/Qualifiers
misc_feature             1..84
                          note = Description of Artificial Sequence: Synthetic primer
```

```
misc_feature             1..84
                         note = 34-36: 52% Y, 4% others, 37-39: 52% P, 4% others,
                          40-42: 42% V,10% L, 4% others, 43-45: 52% H, 4% others,
                          46-48: 42% T, 10% I,4% others, 49-51: 45% L, 11% G, 4%
                          others
misc_difference          34..51
                         note = modified_base - a, c, g or t
source                   1..84
                         mol_type = other DNA
                         organism = synthetic construct
SEQUENCE: 18
tttaatttcc agtttagttc cttgaccgaa ggtnnnnnnn nnnnnnnnnn nctgcagaca  60
atagtagacg ccaacgtctt cagc                                         84

SEQ ID NO: 19            moltype = DNA   length = 35
FEATURE                  Location/Qualifiers
misc_feature             1..35
                         note = Description of Artificial Sequence: Synthetic primer
misc_feature             1..35
                         note = CD19 L3 forward constant
source                   1..35
                         mol_type = other DNA
                         organism = synthetic construct
SEQUENCE: 19
accttcggtc aaggaactaa actggaaatt aaacg                             35

SEQ ID NO: 20            moltype = DNA   length = 107
FEATURE                  Location/Qualifiers
misc_feature             1..107
                         note = Description of Artificial Sequence: Synthetic primer
misc_feature             1..107
                         note = pos. 59-61: 50% L, 3.8% others, 62-64: 50% A, 4.2%
                          others, 65-67:50% S, 4.2% others, 68-70: 50% G, 4.2%
                          others, 71-73: 50% Y, 4.2%others, 74-76: 50% Y, 4.2%
                          others, 77-79: 50% Y, 4.2% others,80-82: 50% T, 4.2%
                          others, 83-85: 50% G, 4.2% others.
misc_difference          54..80
                         note = modified_base - a, c, g or t
source                   1..107
                         mol_type = other DNA
                         organism = synthetic construct
SEQUENCE: 20
ttggtgctag cagagcttac ggtcaccgtg gtaccttggc cccagtaatc aaannnnnnn  60
nnnnnnnnnn nnnnnnnnnn gcgtgcacaa tagtaaacag cggtgtc               107

SEQ ID NO: 21            moltype = DNA   length = 1615
FEATURE                  Location/Qualifiers
misc_feature             1..1615
                         note = Description of Artificial Sequence: Synthetic
                          polynucleotide
misc_feature             1..1615
                         note = SNAP tag humanCD19 ECD- PDGFR DNA
source                   1..1615
                         mol_type = other DNA
                         organism = synthetic construct
SEQUENCE: 21
ggccgccgct agcggcatcg actacaagga cgacgatgac aaggccggca tcgatgccat    60
catggacaaa gactgcgaaa tgaagcgcac caccctggat agccctctgg gcaagctgga   120
actgtctggg tgcgaacagg gcctgcacga gatcaagctg ctgggcaaag gaacatctgc   180
cgccgacgcc gtggaagtgc ctgccccagc cgccgtgctg ggcggaccag agccactgat   240
gcaggccacc gcctggctca acgcctactt tcaccagcct gaggccatcg aggagttccc   300
tgtgccagcc ctgcaccacc cagtgttcca gcaggagagc tttacccgcc aggtgctgtg   360
gaaactgctg aaagtggtga agttcggaga ggtcatcagc taccagcagc tggccgccct   420
ggccggcaat cccgccgcca ccgccgccgt gaaaacgacc ctgacggaa atcccgtgcc   480
cattctgatc ccctgccacc gggtggtgtc tagctctggc gccgtggggg gctacgaggg   540
cgggctcgcc gtgaaagagt ggctgctggc ccacgagggc cacagactgg gcaagctgg   600
gctgggtgat atccccgagg aacccctggt cgtgaaggtg gaagagggcg acaatgccgt   660
gctgcagtgc ctgaagggca cctccgatgg ccctacccag cagctgacct ggtccagaga   720
gagccccctg aagccccttcc tgaagctgtc tctgggcctg cctggcctgg gcatccatat   780
gaggcctctg gccatctggc tgttcatctt caacgtgtcc cagcagatgg gcggcttcta   840
cctgtgtcag cctggccccc catctgagaa ggcttggcag cctggctgga ccgtgaacgt   900
ggaaggatcc ggcgagctgt ccggtggaa cgtgtccgat ctgggcggcc tgggatgcgg   960
cctgaagaac agatctagcg agggccccag cagccccagc ggcaaactga tgagcccaa   1020
gctgtacgtg tgggccaagg acagacccga gatctggggag ggcgagcctc cttgcctgcc   1080
ccctagagac agcctgaacc agagcctgag ccaggacctg acaatggccc ctggcagcac   1140
actgtggctg agctgtggcg tgccaccccga ctctgtgtct agaggccctc tgagctggac   1200
ccacgtgcac cctaagggcc ctaagagcct gctgagcctg gaactgaagg acgacaggc   1260
cgccagagat atgtgggtca tggaaaccgg cctgctgctg cctagagcca cagcccagga   1320
tgccggcaag tactactgcc acagaggcaa cctgaccatg agcttccacc tggaaatcac   1380
```

-continued

```
cgccagaccc gtgctgtggc actggctgct gagaacaggc ggctggaagg tcgacgaaca  1440
aaaactcatc tcagaagagg atctgaatgc tgtgggccag gacacgcagg aggtcatcgt  1500
ggtgccacac tccttgccct ttaaggtggt ggtgatctca gccatcctgg ccctggtggt  1560
gctcaccatc atctccctta tcatcctcat catgctttgg cagaagaagc cacgt         1615

SEQ ID NO: 22            moltype = DNA  length = 1620
FEATURE                  Location/Qualifiers
misc_feature            1..1620
                        note = Description of Artificial Sequence: Synthetic
                         polynucleotide
misc_feature            1..1620
                        note = SNAP tag cynomolgusCD19 ECD- PDGFR DNA
source                  1..1620
                        mol_type = other DNA
                        organism = synthetic construct SEQUENCE: 22
ccggccgccg ctagcggcat cgactacaag gacgacgatg acaaggccgg catcgatgcc  60
atcatggaca aagactgcga aatgaagcgc accaccctct atagccctct gggcaagctg  120
gaactgtctg ggtgcgaaca gggcctgcac gagatcaagc tgctgggcaa aggaacatct  180
gccgccgacg ccgtggaagt gcctgcccca gccgccgtgc tgggcggacc agagccactg  240
atgcaggcca ccgcctggct caacgcctac tttcaccagc ctgaggccat cgaggagttc  300
cctgtgccag ccctgcacca cccagtgttc cagcaggaga gctttacccg ccaggtgctg  360
tggaaactgc tgaaagtggt gaagttcgga gaggtcatca gctaccagca gctggccgcc  420
ctggccggca tcccgccgc caccgccgcc gtgaaaaccg ccctgagcgg aaatcccgtg  480
cccattctga tcccctgcca ccgggtggtg tctagctctg gcgccgtggg gggctacgag  540
ggcgggctcg ccgtgaaaga gtggctgctg ccccacgagg gccacagact gggcaagcct  600
gggctgggtg atatccccca ggaaccctg tcgtgaagg tggaagaggg cgacaatgcc  660
gtgctccagt gtctcgaggg cacctccgat ggcctacac agcagctcgt gtggtgcaga  720
gacagcccct tcgagcctt cctgaacctg tctctgggcc tgcctggcat gggcatcaga  780
atggccctc tgggcatctg gctgctgatc ttcaacgtgt ccaaccagac cggcggcttc  840
tacctgtgtc agcctggcct gccaagcgag aaggcttggc agcctggatg gaccgtgtcc  900
gtggaaggat ctggcgagct gttccggtgg aacgtgtccg atctgggcgg cctgggatgc  960
ggcctgaaga cagaagcag cgagggccct agcagcccca gcggcaagct gaatagcagc  1020
cagctgtacg tgtgggccaa ggacagaccc gagatgtggg agggcgagcc tgtgtgtggc  1080
cccctagag atagcctgaa ccagagcctg agccaggacc tgacaatggc ccctggcagc  1140
acactgtggc tgagctgtgg cgtgccaccc gactctgtgt ccagaggccc tctgagctgg  1200
acacacgtgc ggcctaaggg ccctaagagc agcctgctga gcctggaact gaaggacgac  1260
cggcccgacc gggatatgtg ggtggtggat acaggcctgc tgctgaccag agccacagcc  1320
caggatgccg gcaagtacta ctgccacaga ggcaactgga ccaagagctt ttacctggaa  1380
atcaccgcca gacccgccct gtggcactgg ctgctgagaa tcggaggctg gaaggtcgac  1440
gagcagaagc tgatctccga agaggacctg aacgccgtgg gccaggatac ccaggaagtg  1500
atcgtggtgc cccacagcct gcccttcaag gtggtcgtga tcagcgccat tctggccctg  1560
gtggtgctga ccatcatcag cctgatcatc ctgattatgc tgtggcagaa aaagccccgc  1620

SEQ ID NO: 23            moltype = AA  length = 539
FEATURE                  Location/Qualifiers
REGION                  1..539
                        note = Description of Artificial Sequence: Synthetic
                         polypeptide
REGION                  1..539
                        note = SNAP tag humanCD19 ECD- PDGFR
source                  1..539
                        mol_type = protein
                        organism = synthetic construct SEQUENCE: 23
PAAASGIDYK DDDDKAGIDA IMDKDCEMKR TTLDSPLGKL ELSGCEQGLH EIKLLGKGTS  60
AADAVEVPAP AAVLGGPEPL MQATAWLNAY FHQPEAIEEF PVPALHHPVF QQESFTRQVL  120
WKLLKVVKFG EVISYQQLAA LAGNPAATAA VKTALSGNPV PILIPCHRVV SSSGAVGGYE  180
GGLAVKEWLL AHEGHRLGKP GLGDIPEEPL VVKVEEGDNA VLQCLKGTSD GPTQQLTWSR  240
ESPLKPFLKL SLGLPGLGIH MRPLAIWLFI FNVSQQMGGF YLCQPGPPSE KAWQPGWTVN  300
VEGSGELFRW NVSDLGGLGC GLKNRSSEGP SSPSGKLMSP KLYVWAKDRP EIWEGEPPCL  360
PPRDSLNQSL SQDLTMAPGS TLWLSCGVPP DSVSRGPLSW THVHPKGPKS LLSLELKDDR  420
PARDMWVMET GLLLPRATAQ DAGKYYCHRG NLTMSFHLEI TARPVLWHWL LRTGGWKVDE  480
QKLISEEDLN AVGQDTQEVI VVPHSLPFKV VVISAILALV VLTIISLIIL IMLWQKKPR   539

SEQ ID NO: 24            moltype = AA  length = 540
FEATURE                  Location/Qualifiers
REGION                  1..540
                        note = Description of Artificial Sequence: Synthetic
                         polypeptide
REGION                  1..540
                        note = SNAP tag cynomolgusCD19 ECD- PDGFR
source                  1..540
                        mol_type = protein
                        organism = synthetic construct SEQUENCE: 24
PAAASGIDYK DDDDKAGIDA IMDKDCEMKR TTLDSPLGKL ELSGCEQGLH EIKLLGKGTS  60
AADAVEVPAP AAVLGGPEPL MQATAWLNAY FHQPEAIEEF PVPALHHPVF QQESFTRQVL  120
WKLLKVVKFG EVISYQQLAA LAGNPAATAA VKTALSGNPV PILIPCHRVV SSSGAVGGYE  180
```

-continued

```
GGLAVKEWLL AHEGHRLGKP GLGDIPQEPL VVKVEEGDNA VLQCLEGTSD GPTQQLVWCR  240
DSPFEPFLNL SLGLPGMGIR MGPLGIWLLI FNVSNQTGGF YLCQPGLPSE KAWQPGWTVS  300
VEGSGELFRW NVSDLGGLGC GLKNRSSEGP SSPSGKLNSS QLYVWAKDRP EMWEGEPVCG  360
PPRDSLNQSL SQDLTMAPGS TLWLSCGVPP DSVSRGPLSW THVRPKGPKS SLLSLELKDD  420
RPDRDMWVVD TGLLLTRATA QDAGKYYCHR GNWTKSFYLE ITARPALWHW LLRIGGWKVD  480
EQKLISEEDL NAVGQDTQEV IVVPHSLPFK VVVISAILAL VVLTIISLII LIMLWQKKPR  540

SEQ ID NO: 25              moltype = AA   length = 16
FEATURE                    Location/Qualifiers
REGION                     1..16
                           note = Description of Artificial Sequence: Synthetic peptide
REGION                     1..16
                           note = CD19 (8B8-5H09) CDR-L1
source                     1..16
                           mol_type = protein
                           organism = synthetic construct
SEQUENCE: 25
KSSQSLESST GNTYLN                                                  16

SEQ ID NO: 26              moltype = AA   length = 7
FEATURE                    Location/Qualifiers
REGION                     1..7
                           note = Description of Artificial Sequence: Synthetic peptide
REGION                     1..7
                           note = CD19(8B8-5H09) CDR-L2
source                     1..7
                           mol_type = protein
                           organism = synthetic construct
SEQUENCE: 26
RVSKRFS                                                            7

SEQ ID NO: 27              moltype = AA   length = 9
FEATURE                    Location/Qualifiers
REGION                     1..9
                           note = Description of Artificial Sequence: Synthetic peptide
REGION                     1..9
                           note = CD19(8B8-5H09) CDR-L3
source                     1..9
                           mol_type = protein
                           organism = synthetic construct
SEQUENCE: 27
LQLIDYPVT                                                          9

SEQ ID NO: 28              moltype = AA   length = 5
FEATURE                    Location/Qualifiers
REGION                     1..5
                           note = Description of Artificial Sequence: Synthetic peptide
REGION                     1..5
                           note = CD19(8B8-5H09) CDR-H1
source                     1..5
                           mol_type = protein
                           organism = synthetic construct
SEQUENCE: 28
DYIMH                                                              5

SEQ ID NO: 29              moltype = AA   length = 17
FEATURE                    Location/Qualifiers
REGION                     1..17
                           note = Description of Artificial Sequence: Synthetic peptide
REGION                     1..17
                           note = CD19(8B8-5H09) CDR-H2
source                     1..17
                           mol_type = protein
                           organism = synthetic construct
SEQUENCE: 29
YINPYNDGSK YTEKFQG                                                 17

SEQ ID NO: 30              moltype = AA   length = 12
FEATURE                    Location/Qualifiers
REGION                     1..12
                           note = Description of Artificial Sequence: Synthetic peptide
REGION                     1..12
                           note = CDR(8B8-5H09) CDR-H3
source                     1..12
                           mol_type = protein
                           organism = synthetic construct
SEQUENCE: 30
GTYYYGSALF DY                                                      12
```

-continued

```
SEQ ID NO: 31         moltype = AA   length = 16
FEATURE               Location/Qualifiers
REGION                1..16
                      note = Description of Artificial Sequence: Synthetic peptide
REGION                1..16
                      note = CD19(8B8-7H07) CDR-L1
source                1..16
                      mol_type = protein
                      organism = synthetic construct
SEQUENCE: 31
KSSQSLETST GNTYLN                                                      16

SEQ ID NO: 32         moltype = AA   length = 7
FEATURE               Location/Qualifiers
REGION                1..7
                      note = Description of Artificial Sequence: Synthetic peptide
REGION                1..7
                      note = CD19 (8B8-7H07) CDR-L2
source                1..7
                      mol_type = protein
                      organism = synthetic construct
SEQUENCE: 32
RVSKRFS                                                                7

SEQ ID NO: 33         moltype = AA   length = 9
FEATURE               Location/Qualifiers
REGION                1..9
                      note = Description of Artificial Sequence: Synthetic peptide
REGION                1..9
                      note = CD19 (8B8-7H07) CDR-L3
source                1..9
                      mol_type = protein
                      organism = synthetic construct
SEQUENCE: 33
LQATHIPYT                                                              9

SEQ ID NO: 34         moltype = AA   length = 5
FEATURE               Location/Qualifiers
REGION                1..5
                      note = Description of Artificial Sequence: Synthetic peptide
REGION                1..5
                      note = CD19 (8B8-7H07) CDR-H1
source                1..5
                      mol_type = protein
                      organism = synthetic construct
SEQUENCE: 34
DYIMH                                                                  5

SEQ ID NO: 35         moltype = AA   length = 17
FEATURE               Location/Qualifiers
REGION                1..17
                      note = Description of Artificial Sequence: Synthetic peptide
REGION                1..17
                      note = CD19 (8B8-7H07) CDR-H2
source                1..17
                      mol_type = protein
                      organism = synthetic construct
SEQUENCE: 35
YINPYNDGSK YTEKFQG                                                     17

SEQ ID NO: 36         moltype = AA   length = 12
FEATURE               Location/Qualifiers
REGION                1..12
                      note = Description of Artificial Sequence: Synthetic peptide
REGION                1..12
                      note = CD19 (8B8-7H07) CDR-H3
source                1..12
                      mol_type = protein
                      organism = synthetic construct
SEQUENCE: 36
GTYYYGSELF DY                                                          12

SEQ ID NO: 37         moltype = AA   length = 16
FEATURE               Location/Qualifiers
REGION                1..16
                      note = Description of Artificial Sequence: Synthetic peptide
REGION                1..16
                      note = CD19 (8B8-2B03) CDR-L1
source                1..16
```

-continued

```
                         mol_type = protein
                         organism = synthetic construct
SEQUENCE: 37
KSSQSLETST GNTYLN                                                      16

SEQ ID NO: 38           moltype = AA  length = 7
FEATURE                 Location/Qualifiers
REGION                  1..7
                        note = Description of Artificial Sequence: Synthetic peptide
REGION                  1..7
                        note = CD19 (8B8-2B03) CDR-L2
source                  1..7
                        mol_type = protein
                        organism = synthetic construct
SEQUENCE: 38
RVSKRFS                                                                7

SEQ ID NO: 39           moltype = AA  length = 9
FEATURE                 Location/Qualifiers
REGION                  1..9
                        note = Description of Artificial Sequence: Synthetic peptide
REGION                  1..9
                        note = CD19 (8B8-2B03) CDR-L3
source                  1..9
                        mol_type = protein
                        organism = synthetic construct
SEQUENCE: 39
LQLTHVPYT                                                              9

SEQ ID NO: 40           moltype = AA  length = 5
FEATURE                 Location/Qualifiers
REGION                  1..5
                        note = Description of Artificial Sequence: Synthetic peptide
REGION                  1..5
                        note = CD19 (8B8-2B03) CDR-H1
source                  1..5
                        mol_type = protein
                        organism = synthetic construct
SEQUENCE: 40
DYITH                                                                  5

SEQ ID NO: 41           moltype = AA  length = 17
FEATURE                 Location/Qualifiers
REGION                  1..17
                        note = Description of Artificial Sequence: Synthetic peptide
REGION                  1..17
                        note = CD19 (8B8-2B03) CDR-H2
source                  1..17
                        mol_type = protein
                        organism = synthetic construct
SEQUENCE: 41
YINPYNDGSK YTEKFQG                                                     17

SEQ ID NO: 42           moltype = AA  length = 12
FEATURE                 Location/Qualifiers
REGION                  1..12
                        note = Description of Artificial Sequence: Synthetic peptide
REGION                  1..12
                        note = CD19 (8B8-2B03) CDR-H3
source                  1..12
                        mol_type = protein
                        organism = synthetic construct
SEQUENCE: 42
GTYYYGPDLF DY                                                          12

SEQ ID NO: 43           moltype = AA  length = 16
FEATURE                 Location/Qualifiers
REGION                  1..16
                        note = Description of Artificial Sequence: Synthetic peptide
REGION                  1..16
                        note = CD19 (8B8-2B11) CDR-L1
source                  1..16
                        mol_type = protein
                        organism = synthetic construct
SEQUENCE: 43
KSSQSLETST GTTYLN                                                      16

SEQ ID NO: 44           moltype = AA  length = 7
FEATURE                 Location/Qualifiers
```

```
REGION                1..7
                      note = Description of Artificial Sequence: Synthetic peptide
REGION                1..7
                      note = CD19 (8B8-2B11) CDR-L2
source                1..7
                      mol_type = protein
                      organism = synthetic construct SEQUENCE: 44
RVSKRFS                                                                  7

SEQ ID NO: 45         moltype = AA  length = 9
FEATURE               Location/Qualifiers
REGION                1..9
                      note = Description of Artificial Sequence: Synthetic peptide
REGION                1..9
                      note = CD19 (8B8-2B11) CDR-L3
source                1..9
                      mol_type = protein
                      organism = synthetic construct SEQUENCE: 45
LQLLEDPYT                                                                9

SEQ ID NO: 46         moltype = AA  length = 5
FEATURE               Location/Qualifiers
REGION                1..5
                      note = Description of Artificial Sequence: Synthetic peptide
REGION                1..5
                      note = CD19 (8B8-2B11) CDR-H1
source                1..5
                      mol_type = protein
                      organism = synthetic construct SEQUENCE: 46
DYIMH                                                                    5

SEQ ID NO: 47         moltype = AA  length = 17
FEATURE               Location/Qualifiers
REGION                1..17
                      note = Description of Artificial Sequence: Synthetic peptide
REGION                1..17
                      note = CD19 (8B8-2B11) CDR-H2
source                1..17
                      mol_type = protein
                      organism = synthetic construct SEQUENCE: 47
YINPYNDGSK YTEKFQG                                                       17

SEQ ID NO: 48         moltype = AA  length = 12
FEATURE               Location/Qualifiers
REGION                1..12
                      note = Description of Artificial Sequence: Synthetic peptide
REGION                1..12
                      note = CD19 (8B8-2B11) CDR-H3
source                1..12
                      mol_type = protein
                      organism = synthetic construct SEQUENCE: 48
GTYYYGPQLF DY                                                            12

SEQ ID NO: 49         moltype = AA  length = 16
FEATURE               Location/Qualifiers
REGION                1..16
                      note = Description of Artificial Sequence: Synthetic peptide
REGION                1..16
                      note = CD19 (8B8-5A07) CDR-L1
source                1..16
                      mol_type = protein
                      organism = synthetic construct SEQUENCE: 49
KSSQSLETST GNTYLN                                                        16

SEQ ID NO: 50         moltype = AA  length = 7
FEATURE               Location/Qualifiers
REGION                1..7
                      note = Description of Artificial Sequence: Synthetic peptide
REGION                1..7
                      note = CD19 (8B8-5A07) CDR-L2
source                1..7
                      mol_type = protein
                      organism = synthetic construct
```

-continued

```
SEQUENCE: 50
RVSKRFS                                                                    7

SEQ ID NO: 51          moltype = AA  length = 9
FEATURE                Location/Qualifiers
REGION                 1..9
                       note = Description of Artificial Sequence: Synthetic peptide
REGION                 1..9
                       note = CD19 (8B8-5A07) CDR-L3
source                 1..9
                       mol_type = protein
                       organism = synthetic construct
SEQUENCE: 51
LQPGHYPGT                                                                  9

SEQ ID NO: 52          moltype = AA  length = 5
FEATURE                Location/Qualifiers
REGION                 1..5
                       note = Description of Artificial Sequence: Synthetic peptide
REGION                 1..5
                       note = CD19 (8B8-5A07) CDR-H1
source                 1..5
                       mol_type = protein
                       organism = synthetic construct
SEQUENCE: 52
DYIMH                                                                      5

SEQ ID NO: 53          moltype = AA  length = 17
FEATURE                Location/Qualifiers
REGION                 1..17
                       note = Description of Artificial Sequence: Synthetic peptide
REGION                 1..17
                       note = CD19 (8B8-5A07) CDR-H2
source                 1..17
                       mol_type = protein
                       organism = synthetic construct
SEQUENCE: 53
YINPYNDGSK YTEKFQG                                                         17

SEQ ID NO: 54          moltype = AA  length = 12
FEATURE                Location/Qualifiers
REGION                 1..12
                       note = Description of Artificial Sequence: Synthetic peptide
REGION                 1..12
                       note = CD19 (8B8-5A07) CDR-H3
source                 1..12
                       mol_type = protein
                       organism = synthetic construct
SEQUENCE: 54
GTYYYGSALF DY                                                              12

SEQ ID NO: 55          moltype = AA  length = 16
FEATURE                Location/Qualifiers
REGION                 1..16
                       note = Description of Artificial Sequence: Synthetic peptide
REGION                 1..16
                       note = CD19 (8B8-5B08) CDR-L1
source                 1..16
                       mol_type = protein
                       organism = synthetic construct
SEQUENCE: 55
KSSQSLETST GNTYLN                                                          16

SEQ ID NO: 56          moltype = AA  length = 7
FEATURE                Location/Qualifiers
REGION                 1..7
                       note = Description of Artificial Sequence: Synthetic peptide
REGION                 1..7
                       note = CD19 (8B8-5B08) CDR-L2
source                 1..7
                       mol_type = protein
                       organism = synthetic construct
SEQUENCE: 56
RVSKRFS                                                                    7

SEQ ID NO: 57          moltype = AA  length = 9
FEATURE                Location/Qualifiers
REGION                 1..9
                       note = Description of Artificial Sequence: Synthetic peptide
```

-continued

```
REGION                      1..9
                            note = CD19 (8B8-5B08) CDR-L3
source                      1..9
                            mol_type = protein
                            organism = synthetic construct
SEQUENCE: 57
LQLDSYPNT                                                               9

SEQ ID NO: 58               moltype = AA  length = 5
FEATURE                     Location/Qualifiers
REGION                      1..5
                            note = Description of Artificial Sequence: Synthetic peptide
REGION                      1..5
                            note = CD19 (8B8-5B08) CDR-H1
source                      1..5
                            mol_type = protein
                            organism = synthetic construct
SEQUENCE: 58
DYIMH                                                                   5

SEQ ID NO: 59               moltype = AA  length = 17
FEATURE                     Location/Qualifiers
REGION                      1..17
                            note = Description of Artificial Sequence: Synthetic peptide
REGION                      1..17
                            note = CD19 (8B8-5B08) CDR-H2
source                      1..17
                            mol_type = protein
                            organism = synthetic construct
SEQUENCE: 59
YINPYNDGSK YTEKFQG                                                     17

SEQ ID NO: 60               moltype = AA  length = 12
FEATURE                     Location/Qualifiers
REGION                      1..12
                            note = Description of Artificial Sequence: Synthetic peptide
REGION                      1..12
                            note = CD19 (8B8-5B08) CDR-H3
source                      1..12
                            mol_type = protein
                            organism = synthetic construct
SEQUENCE: 60
GTYYYGPQLF DY                                                          12

SEQ ID NO: 61               moltype = AA  length = 16
FEATURE                     Location/Qualifiers
REGION                      1..16
                            note = Description of Artificial Sequence: Synthetic peptide
REGION                      1..16
                            note = CD19 (8B8-5D08) CDR-L1
source                      1..16
                            mol_type = protein
                            organism = synthetic construct
SEQUENCE: 61
KSSQSLETST GNTYLN                                                      16

SEQ ID NO: 62               moltype = AA  length = 7
FEATURE                     Location/Qualifiers
REGION                      1..7
                            note = Description of Artificial Sequence: Synthetic peptide
REGION                      1..7
                            note = CD19 (8B8-5D08) CDR-L2
source                      1..7
                            mol_type = protein
                            organism = synthetic construct
SEQUENCE: 62
RVSKRFS                                                                 7

SEQ ID NO: 63               moltype = AA  length = 9
FEATURE                     Location/Qualifiers
REGION                      1..9
                            note = Description of Artificial Sequence: Synthetic peptide
REGION                      1..9
                            note = CD19 (8B8-5D08) CDR-L3
source                      1..9
                            mol_type = protein
                            organism = synthetic construct
SEQUENCE: 63
LQLTHEPYT                                                               9
```

```
SEQ ID NO: 64          moltype = AA   length = 5
FEATURE                Location/Qualifiers
REGION                 1..5
                       note = Description of Artificial Sequence: Synthetic peptide
REGION                 1..5
                       note = CD19 (8B8-5D08) CDR-H1
source                 1..5
                       mol_type = protein
                       organism = synthetic construct
SEQUENCE: 64
DYIMH                                                              5

SEQ ID NO: 65          moltype = AA   length = 17
FEATURE                Location/Qualifiers
REGION                 1..17
                       note = Description of Artificial Sequence: Synthetic peptide
REGION                 1..17
                       note = CD19 (8B8-5D08) CDR-H2
source                 1..17
                       mol_type = protein
                       organism = synthetic construct
SEQUENCE: 65
YINPYNDGSK YTEKFQG                                                 17

SEQ ID NO: 66          moltype = AA   length = 12
FEATURE                Location/Qualifiers
REGION                 1..12
                       note = Description of Artificial Sequence: Synthetic peptide
REGION                 1..12
                       note = CD19 (8B8-5D08) CDR-H3
source                 1..12
                       mol_type = protein
                       organism = synthetic construct
SEQUENCE: 66
GTYYYGSELF DY                                                      12

SEQ ID NO: 67          moltype = DNA   length = 657
FEATURE                Location/Qualifiers
misc_feature           1..657
                       note = Description of Artificial Sequence: Synthetic
                        polynucleotide
misc_feature           1..657
                       note = CD19 (8B8) parental light chain DNA
source                 1..657
                       mol_type = other DNA
                       organism = synthetic construct
SEQUENCE: 67
gatgctgtga tgacccaaac tccactctcc ctgcctgtca gtcttggaga tcaagcctcc   60
atctcttgca ggtctagtca gagccttgaa aacagtaatg gaaacaccta tttgaactgg   120
tacctccaga aaccaggcca gtctccacaa ctcctgatct acagggtttc caaacgattt   180
tctgggGtcc tagacaggtt cagtggtagt ggatcaggga cagatttcac actgaaaatc   240
agcagagtgg aggctgagga tttgggagtt tatttctgcc tacaacttac acatgtcccg   300
tacacgttcg gagggGGGac caagctggaa ataaaacgta cggtggctgc accatctgtc   360
ttcatcttcc cgccatctga tgagcagttg aaatctggaa ctgcctctgt tgtgtgcctg   420
ctgaataact ctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt       657

SEQ ID NO: 68          moltype = DNA   length = 1353
FEATURE                Location/Qualifiers
misc_feature           1..1353
                       note = Description of Artificial Sequence: Synthetic
                        polynucleotide
misc_feature           1..1353
                       note = CD19 (8B8)parental heavy chain DNA
source                 1..1353
                       mol_type = other DNA
                       organism = synthetic construct
SEQUENCE: 68
gaggtccagc tgcagcagtc tggacctgag ctggtaaagc ctggggcttc agtgaagatg   60
gcctgcaagg cttctggata cacattcact gactatatta tgcactgggt gaagcagaag   120
actgggcagg gccttgagtg gattggatat attaatcctt acaatgatgg ttctaagtac   180
actgagaagt tcaacggcaa ggccacactg acttcagaca aatcttccat cacagcctac   240
atggagctca gcagcctgac ctctgaggac tctgcggtct attactgtgc aagagggacc   300
tattattatg gtagcgccct ctttgactac tggggccaag gcaccactct cacagtctcc   360
tcggctagca ccaagggccc atcggtcttc cccctggcac cctcctccaa gagcacctct   420
gggggcacag cggccctggg ctgcctggtc aaggactact ccccgaacc ggtgacggtg   480
```

-continued

```
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctg tgacaaaac tcacacatgc ccaccgtgcc cagcacctga gctgcaggg  720
ggaccgtcag tcttcctctt cccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcggcg cccccatcga gaaaaccatc 1020
tccaaagcca aagggcagcc ccgagaacca caggtgtaca ccctgccccc atcccgggat 1080
gagctgacca gaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tacagcaagc tcaccgtgga caagagcagg 1260
tggcagcagg ggaacgtctt ctcatgctcc gtgatgcatg aggctctgca caaccactac 1320
acgcagaaga gcctctccct gtctccgggt aaa                               1353
```

SEQ ID NO: 69         moltype = AA  length = 219
FEATURE               Location/Qualifiers
REGION                1..219
                      note = Description of Artificial Sequence: Synthetic
                       polypeptide
REGION                1..219
                      note = CD19 (8B8) parental light chain
source                1..219
                      mol_type = protein
                      organism = synthetic construct
SEQUENCE: 69
DIVMTQTPLS LSVTPGQPAS ISCKSSQSLE NSNGNTYLNW YLQKPGQSPQ LLIYRVSKRF  60
SGVPDRFSGS GSGTDFTLKI SRVEAEDVGV YYCLQLTHVP YTFGQGTKLE IKRTVAAPSV 120
FIFPPSDEQL KSGTASVVCL LNNFYPREAK VQWKVDNALQ SGNSQESVTE QDSKDSTYSL 180
SSTLTLSKAD YEKHKVYACE VTHQGLSSPV TKSFNRGEC                         219

SEQ ID NO: 70         moltype = AA  length = 451
FEATURE               Location/Qualifiers
REGION                1..451
                      note = Description of Artificial Sequence: Synthetic
                       polypeptide
REGION                1..451
                      note = CD19 (8B8)parental heavy chain
source                1..451
                      mol_type = protein
                      organism = synthetic construct
SEQUENCE: 70
QVQLVQSGAE VKKPGASVKV SCKASGYTFT DYIMHWVRQA PGQGLEWMGY INPYNDGSKY  60
TEKFQGRVTM TSDTSISTAY MELSRLRSDD TAVYYCARGT YYYGSALFDY WGQGTTVTVS 120
SASTKGPSVF PLAPSSKSTS GGTAALGCLV KDYFPEPVTV SWNSGALTSG VHTFPAVLQS 180
SGLYSLSSVV TVPSSSLGTQ TYICNVNHKP SNTKVDKKVE PKSCDKTHTC PPCPAPEAAG 240
GPSVFLFPPK PKDTLMISRT PEVTCVVVDV SHEDPEVKFN WYVDGVEVHN AKTKPREEQY 300
NSTYRVVSVL TVLHQDWLNG KEYKCKVSNK ALGAPIEKTI SKAKGQPREP QVYTLPPSRD 360
ELTKNQVSLT CLVKGFYPSD IAVEWESNGQ PENNYKTTPP VLDSDGSFFL YSKLTVDKSR 420
WQQGNVFSCS VMHEALHNHY TQKSLSLSPG K                                 451

SEQ ID NO: 71         moltype = DNA  length = 657
FEATURE               Location/Qualifiers
misc_feature          1..657
                      note = Description of Artificial Sequence: Synthetic
                       polynucleotide
misc_feature          1..657
                      note = CD19 (8B8-2B11) light chain DNA
source                1..657
                      mol_type = other DNA
                      organism = synthetic construct
SEQUENCE: 71
gatattgtca tgactcaaac tccactgtct ctgtccgtga ccccgggtca gccagcgagc  60
atttcttgca aatccagcca atctctggaa acctccaccg gcaccacgta cctgaactgg 120
tatctccaga aaccgggtca gagcccgcag ctgctgatct accgtgtatc taagcgcttc 180
tccggcgttc ctgatcgttt cagcggttct ggatccggca ccgactttac tctgaaaatc 240
agccgtgtgg aagctgaaga cgttggcgtc tactattgtc tgcagctgct ggaagatcca 300
tacaccttcg gtcaaggaac gaaactggaa attaaacgta cggtggctgc accatctgtc 360
ttcatcttcc cgccatctga tgagcagttg aaatctggaa ctgcctctgt tgtgtgcctg 420
ctgaataact ctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt    657

SEQ ID NO: 72         moltype = DNA  length = 1353
FEATURE               Location/Qualifiers
misc_feature          1..1353
                      note = Description of Artificial Sequence: Synthetic
```

-continued

```
                         polynucleotide
misc_feature             1..1353
                         note = CD19 (8B8-2B11)heavy chain DNA
source                   1..1353
                         mol_type = other DNA
                         organism = synthetic construct
SEQUENCE: 72
caggtgcaat tggttcaatc tggtgctgaa gtaaaaaaac cgggcgcttc cgttaaagtg   60
agctgcaaag catctggtta caccttcact gactatatca tgcactgggt tcgtcaggcc  120
ccgggccagg gtctggagtg gatgggctac attaacccat acaacgacgg ttccaaatat  180
accgagaaat tccagggccg cgtcacgatg accagcgaca cttctatctc caccgcgtac  240
atggaactgt ctagactgcg ttctgacgac accgctgttt actattgtgc acgcggtacc  300
tactactacg gtccacagct gtttgattac tggggccaag gtaccacggt gaccgtaagc  360
tctgctagca ccaagggccc atcggtcttc cccctgccac cctcctccaa gagcacctct  420
gggggcacag cggccctggg ctgcctggtc aaggactact ccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga gctgcaggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcggcg ccccccatcga gaaaaccatc 1020
tccaaagcca aagggcagcc ccgagaacca caggtgtaca ccctgcccc atcccgggat 1080
gagctgacca agaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tacagcaagc tcaccgtgga caagagcagg 1260
tggcagcagg ggaacgtctt ctcatgctcc gtgatgcatg aggctctgca caaccactac 1320
acgcagaaga gcctctccct gtctccgggt aaa                               1353

SEQ ID NO: 73          moltype = AA  length = 219
FEATURE                Location/Qualifiers
REGION                 1..219
                       note = Description of Artificial Sequence: Synthetic
                        polypeptide
REGION                 1..219
                       note = CD19 (8B8-2B11)light chain
source                 1..219
                       mol_type = protein
                       organism = synthetic construct
SEQUENCE: 73
DIVMTQTPLS LSVTPGQPAS ISCKSSQSLE TSTGTTYLNW YLQKPGQSPQ LLIYRVSKRF   60
SGVPDRFSGS GSGTDFTLKI SRVEAEDVGV YYCLQLLEDP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 74          moltype = AA  length = 451
FEATURE                Location/Qualifiers
REGION                 1..451
                       note = Description of Artificial Sequence: Synthetic
                        polypeptide
REGION                 1..451
                       note = CD19 (8B8-2B11) heavy chain
source                 1..451
                       mol_type = protein
                       organism = synthetic construct
SEQUENCE: 74
QVQLVQSGAE VKKPGASVKV SCKASGYTFT DYIMHWVRQA PGQGLEWMGY INPYNDGSKY   60
TEKFQGRVTM TSDTSISTAY MELSRLRSDD TAVYYCARGT YYYGPQLFDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 75          moltype = DNA  length = 657
FEATURE                Location/Qualifiers
misc_feature           1..657
                       note = Description of Artificial Sequence: Synthetic
                        polynucleotide
misc_feature           1..657
                       note = CD19 (8B8-7H07)light chain DNA
source                 1..657
                       mol_type = other DNA
                       organism = synthetic construct
SEQUENCE: 75
gatattgtta tgactcaaac tccactgtct ctgtccgtga ccccgggtca gccagcgagc   60
```

-continued

```
atttcttgca aatccagcca atctctggaa acctccaccg gcaacacgta cctgaactgg   120
tatctccaga aaccgggtca gagcccgcag ctgctgatct accgtgtatc taagcgcttc   180
tccggcgttc ctgatcgttt cagcggttct ggatccggca ccgactttac tctgaaaatc   240
agccgtgtgg aagctgaaga cgttggcgtc tactattgtc tgcaggcaac ccatatccca   300
tacaccttcg gtcaaggaac taaactggaa attaaacgta ctgttggctgc accatctgtc   360
ttcatcttcc cgccatctga tgagcagttg aaatctggaa ctgcctctgt tgtgtgcctg   420
ctgaataact ctatcccag agaggccaaa gtacagtgga aggtggataa cgccctccaa    480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

```
SEQ ID NO: 76          moltype = DNA  length = 1353
FEATURE                Location/Qualifiers
misc_feature           1..1353
                       note = Description of Artificial Sequence: Synthetic
                       polynucleotide
misc_feature           1..1353
                       note = CD19 (8B8-7H07)heavy chain DNA
source                 1..1353
                       mol_type = other DNA
                       organism = synthetic construct
SEQUENCE: 76
caggtgcaat tggttcaatc tggtgctgaa gtaaaaaaac cgggcgcttc cgttaaagtg   60
agctgcaaag catctggtta caccttcact gactatatca tgcactgggt tcgtcaggcc   120
ccgggccagg gtctggagtg gatgggctac attaacccat acaacgacgg ttccaaatat   180
accgagaaat tccagggccg cgtcacgatg accagcgaca cttctatctc caccgcgtac   240
atggaactgt ctagactgcg ttctgacgac accgctgttt actattgtgc acgcggtacc   300
tactactacg gttctgaact gtttgattac tggggccaag gtaccacggt gaccgtaagc   360
tctgctagca ccaagggccc atcggtcttc cccctggcac cctcctccaa gagcacctct   420
gggggcacag cggccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gaaagttgag   660
cccaaatctt gtgacaaaac tcacacatgc ccaccgtgcc cagcacctga gctgcaggg   720
ggaccgtcag tcttcctctt ccccccaaaa cccaaggaca ccctcatgat ctcccggacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgtgtggt cagcgtcctc accgtcctgc accaggactg gctgaatggc   960
aaggagtaca agtgcaaggt ctccaacaaa gccctcccag cccccatcga gaaaaccatc   1020
tccaaagcca aagggcagcc ccgagaacca caggtgtaca ccctgccccc atcccgggat   1080
gagctgacca gaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

```
SEQ ID NO: 77          moltype = AA  length = 219
FEATURE                Location/Qualifiers
REGION                 1..219
                       note = Description of Artificial Sequence: Synthetic
                       polypeptide
REGION                 1..219
                       note = CD19 (8B8-7H07)light chain
source                 1..219
                       mol_type = protein
                       organism = synthetic construct
SEQUENCE: 77
DIVMTQTPLS LSVTPGQPAS ISCKSSQSLE TSTGNTYLNW YLQKPGQSPQ LLIYRVSKRF   60
SGVPDRFSGS GSGTDFTLKI SRVEAEDVGV YYCLQATHIP YTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219
```

```
SEQ ID NO: 78          moltype = AA  length = 451
FEATURE                Location/Qualifiers
REGION                 1..451
                       note = Description of Artificial Sequence: Synthetic
                       polypeptide
REGION                 1..451
                       note = CD19 (8B8-7H07) heavy chain
source                 1..451
                       mol_type = protein
                       organism = synthetic construct
SEQUENCE: 78
QVQLVQSGAE VKKPGASVKV SCKASGYTFT DYIMHWVRQA PGQGLEWMGY INPYNDGSKY   60
TEKFQGRVTM TSDTSISTAY MELSRLRSDD TAVYYCARGT YYYGSELFDY WGQGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALGAPIEKTI SKAKGQPREP QVYTLPPSRD   360
```

```
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                  451

SEQ ID NO: 79          moltype = DNA  length = 657
FEATURE                Location/Qualifiers
misc_feature           1..657
                       note = Description of Artificial Sequence: Synthetic
                       polynucleotide
misc_feature           1..657
                       note = CD19 (8B8-2B03) light chain DNA
misc_difference        320..321
                       note = modified_base - a, c, g or t
source                 1..657
                       mol_type = other DNA
                       organism = synthetic construct SEQUENCE: 79
gatattgtta tgactcaaac tccactgtct ctgtccgtga ccccgggtca gccagcgagc  60
atttcttgca aatccagcca atctctggaa acctccaccg gcaacacgta cctgaactgg  120
tatctccaga aaccgggtca gagcccgcag ctgctgatct accgtgtatc taagcgcttc  180
tccggcgttc ctgatcgttt cagcggttct ggatccggca ccgactttac tctgaaaatc  240
agccgtgtga aagctgaaga cgttggcgtc tactattgtc tgcagttgac ccacgttccg  300
tacaccttcg gtcaaggaan naaactggaa attaaacgta cggttggctgc accatctgct  360
ttcatcttcc cgccatctga tgagcagttg aaatctggaa ctgcctctgt tgtgtgcctg  420
ctgaataact ctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt    657

SEQ ID NO: 80          moltype = DNA  length = 1353
FEATURE                Location/Qualifiers
misc_feature           1..1353
                       note = Description of Artificial Sequence: Synthetic
                       polynucleotide
misc_feature           1..1353
                       note = CD19 (8B8-2B03)heavy chain DNA
source                 1..1353
                       mol_type = other DNA
                       organism = synthetic construct SEQUENCE: 80
caggtgcaat tggttcaatc tggtgctgaa gtaaaaaaac cgggcgcttc cgttaaagtg  60
agctgcaaag catctggtta caccttcact gactatatca cgcactgggt tcgtcaggcc  120
ccgggccagg gtctggagtg gatgggctac attaacccat acaacgacgg ttccaaatat  180
accgagaaat tccagggccg cgtcacgatg accagcgaca cttctatctc caccgcgtac  240
atggaactgt ctagactgcg ttctgacgac accgctgttt actattgtgc acgcggtacc  300
tactactacg gtccagatct gtttgattac tggggccaag gtaccacggt gaccgtaagc  360
tctgctagca ccaagggccc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga agctgcaggg  720
ggaccgtcag tcttcctctt cccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca gtgcaaggt ctccaacaaa gccctcggcg ccccccatcga gaaaaccatc  1020
tccaaagcca aagggcagcc ccgagaacca caggtgtaca ccctgccccc atcccgggat  1080
gagctgacca gaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                                1353

SEQ ID NO: 81          moltype = AA  length = 219
FEATURE                Location/Qualifiers
REGION                 1..219
                       note = Description of Artificial Sequence: Synthetic
                       polypeptide
REGION                 1..219
                       note = CD19 (8B8-2B03) light chain
VARIANT                107
                       note = MOD_RES - Any naturally occurring amino acid
source                 1..219
                       mol_type = protein
                       organism = synthetic construct SEQUENCE: 81
DIVMTQTPLS LSVTPGQPAS ISCKSSQSLE TSTGNTYLNW YLQKPGQSPQ LLIYRVSKRF  60
SGVPDRFSGS GSGTDFTLKI SRVEAEDVGV YYCLQLTHVP YTFGQGXKLE IKRTVAAPSV  120
FIFPPSDEQL KSGTASVVCL LNNFYPREAK VQWKVDNALQ SGNSQESVTE QDSKDSTYSL  180
```

```
SSTLTLSKAD YEKHKVYACE VTHQGLSSPV TKSFNRGEC                          219

SEQ ID NO: 82            moltype = AA   length = 451
FEATURE                  Location/Qualifiers
REGION                   1..451
                         note = Description of Artificial Sequence: Synthetic
                          polypeptide
REGION                   1..451
                         note = CD19 (8B8-2B03) heavy chain
source                   1..451
                         mol_type = protein
                         organism = synthetic construct
SEQUENCE: 82
QVQLVQSGAE VKKPGASVKV SCKASGYTFT DYITHWVRQA PGQGLEWMGY INPYNDGSKY   60
TEKFQGRVTM TSDTSISTAY MELSRLRSDD TAVYYCARGT YYYGPDLFDY WGQGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALGAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 83            moltype = DNA   length = 657
FEATURE                  Location/Qualifiers
misc_feature             1..657
                         note = Description of Artificial Sequence: Synthetic
                          polynucleotide
misc_feature             1..657
                         note = CD19 (8B8-5A07)light chain DNA
source                   1..657
                         mol_type = other DNA
                         organism = synthetic construct
SEQUENCE: 83
gatattgtta tgactcaaac tccactgtct ctgtccgtga ccccgggtca gccagcgagc   60
atttcttgca aatccagcca atctctggaa acctccaccg gcaacacgta cctgaactgg   120
tatctccaga aaccgggtca gagcccgcag ctgctgatct accgtgtatc taagcgcttc   180
tccggcgttc ctgatcgttt cagcggttct ggatccggca ccgactttac tctgaaaatc   240
agccgtgtgg aagctgaaga cgttggcgtc tactattgtc tgcagccagg tcattaccca   300
ggtaccttcg gtcaaggaac taaactggaa attaaacgta cggtggctgc accatctgtc   360
ttcatcttcc cgccatctga tgagcagttg aaatctggaa ctgcctctgt tgtgtgcctg   420
ctgaataact ctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657

SEQ ID NO: 84            moltype = DNA   length = 1353
FEATURE                  Location/Qualifiers
misc_feature             1..1353
                         note = Description of Artificial Sequence: Synthetic
                          polynucleotide
misc_feature             1..1353
                         note = CD19 (8B8-5A07)heavy chain DNA
source                   1..1353
                         mol_type = other DNA
                         organism = synthetic construct
SEQUENCE: 84
caggtgcaat ggttcaatc tggtgctgaa gtaaaaaaac cgggcgcttc cgttaaagtg   60
agctgcaaag catctggtta caccttcact gactatatca tgcactgggt tcgtcaggcc   120
ccgggccagg tctggagtg gatgggctac attaacccat acaacgacgg ttccaaatat   180
accgagaaat tccagggccg cgtcacgatg accagcgaca cttctatctc caccgcgtac   240
atggaactgt ctagactgcg ttctgacgac accgctgttt actattgtgc acgcggtact   300
tactactacg gttccgccct ctttgattac tggggccaag gtaccacggt gaccgtaagc   360
tctgctagca ccaagggccc atcggtcttc cccctggcac cctcctccaa gagcacctct   420
gggggcacag cggccctggg ctgcctggtc aaggactact ccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gaaagttgag   660
cccaaatctt gtgacaaaac tcacacatgc ccaccgtgcc cagcacctga agctgcaggg   720
ggaccgtcag tcttcctctt ccccccaaaa cccaaggaca cctcatgat ctcccggacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacg accgtgtggt cagcgtcctc accgtcctgc accaggactg gctgaatggc   960
aaggagtaca agtgcaaggt ctccaacaaa gccctcggcg ccccatcga gaaaaccatc   1020
tccaaagcca aagggcagcc ccgagaacca caggtgtaca ccctgccccc atcccgggat   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                               1353
```

-continued

```
SEQ ID NO: 85            moltype = AA  length = 219
FEATURE                  Location/Qualifiers
REGION                   1..219
                         note = Description of Artificial Sequence: Synthetic
                          polypeptide
REGION                   1..219
                         note = CD19 (8B8-5A07)light chain
source                   1..219
                         mol_type = protein
                         organism = synthetic construct
SEQUENCE: 85
DIVMTQTPLS LSVTPGQPAS ISCKSSQSLE TSTGNTYLNW YLQKPGQSPQ LLIYRVSKRF  60
SGVPDRFSGS GSGTDFTLKI SRVEAEDVGV YYCLQPGHYP GTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                          219

SEQ ID NO: 86            moltype = AA  length = 451
FEATURE                  Location/Qualifiers
REGION                   1..451
                         note = Description of Artificial Sequence: Synthetic
                          polypeptide
REGION                   1..451
                         note = CD19 (8B8-5A07)heavy chain
source                   1..451
                         mol_type = protein
                         organism = synthetic construct
SEQUENCE: 86
QVQLVQSGAE VKKPGASVKV SCKASGYTFT DYIMHWVRQA PGQGLEWMGY INPYNDGSKY  60
TEKFQGRVTM TSDTSISTAY MELSRLRSDD TAVYYCARGT YYYGSALFDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                  451

SEQ ID NO: 87            moltype = DNA  length = 657
FEATURE                  Location/Qualifiers
misc_feature             1..657
                         note = Description of Artificial Sequence: Synthetic
                          polynucleotide
misc_feature             1..657
                         note = CD19 (8B8-5D08) light chain DNA
source                   1..657
                         mol_type = other DNA
                         organism = synthetic construct
SEQUENCE: 87
gatattgtta tgactcaaac tccactgtct ctgtccgtga ccccgggtca gccagcgagc  60
atttcttgca aatccagcca atctctggaa acctccaccg gcaacacgta cctgaactgg  120
tatctccaga aaccgggtca gagcccgcag ctgctgatct accgtgtatc taagcgcttc  180
tccggcgttc ctgatcgttt cagcggttct ggatccggca ccgactttac tctgaaaatc  240
agccgtgtgg aagctgaaga cgttggcgtc tactattgtc tgcagctgac ccatgaacca  300
tacaccttcg gtcaaggaac taaactggaa attaaacgta cggtggctgc accatctgtc  360
ttcatcttcc cgccatctga tgagcagttg aaatctggaa ctgcctctgt tgtgtgcctg  420
ctgaataact ctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt      657

SEQ ID NO: 88            moltype = DNA  length = 1353
FEATURE                  Location/Qualifiers
misc_feature             1..1353
                         note = Description of Artificial Sequence: Synthetic
                          polynucleotide
misc_feature             1..1353
                         note = CD19 (8B8-5D08)heavy chain DNA
source                   1..1353
                         mol_type = other DNA
                         organism = synthetic construct
SEQUENCE: 88
caggtgcaat ggttcaatc tggtgctgaa gtaaaaaaac cgggcgcttc cgttaaagtg  60
agctgcaaag catctggtta caccttcact gactatatca tgcactgggt tcgtcaggcc  120
ccgggccagg gtctggagtg gatgggctac attaacccat acaacgacgg ttccaaatat  180
accgagaaat tccagggccg cgtcacgatg accagcgaca cttctatctc caccgcgtac  240
atggaactgt ctagactgcg ttctgacgac accgctgttt actattgtgc acgcggtacc  300
tactactacg gttctgaact gtttgattac tggggccaag gtaccacggt gaccgtaagc  360
tctgctagca ccaagggccc atcggtcttc cccctggcac cctcctccaa gagcacctct  420
gggggcacag cggccctggg ctgcctggtc aaggactact ccccgaaccc ggtgacggtg  480
```

-continued

```
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga agctgcaggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcggcg cccccatcga gaaaaccatc  1020
tccaaagcca aagggcagcc ccgagaacca caggtgtaca ccctgccccc atcccgggat  1080
gagctgacca gaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                                1353
```

SEQ ID NO: 89          moltype = AA  length = 219
FEATURE              Location/Qualifiers
REGION               1..219
                      note = Description of Artificial Sequence: Synthetic
                      polypeptide
REGION               1..219
                      note = CD19 (8B8-5D08)light chain
source               1..219
                      mol_type = protein
                      organism = synthetic construct
SEQUENCE: 89
```
DIVMTQTPLS LSVTPGQPAS ISCKSSQSLE TSTGNTYLNW YLQKPGQSPQ LLIYRVSKRF  60
SGVPDRFSGS GSGTDFTLKI SRVEAEDVGV YYCLQLTHEP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219
```

SEQ ID NO: 90          moltype = AA  length = 451
FEATURE              Location/Qualifiers
REGION               1..451
                      note = Description of Artificial Sequence: Synthetic
                      polypeptide
REGION               1..451
                      note = CD19 (8B8-5D08) heavy chain
source               1..451
                      mol_type = protein
                      organism = synthetic construct
SEQUENCE: 90
```
QVQLVQSGAE VKKPGASVKV SCKASGYTFT DYIMHWVRQA PGQGLEWMGY INPYNDGSKY  60
TEKFQGRVTM TSDTSISTAY MELSRLRSDD TAVYYCARGT YYYGSELFDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALGAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451
```

SEQ ID NO: 91          moltype = DNA  length = 657
FEATURE              Location/Qualifiers
misc_feature        1..657
                      note = Description of Artificial Sequence: Synthetic
                      polynucleotide
misc_feature        1..657
                      note = CD19 (8B8-5B08)light chain DNA
source               1..657
                      mol_type = other DNA
                      organism = synthetic construct
SEQUENCE: 91
```
gatattgtta tgactcaaac tccactgtct ctgtccgtga ccccgggtca gccagcgagc  60
atttcttgca atccagcca atctctggaa acctccaccg gcaacacgta cctgaactgg  120
tatctccaga aaccgggtca gagcccgcag ctgctgatct accgtgtatc taagcgcttc  180
tccggcgttc ctgatcgttt cagcggttct ggatccggca ccgactttac tctgaaaatc  240
agccgtgtgg aagctgaaga cgttggcgtc tactattgtc tgcagcttga ttcttaccca  300
aacaccttcg gtcaaggaac taaactggaa attaaacgta ccgttgctgc accatctgtc  360
ttcatcttcc cgccatctga tgagcagttg aaatctggaa ctgcctctgt tgtgtgcctg  420
ctgaataact ctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657
```

SEQ ID NO: 92          moltype = DNA  length = 1353
FEATURE              Location/Qualifiers
misc_feature        1..1353
                      note = Description of Artificial Sequence: Synthetic

```
                        polynucleotide
misc_feature            1..1353
                        note = CD19 (8B8-5B08) heavy chain DNA
source                  1..1353
                        mol_type = other DNA
                        organism = synthetic construct
SEQUENCE: 92
caggtgcaat tggttcaatc tggtgctgaa gtaaaaaaac cgggcgcttc cgttaaagtg    60
agctgcaaag catctggtta caccttcact gactatatca tgcactgggt tcgtcaggcc   120
ccgggccagg gtctggagtg gatgggctac attaacccat acaacgacgg ttccaaatat   180
accgagaaat tccagggccg cgtcacgatg accagcgaca cttctatctc caccgcgtac   240
atggaactgt ctagactgcg ttctgacgac accgctgttt actattgtgc acgcggtacc   300
tactactacg gtccacagct gtttgattac tggggccaag gtaccacggt gaccgtaagc   360
tctgctagca ccaagggccc atcggtcttc ccctgccac cctcctccaa gagcacctct   420
gggggcacag cggccctggg ctgcctggtc aaggactact ccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gaaagttgag   660
cccaaatctt gtgacaaaac tcacacatgc ccaccgtgcc cagcacctga agctgcaggg   720
ggaccgtcag tcttcctctt cccccaaaa cccaaggaca ccctcatgat ctcccggacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgtgtggt cagcgtcctc accgtcctgc accaggactg gctgaatggc   960
aaggagtaca agtgcaaggt ctccaacaaa gccctcggcg cccccatcga gaaaaccatc  1020
tccaaagcca aagggcagcc ccgagaacca caggtgtaca ccctgccccc atcccgggat  1080
gagctgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                                1353

SEQ ID NO: 93          moltype = AA  length = 219
FEATURE                Location/Qualifiers
REGION                 1..219
                       note = Description of Artificial Sequence: Synthetic
                        polypeptide
REGION                 1..219
                       note = CD19 (8B8-5B08) light chain
source                 1..219
                       mol_type = protein
                       organism = synthetic construct
SEQUENCE: 93
DIVMTQTPLS LSVTPGQPAS ISCKSSQSLE TSTGNTYLNW YLQKPGQSPQ LLIYRVSKRF    60
SGVPDRFSGS GSGTDFTLKI SRVEAEDVGV YYCLQLDSYP NTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 94          moltype = AA  length = 451
FEATURE                Location/Qualifiers
REGION                 1..451
                       note = Description of Artificial Sequence: Synthetic
                        polypeptide
REGION                 1..451
                       note = CD19 (8B8-5B08)heavy chain
source                 1..451
                       mol_type = protein
                       organism = synthetic construct
SEQUENCE: 94
QVQLVQSGAE VKKPGASVKV SCKASGYTFT DYIMHWVRQA PGQGLEWMGY INPYNDGSKY    60
TEKFQGRVTM TSDTSISTAY MELSRLRSDD TAVYYCARGT YYYGPQLFDY WGQGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALGAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 95          moltype = DNA  length = 657
FEATURE                Location/Qualifiers
misc_feature           1..657
                       note = Description of Artificial Sequence: Synthetic
                        polynucleotide
misc_feature           1..657
                       note = CD19 (8B8-5H09) light chain DNA
source                 1..657
                       mol_type = other DNA
                       organism = synthetic construct
SEQUENCE: 95
gatattgtta tgactcaaac tccactgtct ctgtccgtga ccccgggtca gccagcgagc    60
```

```
atttcttgca aatccagcca atctctggaa tcttccaccg gcaacacgta cctgaactgg   120
tatctccaga aaccgggtca gagcccgcag ctgctgatct accgtgtatc taagcgcttc   180
tccggcgttc ctgatcgttt cagcggttct ggatccggca ccgactttac tctgaaaatc   240
agccgtgtgg aagctgaaga cgttggcgtc tactattgtc tgcagctgat cgattaccca   300
gttaccttcg gtcaaggaac taaactggaa attaaacgta cggtggctgc accatctgtc   360
ttcatcttcc cgccatctga tgagcagttg aaatctggaa ctgcctctgt tgtgtgcctg   420
ctgaataact ctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

SEQ ID NO: 96          moltype = DNA   length = 1353
FEATURE                 Location/Qualifiers
misc_feature          1..1353
                       note = Description of Artificial Sequence: Synthetic
                       polynucleotide
misc_feature          1..1353
                       note = CD19 (8B8-5H09)heavy chain DNA
source                 1..1353
                       mol_type = other DNA
                       organism = synthetic construct
SEQUENCE: 96

```
caggtgcaat tggttcaatc tggtgctgaa gtaaaaaaac cgggcgcttc cgttaaagtg   60
agctgcaaag catctggtta caccttcact gactatatca tgcactgggt tcgtcaggcc   120
ccgggccagg gtctggagtg gatgggctac attaacccat acaacgacgg ttccaaatat   180
accgagaaat tccagggccg cgtcacgatg accagcgaca cttctatctc caccgcgtac   240
atggaactgt ctagactgcg ttctgacgac accgctgttt actattgtgc acgcggtacc   300
tactactacg gttctgcact gtttgattac tggggccaag gtaccacggt gaccgtaagc   360
tctgctagca ccaagggccc atcggtcttc cccctggcac cctcctccaa gagcacctct   420
gggggcacag cggccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gaaagttgag   660
cccaaatctt gtgacaaaac tcacacatgc ccaccgtgcc cagcacctga gctcgcaggg   720
ggaccgtcag tcttcctctt cccccccaaaa cccaaggaca ccctcatgat ctcccggacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgtgtggt cagcgtcctc accgtcctgc accaggactg gctgaatggc   960
aaggagtaca agtgcaaggt ctccaacaaa gccctcccag cccccatcga gaaaaccatc   1020
tccaaagcca aagggcagcc ccgagaacca caggtgtaca ccctgccccc atcccgggat   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                 1353
```

SEQ ID NO: 97          moltype = AA   length = 219
FEATURE                 Location/Qualifiers
REGION                 1..219
                       note = Description of Artificial Sequence: Synthetic
                       polypeptide
REGION                 1..219
                       note = CD19 (8B8-5H09)light chain
source                 1..219
                       mol_type = protein
                       organism = synthetic construct
SEQUENCE: 97

```
DIVMTQTPLS LSVTPGQPAS ISCKSSQSLE SSTGNTYLNW YLQKPGQSPQ LLIYRVSKRF   60
SGVPDRFSGS GSGTDFTLKI SRVEAEDVGV YYCLQLGYDP VTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                           219
```

SEQ ID NO: 98          moltype = AA   length = 451
FEATURE                 Location/Qualifiers
REGION                 1..451
                       note = Description of Artificial Sequence: Synthetic
                       polypeptide
REGION                 1..451
                       note = CD19 (8B8-5H09)heavy chain
source                   1..451
                       mol_type = protein
                       organism = synthetic construct
SEQUENCE: 98

```
QVQLVQSGAE VKKPGASVKV SCKASGYTFT DYIMHWVRQA PGQGLEWMGY INPYNDGSKY   60
TEKFQGRVTM TSDTSISTAY MELSRLRSDD TAVYYCARGT YYYGSALFDY WGQGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALGAPIEKTI SKAKGQPREP QVYTLPPSRD   360
```

```
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                   451

SEQ ID NO: 99           moltype = AA  length = 121
FEATURE                 Location/Qualifiers
REGION                  1..121
                        note = Description of Artificial Sequence: Synthetic
                         polypeptide
REGION                  1..121
                        note = CD19 (8B8-2B11) VH
source                  1..121
                        mol_type = protein
                        organism = synthetic construct
SEQUENCE: 99
QVQLVQSGAE VKKPGASVKV SCKASGYTFT DYIMHWVRQA PGQGLEWMGY INPYNDGSKY   60
TEKFQGRVTM TSDTSISTAY MELSRLRSDD TAVYYCARGT YYYGPQLFDY WGQGTTVTVS   120
S                                                                    121

SEQ ID NO: 100          moltype = AA  length = 112
FEATURE                 Location/Qualifiers
REGION                  1..112
                        note = Description of Artificial Sequence: Synthetic
                         polypeptide
REGION                  1..112
                        note = CD19 (8B8-2B11) VL
source                  1..112
                        mol_type = protein
                        organism = synthetic construct
SEQUENCE: 100
DIVMTQTPLS LSVTPGQPAS ISCKSSQSLE TSTGTTYLNW YLQKPGQSPQ LLIYRVSKRF   60
SGVPDRFSGS GSGTDFTLKI SRVEAEDVGV YYCLQLLEDP YTFGQGTKLE IK            112

SEQ ID NO: 101          moltype = AA  length = 121
FEATURE                 Location/Qualifiers
REGION                  1..121
                        note = Description of Artificial Sequence: Synthetic
                         polypeptide
REGION                  1..121
                        note = CD19 (8B8-7H07) VH
source                  1..121
                        mol_type = protein
                        organism = synthetic construct
SEQUENCE: 101
QVQLVQSGAE VKKPGASVKV SCKASGYTFT DYIMHWVRQA PGQGLEWMGY INPYNDGSKY   60
TEKFQGRVTM TSDTSISTAY MELSRLRSDD TAVYYCARGT YYYGSELFDY WGQGTTVTVS   120
S                                                                    121

SEQ ID NO: 102          moltype = AA  length = 112
FEATURE                 Location/Qualifiers
REGION                  1..112
                        note = Description of Artificial Sequence: Synthetic
                         polypeptide
REGION                  1..112
                        note = CD19 (8B8-7H07) VL
source                  1..112
                        mol_type = protein
                        organism = synthetic construct
SEQUENCE: 102
DIVMTQTPLS LSVTPGQPAS ISCKSSQSLE TSTGNTYLNW YLQKPGQSPQ LLIYRVSKRF   60
SGVPDRFSGS GSGTDFTLKI SRVEAEDVGV YYCLQATHIP YTFGQGTKLE IK            112

SEQ ID NO: 103          moltype = AA  length = 121
FEATURE                 Location/Qualifiers
REGION                  1..121
                        note = Description of Artificial Sequence: Synthetic
                         polypeptide
REGION                  1..121
                        note = CD19 (8B8-2B03) VH
source                  1..121
                        mol_type = protein
                        organism = synthetic construct
SEQUENCE: 103
QVQLVQSGAE VKKPGASVKV SCKASGYTFT DYITHWVRQA PGQGLEWMGY INPYNDGSKY   60
TEKFQGRVTM TSDTSISTAY MELSRLRSDD TAVYYCARGT YYYGPDLFDY WGQGTTVTVS   120
S                                                                    121

SEQ ID NO: 104          moltype = AA  length = 112
FEATURE                 Location/Qualifiers
REGION                  1..112
```

-continued

```
                            note = Description of Artificial Sequence: Synthetic
                             polypeptide
REGION                      1..112
                            note = CD19 (8B8-2B03) VL
VARIANT                     107
                            note = MOD_RES - Any naturally occurring amino acid
source                      1..112
                            mol_type = protein
                            organism = synthetic construct
SEQUENCE: 104
DIVMTQTPLS LSVTPGQPAS ISCKSSQSLE TSTGNTYLNW YLQKPGQSPQ LLIYRVSKRF  60
SGVPDRFSGS GSGTDFTLKI SRVEAEDVGV YYCLQLTHVP YTFGQGXKLE IK          112

SEQ ID NO: 105              moltype = AA  length = 121
FEATURE                     Location/Qualifiers
REGION                      1..121
                            note = Description of Artificial Sequence: Synthetic
                             polypeptide
REGION                      1..121
                            note = CD19 (8B8-5A07) VH
source                      1..121
                            mol_type = protein
                            organism = synthetic construct
SEQUENCE: 105
QVQLVQSGAE VKKPGASVKV SCKASGYTFT DYIMHWVRQA PGQGLEWMGY INPYNDGSKY  60
TEKFQGRVTM TSDTSISTAY MELSRLRSDD TAVYYCARGT YYYGSALFDY WGQGTTVTVS  120
S                                                                  121

SEQ ID NO: 106              moltype = AA  length = 112
FEATURE                     Location/Qualifiers
REGION                      1..112
                            note = Description of Artificial Sequence: Synthetic
                             polypeptide
REGION                      1..112
                            note = CD19 (8B8-5A07) VL
source                      1..112
                            mol_type = protein
                            organism = synthetic construct
SEQUENCE: 106
DIVMTQTPLS LSVTPGQPAS ISCKSSQSLE TSTGNTYLNW YLQKPGQSPQ LLIYRVSKRF  60
SGVPDRFSGS GSGTDFTLKI SRVEAEDVGV YYCLQPGHYP GTFGQGTKLE IK          112

SEQ ID NO: 107              moltype = AA  length = 121
FEATURE                     Location/Qualifiers
REGION                      1..121
                            note = Description of Artificial Sequence: Synthetic
                             polypeptide
REGION                      1..121
                            note = CD19 (8B8-5D08) VH
source                      1..121
                            mol_type = protein
                            organism = synthetic construct
SEQUENCE: 107
QVQLVQSGAE VKKPGASVKV SCKASGYTFT DYIMHWVRQA PGQGLEWMGY INPYNDGSKY  60
TEKFQGRVTM TSDTSISTAY MELSRLRSDD TAVYYCARGT YYYGSELFDY WGQGTTVTVS  120
S                                                                  121

SEQ ID NO: 108              moltype = AA  length = 112
FEATURE                     Location/Qualifiers
REGION                      1..112
                            note = Description of Artificial Sequence: Synthetic
                             polypeptide
REGION                      1..112
                            note = CD19 (8B8-5D08) VL
source                      1..112
                            mol_type = protein
                            organism = synthetic construct
SEQUENCE: 108
DIVMTQTPLS LSVTPGQPAS ISCKSSQSLE TSTGNTYLNW YLQKPGQSPQ LLIYRVSKRF  60
SGVPDRFSGS GSGTDFTLKI SRVEAEDVGV YYCLQLTHEP YTFGQGTKLE IK          112

SEQ ID NO: 109              moltype = AA  length = 121
FEATURE                     Location/Qualifiers
REGION                      1..121
                            note = Description of Artificial Sequence: Synthetic
                             polypeptide
REGION                      1..121
                            note = CD19 (8B8-5B08) VH
source                      1..121
```

```
                              mol_type = protein
                              organism = synthetic construct
SEQUENCE: 109
QVQLVQSGAE VKKPGASVKV SCKASGYTFT DYIMHWVRQA PGQGLEWMGY INPYNDGSKY   60
TEKFQGRVTM TSDTSISTAY MELSRLRSDD TAVYYCARGT YYYGPQLFDY WGQGTTVTVS  120
S                                                                 121

SEQ ID NO: 110           moltype = AA  length = 112
FEATURE                  Location/Qualifiers
REGION                   1..112
                         note = Description of Artificial Sequence: Synthetic
                          polypeptide
REGION                   1..112
                         note = CD19 (8B8-5B08) VL
source                   1..112
                         mol_type = protein
                         organism = synthetic construct
SEQUENCE: 110
DIVMTQTPLS LSVTPGQPAS ISCKSSQSLE TSTGNTYLNW YLQKPGQSPQ LLIYRVSKRF   60
SGVPDRFSGS GSGTDFTLKI SRVEAEDVGV YYCLQLDSYP NTFGQGTKLE IK          112

SEQ ID NO: 111           moltype = AA  length = 121
FEATURE                  Location/Qualifiers
REGION                   1..121
                         note = Description of Artificial Sequence: Synthetic
                          polypeptide
REGION                   1..121
                         note = CD19 (8B8-5H09) VH
source                   1..121
                         mol_type = protein
                         organism = synthetic construct
SEQUENCE: 111
QVQLVQSGAE VKKPGASVKV SCKASGYTFT DYIMHWVRQA PGQGLEWMGY INPYNDGSKY   60
TEKFQGRVTM TSDTSISTAY MELSRLRSDD TAVYYCARGT YYYGSALFDY WGQGTTVTVS  120
S                                                                 121

SEQ ID NO: 112           moltype = AA  length = 112
FEATURE                  Location/Qualifiers
REGION                   1..112
                         note = Description of Artificial Sequence: Synthetic
                          polypeptide
REGION                   1..112
                         note = CD19 (8B8-5H09) VL
source                   1..112
                         mol_type = protein
                         organism = synthetic construct
SEQUENCE: 112
DIVMTQTPLS LSVTPGQPAS ISCKSSQSLE SSTGNTYLNW YLQKPGQSPQ LLIYRVSKRF   60
SGVPDRFSGS GSGTDFTLKI SRVEAEDVGV YYCLQLIDYP VTFGQGTKLE IK          112

SEQ ID NO: 113           moltype = AA  length = 121
FEATURE                  Location/Qualifiers
REGION                   1..121
                         note = Description of Artificial Sequence: Synthetic
                          polypeptide
REGION                   1..121
                         note = CD19 (8B8) VH
source                   1..121
                         mol_type = protein
                         organism = synthetic construct
SEQUENCE: 113
QVQLVQSGAE VKKPGASVKV SCKASGYTFT DYIMHWVRQA PGQGLEWMGY INPYNDGSKY   60
TEKFQGRVTM TSDTSISTAY MELSRLRSDD TAVYYCARGT YYYGSALFDY WGQGTTVTVS  120
S                                                                 121

SEQ ID NO: 114           moltype = AA  length = 112
FEATURE                  Location/Qualifiers
REGION                   1..112
                         note = Description of Artificial Sequence: Synthetic
                          polypeptide
REGION                   1..112
                         note = CD19 (8B8) VL
source                   1..112
                         mol_type = protein
                         organism = synthetic construct
SEQUENCE: 114
DIVMTQTPLS LSVTPGQPAS ISCKSSQSLE NSNGNTYLNW YLQKPGQSPQ LLIYRVSKRF   60
SGVPDRFSGS GSGTDFTLKI SRVEAEDVGV YYCLQLTHVP YTFGQGTKLE IK          112
```

-continued

```
SEQ ID NO: 115          moltype = AA  length = 556
FEATURE                 Location/Qualifiers
source                  1..556
                        mol_type = protein
                        organism = Homo sapiens
SEQUENCE: 115
MPPPRLLFFL LFLTPMEVRP EEPLVVKVEE GDNAVLQCLK GTSDGPTQQL TWSRESPLKP  60
FLKLSLGLPG LGIHMRPLAI WLFIFNVSQQ MGGFYLCQPG PPSEKAWQPG WTVNVEGSGE  120
LFRWNVSDLG GLGCGLKNRS SEGPSSPSGK LMSPKLYVWA KDRPEIWEGE PPCLPPRDSL  180
NQSLSQDLTM APGSTLWLSC GVPPDSVSRG PLSWTHVHPK GPKSLLSLEL KDDRPARDMW  240
VMETGLLLPR ATAQDAGKYY CHRGNLTMSF HLEITARPVL WHWLLRTGGW KVSAVTLAYL  300
IFCLCSLVGI LHLQRALVLR RKRKRMTDPT RRFFKVTPPP GSGPQNQYGN VLSLPTPTSG  360
LGRAQRWAAG LGGTAPSYGN PSSDVQADGA LGSRSPPGVG PEEEEGEGYE EPDSEEDSEF  420
YENDSNLGQD QLSQDGSGYE NPEDEPLGPE DEDSFSNAES YENEDEELTQ PVARTMDFLS  480
PHGSAWDPSR EATSLGSQSY EDMRGILYAA PQLRSIRGQP GPNHEEDADS YENMDNPDGP  540
DPAWGGGGRM GTWSTR                                                 556

SEQ ID NO: 116          moltype = AA  length = 50
FEATURE                 Location/Qualifiers
REGION                  1..50
                        note = Description of Artificial Sequence: Synthetic
                        polypeptide
VARIANT                 1..50
                        note = MISC_FEATURE - This sequence may encompass 1-10 "Gly
                        Gly Gly Gly Ser"repeating units
REGION                  1..50
                        note = See specification as filed for detailed description
                        of substitutions and preferred embodiments
source                  1..50
                        mol_type = protein
                        organism = synthetic construct
SEQUENCE: 116
GGGGSGGGGS GGGGSGGGGS GGGGSGGGGS GGGGSGGGGS GGGGSGGGGS            50

SEQ ID NO: 117          moltype = AA  length = 50
FEATURE                 Location/Qualifiers
REGION                  1..50
                        note = Description of Artificial Sequence: Synthetic
                        polypeptide
VARIANT                 1..50
                        note = MISC_FEATURE - This sequence may encompass 1-10 "Ser
                        Gly Gly Gly Gly"repeating units
REGION                  1..50
                        note = See specification as filed for detailed description
                        of substitutions and preferred embodiments
source                  1..50
                        mol_type = protein
                        organism = synthetic construct
SEQUENCE: 117
SGGGGSGGGG SGGGGSGGGG SGGGGSGGGG SGGGGSGGGG SGGGGSGGGG            50

SEQ ID NO: 118          moltype = AA  length = 54
FEATURE                 Location/Qualifiers
REGION                  1..54
                        note = Description of Artificial Sequence: Synthetic
                        polypeptide
VARIANT                 5..54
                        note = MISC_FEATURE - This region may encompass 1-10 "Ser
                        Gly Gly Gly Gly"repeating units
REGION                  1..54
                        note = See specification as filed for detailed description
                        of substitutions and preferred embodiments
source                  1..54
                        mol_type = protein
                        organism = synthetic construct
SEQUENCE: 118
GGGGSGGGGS GGGGSGGGGS GGGGSGGGGS GGGGSGGGGS GGGGSGGGGS GGGG       54

SEQ ID NO: 119          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 119
PTPPTP                                                            6

SEQ ID NO: 120          moltype = AA  length = 112
```

```
FEATURE              Location/Qualifiers
REGION               1..112
                     note = Description of Artificial Sequence: Synthetic
                      polypeptide
source               1..112
                     mol_type = protein
                     organism = synthetic construct
SEQUENCE: 120
DIVMTQTPLS LSVTPGQPAS ISCKSSQSLE NSNGNTYLNW YLQKPGQSPQ LLIYRVSKRF  60
SGVPDRFSGS GSGTDFTLKI SRVEAEDVGV YYCLQLTHVP YTFGQGTKLE IK          112

SEQ ID NO: 121       moltype = AA  length = 112
FEATURE              Location/Qualifiers
REGION               1..112
                     note = Description of Artificial Sequence: Synthetic
                      polypeptide
source               1..112
                     mol_type = protein
                     organism = synthetic construct
SEQUENCE: 121
DIVMTQTPLS LSVTPGQPAS ISCKSSQSLE SSTGNTYLNW YLQKPGQSPQ LLIYRVSKRF  60
SGVPDRFSGS GSGTDFTLKI SRVEAEDVGV YYCLQLIDYP VTFGQGTKLE IK          112

SEQ ID NO: 122       moltype = AA  length = 112
FEATURE              Location/Qualifiers
REGION               1..112
                     note = Description of Artificial Sequence: Synthetic
                      polypeptide
source               1..112
                     mol_type = protein
                     organism = synthetic construct
SEQUENCE: 122
DIVMTQTPLS LSVTPGQPAS ISCKSSQSLE TSTGNTYLNW YLQKPGQSPQ LLIYRVSKRF  60
SGVPDRFSGS GSGTDFTLKI SRVEAEDVGV YYCLQATHIP YTFGQGTKLE IK          112

SEQ ID NO: 123       moltype = AA  length = 112
FEATURE              Location/Qualifiers
REGION               1..112
                     note = Description of Artificial Sequence: Synthetic
                      polypeptide
source               1..112
                     mol_type = protein
                     organism = synthetic construct
SEQUENCE: 123
DIVMTQTPLS LSVTPGQPAS ISCKSSQSLE TSTGNTYLNW YLQKPGQSPQ LLIYRVSKRF  60
SGVPDRFSGS GSGTDFTLKI SRVEAEDVGV YYCLQLTHVP YTFGQGTKLE IK          112

SEQ ID NO: 124       moltype = AA  length = 112
FEATURE              Location/Qualifiers
REGION               1..112
                     note = Description of Artificial Sequence: Synthetic
                      polypeptide
source               1..112
                     mol_type = protein
                     organism = synthetic construct
SEQUENCE: 124
DIVMTQTPLS LSVTPGQPAS ISCKSSQSLE TSTGTTYLNW YLQKPGQSPQ LLIYRVSKRF  60
SGVPDRFSGS GSGTDFTLKI SRVEAEDVGV YYCLQLLEDP YTFGQGTKLE IK          112

SEQ ID NO: 125       moltype = AA  length = 112
FEATURE              Location/Qualifiers
REGION               1..112
                     note = Description of Artificial Sequence: Synthetic
                      polypeptide
source               1..112
                     mol_type = protein
                     organism = synthetic construct
SEQUENCE: 125
DIVMTQTPLS LSVTPGQPAS ISCKSSQSLE TSTGNTYLNW YLQKPGQSPQ LLIYRVSKRF  60
SGVPDRFSGS GSGTDFTLKI SRVEAEDVGV YYCLQPGHYP GTFGQGTKLE IK          112

SEQ ID NO: 126       moltype = AA  length = 112
FEATURE              Location/Qualifiers
REGION               1..112
                     note = Description of Artificial Sequence: Synthetic
                      polypeptide
source               1..112
                     mol_type = protein
                     organism = synthetic construct
```

```
SEQUENCE: 126
DIVMTQTPLS LSVTPGQPAS ISCKSSQSLE TSTGNTYLNW YLQKPGQSPQ LLIYRVSKRF 60
SGVPDRFSGS GSGTDFTLKI SRVEAEDVGV YYCLQLDSYP NTFGQGTKLE IK           112

SEQ ID NO: 127          moltype = AA  length = 112
FEATURE                 Location/Qualifiers
REGION                  1..112
                        note = Description of Artificial Sequence: Synthetic
                         polypeptide
source                  1..112
                        mol_type = protein
                        organism = synthetic construct
SEQUENCE: 127
DIVMTQTPLS LSVTPGQPAS ISCKSSQSLE TSTGNTYLNW YLQKPGQSPQ LLIYRVSKRF 60
SGVPDRFSGS GSGTDFTLKI SRVEAEDVGV YYCLQLTHEP YTFGQGTKLE IK           112

SEQ ID NO: 128          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 128
QVQLVQSGAE VKKPGASVKV SCKASGYTFT DYIMHWVRQA PGQGLEWMGY INPYNDGSKY 60
TEKFQGRVTM TSDTSISTAY MELSRLRSDD TAVYYCARGT YYYGSALFDY WGQGTTVTVS 120
S                                                                   121

SEQ ID NO: 129          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 129
QVQLVQSGAE VKKPGASVKV SCKASGYTFT DYIMHWVRQA PGQGLEWMGY INPYNDGSKY 60
TEKFQGRVTM TSDTSISTAY MELSRLRSDD TAVYYCARGT YYYGSALFDY WGQGTTVTVS 120
S                                                                   121

SEQ ID NO: 130          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 130
QVQLVQSGAE VKKPGASVKV SCKASGYTFT DYIMHWVRQA PGQGLEWMGY INPYNDGSKY 60
TEKFQGRVTM TSDTSISTAY MELSRLRSDD TAVYYCARGT YYYGSELFDY WGQGTTVTVS 120
S                                                                   121

SEQ ID NO: 131          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 131
QVQLVQSGAE VKKPGASVKV SCKASGYTFT DYITHWVRQA PGQGLEWMGY INPYNDGSKY 60
TEKFQGRVTM TSDTSISTAY MELSRLRSDD TAVYYCARGT YYYGPDLFDY WGQGTTVTVS 120
S                                                                   121

SEQ ID NO: 132          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 132
QVQLVQSGAE VKKPGASVKV SCKASGYTFT DYIMHWVRQA PGQGLEWMGY INPYNDGSKY 60
TEKFQGRVTM TSDTSISTAY MELSRLRSDD TAVYYCARGT YYYGPQLFDY WGQGTTVTVS 120
```

-continued

```
S                                                                                121

SEQ ID NO: 133           moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 133
QVQLVQSGAE VKKPGASVKV SCKASGYTFT DYIMHWVRQA PGQGLEWMGY INPYNDGSKY  60
TEKFQGRVTM TSDTSISTAY MELSRLRSDD TAVYYCARGT YYYGSALFDY WGQGTTVTVS  120
S                                                                                121

SEQ ID NO: 134           moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 134
QVQLVQSGAE VKKPGASVKV SCKASGYTFT DYIMHWVRQA PGQGLEWMGY INPYNDGSKY  60
TEKFQGRVTM TSDTSISTAY MELSRLRSDD TAVYYCARGT YYYGPQLFDY WGQGTTVTVS  120
S                                                                                121

SEQ ID NO: 135           moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 135
QVQLVQSGAE VKKPGASVKV SCKASGYTFT DYIMHWVRQA PGQGLEWMGY INPYNDGSKY  60
TEKFQGRVTM TSDTSISTAY MELSRLRSDD TAVYYCARGT YYYGSELFDY WGQGTTVTVS  120
S                                                                                121
```

What is claimed is:

1. An antibody that specifically binds to human CD19, wherein the antibody comprises (a) CDR-L1 comprising the amino acid sequence of SEQ ID NO: 43, (b) CDR-L2 comprising the amino acid sequence of SEQ ID NO: 44, (c) CDR-L3 comprising the amino acid sequence of SEQ ID NO: 45, (d) CDR-H1 comprising the amino acid sequence of SEQ ID NO: 46, (e) CDR-H2 comprising the amino acid sequence of SEQ ID NO: 47, and (f) CDR-H3 comprising the amino acid sequence of SEQ ID NO: 48.

2. The antibody of claim 1, wherein the antibody is a monoclonal antibody.

3. The antibody of claim 1, wherein the antibody is a humanized or chimeric antibody.

4. The antibody of claim 1, wherein the antibody is an antibody fragment that specifically binds to human CD19.

5. The antibody of claim 1, wherein the antibody comprises a VH domain comprising an amino acid sequence of SEQ ID NO:99 and a VL domain comprising an amino acid sequence of SEQ ID NO:100.

6. The antibody of claim 1, which is a full length IgG1 antibody.

7. The antibody of claim 1, which is a full length IgG1 antibody with mutations L234A, L235A, and P329G, numbering accordingly to the EU index of Kabat.

8. The antibody of claim 1, wherein the antibody is cross reactive for human and cynomolgus CD19.

9. The antibody of claim 1, wherein said antibody is a bispecific antibody that specifically binds to human CD19 and to a second antigen.

10. A polynucleotide encoding the antibody of claim 1.

11. A vector comprising the polynucleotide according to claim 10.

12. A host cell comprising the vector of claim 11.

13. A method of producing the antibody of claim 1, comprising the steps of (i) culturing the host cell of claim 12 under conditions suitable for expression of the antibody, and (ii) recovering the antibody.

14. A pharmaceutical formulation comprising the antibody of claim 1 and a pharmaceutically acceptable carrier.

15. A method of treating a disease in an individual, comprising
    administering to the individual a therapeutically effective amount of the antibody of claim 1.

16. The method of claim 15, wherein the disease is a B-cell cancer.

17. The method of claim 15, wherein the disease is an autoimmune disease, rheumatoid arthritis, lupus, psoriasis, and a bone disease.

18. A polynucleotide encoding the antibody of claim 9.

19. A vector comprising the polynucleotide according to claim 18.

20. A host cell comprising the vector of claim 19.

21. A method of producing the antibody of claim 9, comprising the steps of (i) culturing the host cell of claim 12 under conditions suitable for expression of the antibody, and (ii) recovering the antibody.

22. A pharmaceutical formulation comprising the antibody of claim 9 and a pharmaceutically acceptable carrier.

23. A method of treating a CD-19-expressing disease in an individual, comprising administering to the individual a therapeutically effective amount of the antibody of claim 10.

24. The method of claim 23, wherein the disease is a B-cell cancer.

25. The method of claim 15, wherein the disease is an autoimmune disease, rheumatoid arthritis, lupus, psoriasis, or a bone disease.

* * * * *